US010856905B2

(12) United States Patent
Kerns et al.

(10) Patent No.: US 10,856,905 B2
(45) Date of Patent: Dec. 8, 2020

(54) CATHETER-BASED SYSTEM FOR DELIVERY AND RETRIEVAL OF A LEADLESS PACEMAKER

(71) Applicant: PACESETTER, INC., Sylmar, CA (US)

(72) Inventors: Scott Kerns, Plymouth, MN (US); Daniel Coyle, St. Louis Park, MN (US)

(73) Assignee: PACESETTER, INC., Sylmar, CA (US)

( * ) Notice: Subject to any disclaimer, the term of this patent is extended or adjusted under 35 U.S.C. 154(b) by 163 days.

(21) Appl. No.: 15/783,406

(22) Filed: Oct. 13, 2017

(65) Prior Publication Data

US 2018/0303513 A1    Oct. 25, 2018

Related U.S. Application Data

(60) Provisional application No. 62/503,888, filed on May 9, 2017, provisional application No. 62/434,537, filed on Dec. 15, 2016, provisional application No. 62/408,494, filed on Oct. 14, 2016.

(51) Int. Cl.
| | |
|---|---|
| *A61B 17/34* | (2006.01) |
| *A61M 25/01* | (2006.01) |
| *A61N 1/375* | (2006.01) |
| *A61B 17/3205* | (2006.01) |
| *A61B 17/00* | (2006.01) |
| *A61M 25/06* | (2006.01) |

(Continued)

(52) U.S. Cl.
CPC .... *A61B 17/3468* (2013.01); *A61B 17/32053* (2013.01); *A61M 25/0136* (2013.01); *A61M 25/0147* (2013.01); *A61N 1/3756* (2013.01); *A61N 1/37512* (2017.08); *A61B 2017/00358* (2013.01); *A61B 2017/00407* (2013.01); *A61M 25/0009* (2013.01); *A61M 25/0082* (2013.01); *A61M 25/0097* (2013.01); *A61M 25/0108* (2013.01); *A61M 25/0662* (2013.01); *A61M 2025/0024* (2013.01); *A61M 2025/0681* (2013.01); *A61N 1/362* (2013.01); *A61N 1/37518* (2017.08)

(58) Field of Classification Search
CPC ...... A61B 17/3468; A61B 2017/00358; A61N 1/3756; A61N 1/37512
See application file for complete search history.

(56) References Cited

U.S. PATENT DOCUMENTS

| | | |
|---|---|---|
| 3,123,484 A | 3/1964 | Pokras et al. |
| 3,148,072 A | 9/1964 | West et al. |
| 3,338,726 A | 8/1967 | Berzins |

(Continued)

OTHER PUBLICATIONS

Office Action for U.S. Appl. No. 15/783,430, filed Oct. 13, 2017, 40 pgs, (dated Aug. 6, 2019).

*Primary Examiner* — Sarah A Simpson
(74) *Attorney, Agent, or Firm* — Womble Bond Dickinson (US) LLP

(57) ABSTRACT

Catheter-based delivery systems for delivery and retrieval of a leadless pacemaker include features to facilitate improved manipulation of the catheter and improved capture and docking functionality of leadless pacemakers. Such functionality includes mechanisms directed to deflecting and locking a deflectable catheter, maintaining tension on a retrieval feature, protection from anti-rotation, and improved docking cap and drive gear assemblies.

20 Claims, 62 Drawing Sheets

(51) Int. Cl.
  *A61M 25/00* (2006.01)
  *A61N 1/362* (2006.01)

(56) References Cited

U.S. PATENT DOCUMENTS

| | | | |
|---|---|---|---|
| 3,719,508 A | 3/1973 | Gulla et al. | |
| 3,745,039 A | 7/1973 | Feldstein | |
| 3,754,939 A | 8/1973 | Pearlstein et al. | |
| 3,915,717 A | 10/1975 | Feldstein et al. | |
| 4,152,164 A | 5/1979 | Gulla et al. | |
| 5,725,512 A | 3/1998 | Swartz | |
| 6,143,059 A | 11/2000 | Tangi et al. | |
| 6,281,157 B1 | 8/2001 | Tangi et al. | |
| 6,524,642 B1 | 2/2003 | Leibman et al. | |
| 6,650,923 B1 | 11/2003 | Lesh et al. | |
| 7,158,838 B2 | 1/2007 | Seifert et al. | |
| 7,846,503 B2 | 12/2010 | Stark et al. | |
| 8,527,068 B2 | 9/2013 | Ostroff | |
| 8,615,310 B2 | 12/2013 | Khairkhahan et al. | |
| 8,945,146 B2 | 2/2015 | Steingisser et al. | |
| 8,958,892 B2 | 2/2015 | Khairkhahan et al. | |
| 9,126,032 B2 | 9/2015 | Khairkhahan et al. | |
| 9,205,225 B2 | 12/2015 | Khairkhahan et al. | |
| 9,320,590 B2 | 4/2016 | Zaver et al. | |
| 9,393,427 B2 | 7/2016 | Schmidt et al. | |
| 9,462,699 B2 | 10/2016 | Radi et al. | |
| 9,492,674 B2 | 11/2016 | Schmidt et al. | |
| 9,539,423 B2 * | 1/2017 | Bonner | A61N 1/0592 |
| 9,700,732 B2 | 7/2017 | Schmidt et al. | |
| 9,956,400 B2 | 5/2018 | Haasl et al. | |
| 9,993,648 B2 | 6/2018 | Kelly et al. | |
| 10,124,163 B2 | 11/2018 | Ollivier et al. | |
| 10,124,175 B2 | 11/2018 | Berthiaume et al. | |
| 10,188,425 B2 | 1/2019 | Khairkhahan et al. | |
| 10,238,864 B2 * | 3/2019 | Anderson | A61N 1/3756 |
| 10,286,220 B2 | 5/2019 | Schmidt et al. | |
| 2009/0234368 A1 | 9/2009 | Gore | |
| 2012/0095539 A1 | 4/2012 | Khairkhahan et al. | |
| 2012/0165827 A1 * | 6/2012 | Khairkhahan | A61N 1/362 606/129 |
| 2012/0197373 A1 | 8/2012 | Khairkhahan et al. | |
| 2014/0074114 A1 | 3/2014 | Khairkhahan et al. | |
| 2015/0051609 A1 | 2/2015 | Schmidt et al. | |
| 2015/0051611 A1 | 2/2015 | Schmidt et al. | |
| 2015/0051682 A1 | 2/2015 | Schmidt et al. | |
| 2015/0112361 A1 | 4/2015 | Khairkhahan et al. | |
| 2015/0283376 A1 | 10/2015 | Ollivier et al. | |
| 2015/0335884 A1 | 11/2015 | Khairkhahan et al. | |
| 2016/0067446 A1 | 3/2016 | Klenk et al. | |
| 2016/0067447 A1 | 3/2016 | Paspa et al. | |
| 2016/0096001 A1 * | 4/2016 | Eidenschink | A61M 25/001 606/129 |
| 2016/0114156 A1 * | 4/2016 | Haasl | A61N 1/0587 606/129 |
| 2016/0121007 A1 | 5/2016 | Dayton | |
| 2016/0213919 A1 | 7/2016 | Suwito et al. | |
| 2016/0279423 A1 | 9/2016 | Kelly et al. | |
| 2017/0028207 A1 | 2/2017 | Schmidt et al. | |
| 2017/0043158 A1 | 2/2017 | Kelly et al. | |
| 2018/0104449 A1 | 4/2018 | Amar et al. | |
| 2018/0104450 A1 | 4/2018 | Rickheim et al. | |
| 2018/0104451 A1 | 4/2018 | Kerns et al. | |
| 2018/0104452 A1 | 4/2018 | Goodman et al. | |
| 2018/0280703 A1 | 10/2018 | Hillukka et al. | |
| 2018/0303513 A1 | 10/2018 | Kerns et al. | |
| 2018/0303514 A1 | 10/2018 | Coyle et al. | |
| 2019/0110812 A1 | 4/2019 | Khairkhahan et al. | |
| 2019/0111248 A1 | 4/2019 | Eby et al. | |
| 2019/0175219 A1 | 6/2019 | Goodman et al. | |

\* cited by examiner

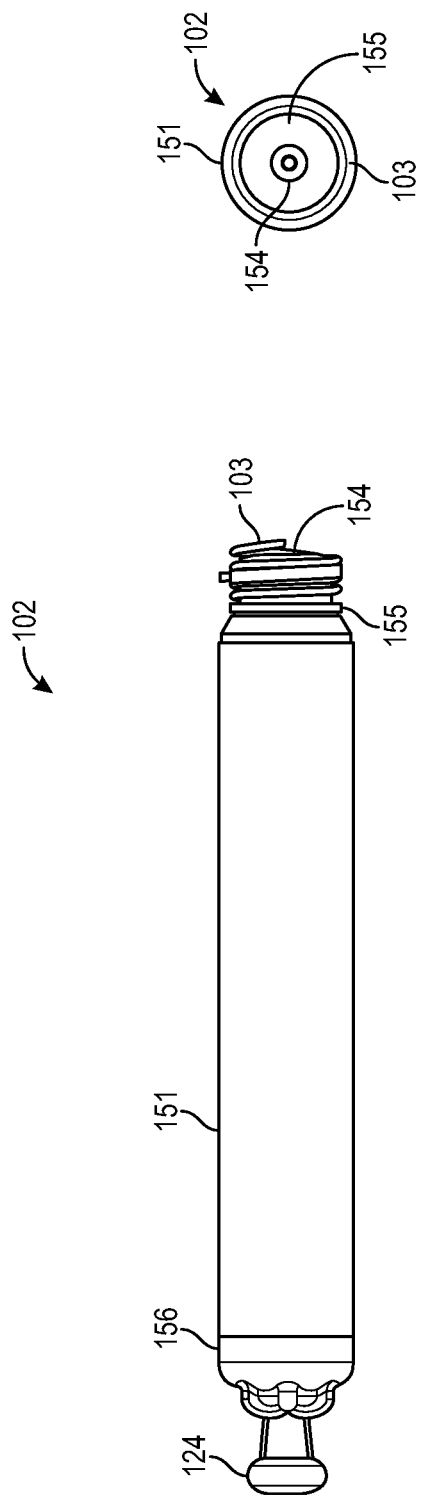

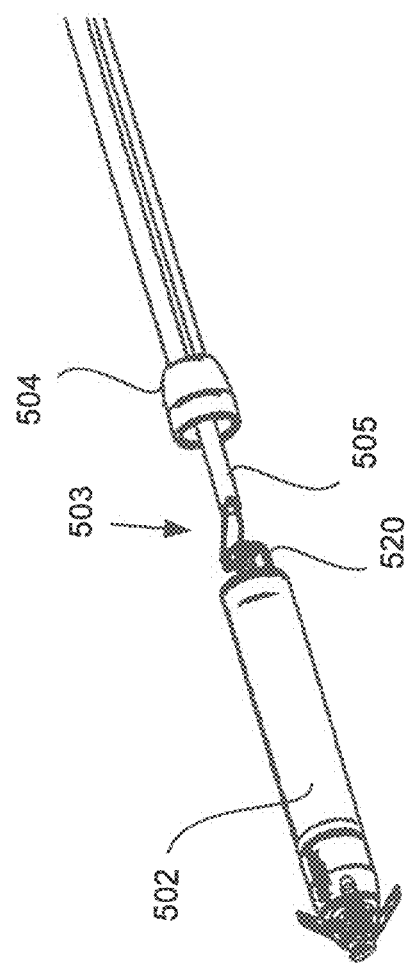

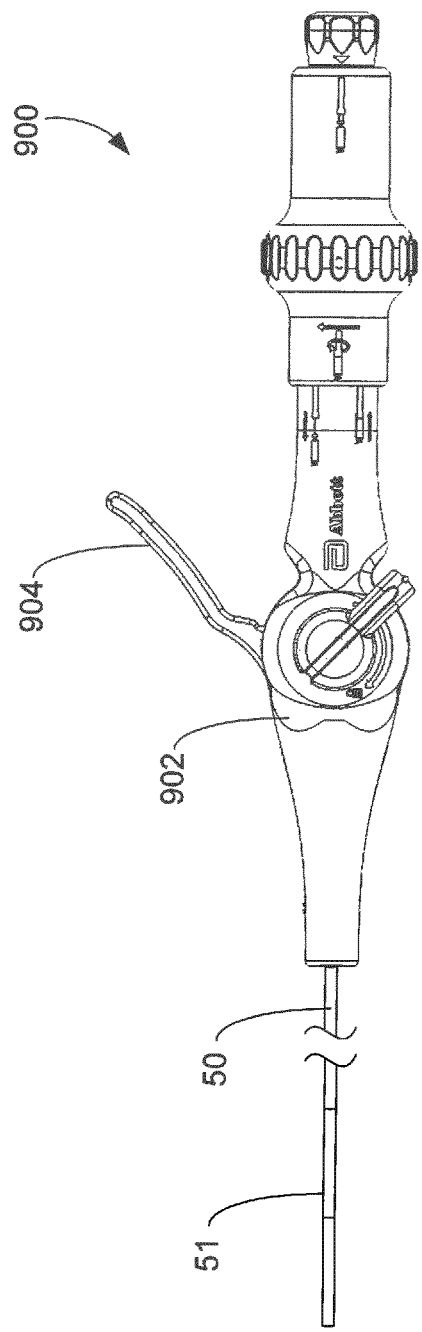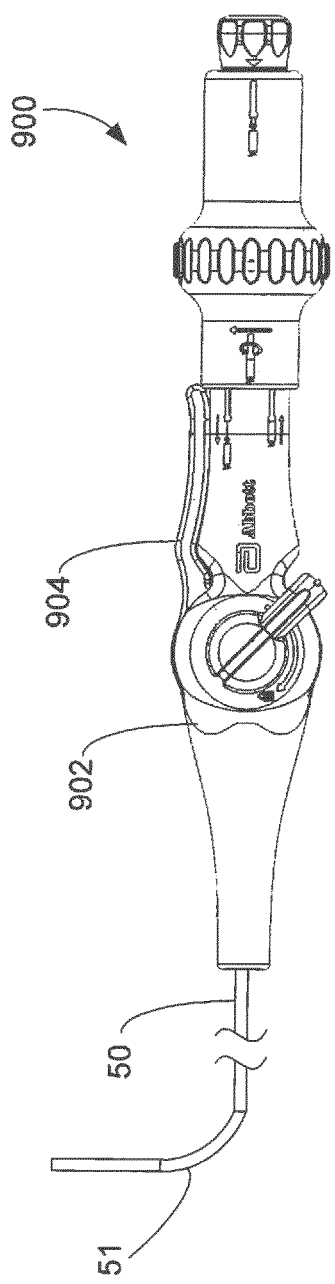
FIG. 9A
FIG. 9B

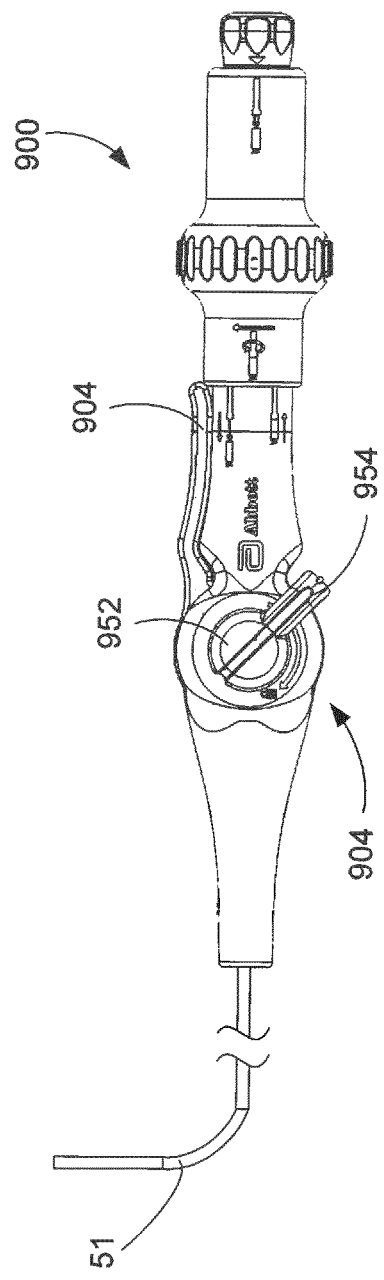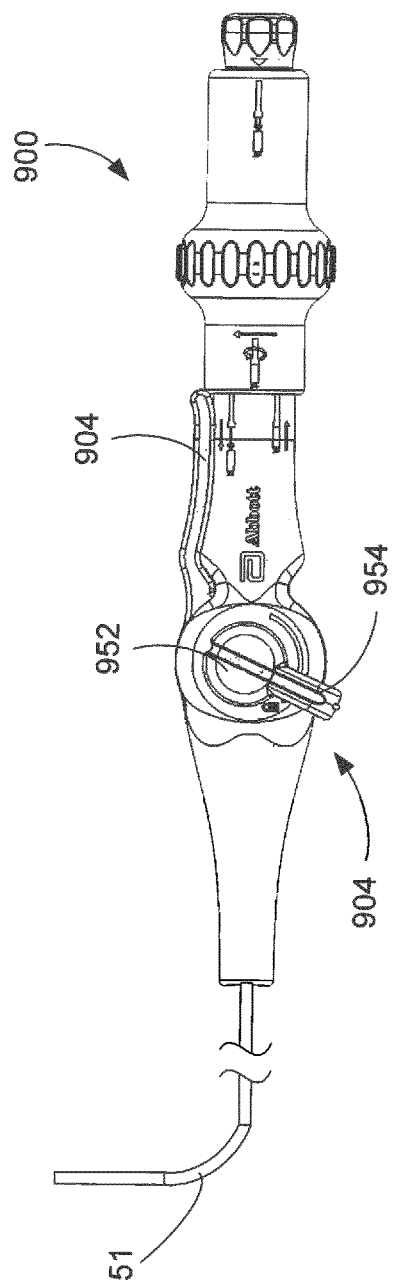
FIG. 11A
FIG. 11B

CATHETER-BASED SYSTEM FOR DELIVERY AND RETRIEVAL OF A LEADLESS PACEMAKER

CROSS-REFERENCE TO RELATED APPLICATIONS

This application claims the benefit of and priority to U.S. Provisional Patent Application Ser. No. 62/408,494, filed Oct. 14, 2016, entitled, "EXPANDABLE SLEEVE FOR DELIVERY/RETRIEVAL OF A LEADLESS PACEMAKER", U.S. Provisional Patent Application Ser. No. 62/434,537, filed Dec. 15, 2016, entitled, "EXPANDABLE SLEEVE FOR DELIVERY/RETRIEVAL OF A LEADLESS PACEMAKER," and U.S. Provisional Patent Application Ser. No. 62/503,888, filed May 9, 2017, entitled "CATHETER-BASED DELIVERY SYSTEM FOR DELIVERING A LEADLESS PACEMAKER EMPLOYING A LOCKING HUB". The disclosures of these co-pending related applications are incorporated by reference in their entirety into this present application,

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure relates to leadless cardiac pacemakers and related delivery and retrieval systems and methods. More specifically, the present disclosure relates to devices and methods for delivering and retrieving a leadless cardiac pacemaker via a catheter-based delivery system.

BACKGROUND

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. Pulse generator parameters are usually interrogated and modified by a programming device outside the body, via a loosely-coupled transformer with one inductance within the body and another outside, or via electromagnetic radiation with one antenna within the body and another outside. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Although more than one hundred thousand conventional cardiac pacing systems are implanted annually, various well-known difficulties exist, of which a few will be cited. For example, a pulse generator, when located subcutaneously, presents a bulge in the skin that patients can find unsightly, unpleasant, or irritating, and which patients can subconsciously or obsessively manipulate or "twiddle". Even without persistent manipulation, subcutaneous puke generators can exhibit erosion, extrusion, infection, and disconnection, insulation damage, or conductor breakage at the wire leads. Although sub-muscular or abdominal placement can address some concerns, such placement involves a more difficult surgical procedure for implantation and adjustment, which can prolong patient recovery.

A conventional pulse generator, whether pectoral or abdominal, has an interface for connection to and disconnection from the electrode leads that carry signals to and from the heart. Usually at least one male connector molding has at least one terminal pin at the proximal end of the electrode lead. The male connector mates with a corresponding female connector molding and terminal block within the connector molding at the pulse generator. Usually a setscrew is threaded in at least one terminal block per electrode lead to secure the connection electrically and mechanically. One or more O-rings usually are also supplied to help maintain electrical isolation between the connector moldings. A setscrew cap or slotted cover is typically included to provide electrical insulation of the setscrew. This briefly described complex connection between connectors and leads provides multiple opportunities for malfunction.

Other problematic aspects of conventional pacemakers relate to the separately implanted pulse generator and the pacing leads. By way of another example, the pacing leads, in particular, can become a site of infection and morbidity. Many of the issues associated with conventional pacemakers are resolved by the development of a self-contained and self-sustainable pacemaker, or so-called leadless pacemaker, as described in the applications cited below, Similar to active fixation implantable leads used with conventional pulse generators, leadless pacemakers are typically fixed to an intracardial implant site by an actively engaging mechanism such as a screw or helical member that screws into the myocardium.

Leadless pacemakers are typically delivered to an intracardial implant site via a delivery system including catheters, sheaths and/or introducers. Introduction of a leadless pacemaker into the venous system and navigation of the leadless pacemaker through and past delicate tissues and anatomical structures to the implantation site is a complicated task. To achieve this task, manipulation of the sheaths, catheters and introducers relative to each other must often be precise.

Similarly, retrieval of previously implanted leadless pacemakers requires precise manipulation of the catheters, sheaths and/or introducers to secure the implanted leadless pacemaker, disengage the leadless pacemaker from the intracardial implant site, and extract the leadless pacemaker through the venous system. Absent sufficient control and precision during the retrieval process, damage to one or more of the leadless pacemaker, the cardiac tissue of the implant site, and the venous system may result.

There is a need in the art for systems and methods that facilitate precise manipulation of a leadless pacemaker delivery and systems for purposes of both it and removing leadless pacemakers from intractardial implant sites.

SUMMARY OF THE DISCLOSURE

In one embodiment of the present disclosure a handle for a catheter is provided. The catheter includes a deflectable catheter section and a pull wire coupled to the deflectable catheter section and defines defining a longitudinal axis. The handle includes a housing, a hub disposed within the housing and coupled to the pull wire, and a deflection lever coupled to the hub. The deflection lever extends from a first side of the housing and is movable between a first lever position in which the deflection lever extends away from the longitudinal axis at a first angle and a second lever position in which the deflection lever extends away from the longitudinal axis at a second angle less than the first angle. The handle further includes a brake assembly coupled to the hub and rotatable between a first brake position in which the brake assembly applies a first resistance to rotation of the hub and a second brake position in which the brake assembly applies a second resistance to rotation of the hub greater than the first resistance. Movement of the lever from the first lever position to the second lever position rotates the hub, pulling the pull wire to deflect the deflectable catheter section.

In certain implementations, the lever extends from the housing at least partially in a proximal direction and may further define a moment arm having a predetermined length relative to the center of the hub. The first and second angles of the lever may also be within predetermined ranges.

The hub may also include a wall extending at least partially around the hub that at least partially guides the pull wire. The wall may be disposed at a predetermined radius from a center of the hub and have a predetermined arc length. A multiplier post about which the pull wire is routed may also be included. The multiplier post may generally be adapted to remain in a fixed position relative to the housing when the hub is rotated.

The brake assembly may include a lever extending from the housing opposite the deflection lever. For example, when in the first brake position, the lever may extend at least partially in a proximal direction such that rotation of the brake assembly from the first brake position to the second brake position may include rotating the brake assembly in a distal direction.

In certain implementations, movement of the deflection lever from the first lever position to the second lever position causes rotation of the hub in a first rotation direction and the brake assembly is rotatable between the first brake position and the second brake position by rotating the brake assembly in the first direction.

In another embodiment of the present disclosure, a handle for a catheter is provided. The catheter includes a deflectable catheter section and a pull wire coupled to the deflectable catheter section. The handle defines a longitudinal axis and includes a housing, a hub disposed within the housing and coupled to the pull wire, and a deflection lever coupled to the hub. The deflection lever extends from a first side of the housing and is movable between a first lever position and a second lever position to deflect the deflectable catheter section. The handle further includes a brake assembly including a knob coupled to the hub and rotatable between a first brake position in which the brake assembly applies a first resistance to rotation of the hub and a second brake position in which the brake assembly applies a second resistance to rotation of the hub that is greater than the first resistance. The brake assembly further includes a brake lever coupled to the knob and extending from a second side of the housing opposite the first side.

In certain implementations, the brake assembly further includes a hub washer disposed within the housing and rotationally fixed relative to the hub such that the first resistance and the second resistance to rotation of the hub results from compression of the hub washer against the housing.

The brake assembly may further include a threaded shaft coupled to the knob and extending through the hub washer such that rotation of the knob causes translation of the knob along the shaft and compression of the housing between the knob and the hub washer. In such implementations, the knob may be coupled to the threaded shaft by a threaded insert disposed within the knob. The brake assembly may further include a brake washer disposed between the knob and the housing. In implementations including the threaded shaft, the threaded shaft may include a shaft end that is rotationally fixed within the housing.

In certain implementations the knob is rotatable from the first brake position to the second brake position by rotating the brake lever in a first direction and movement of the lever between the first lever position and the second lever position causes the hub to rotate in the first direction.

In yet another embodiment disclosed herein, a system for at least one of delivery or retrieval of an implantable medical device is provided. The system includes a deflectable catheter section, a pull wire coupled to the deflectable catheter section, and a handle defining a longitudinal axis. The handle further includes a housing, a hub disposed within the housing and coupled to the pull wire, and a deflection lever coupled to the hub. The deflection lever extends from a first side of the housing and is movable between a first lever position and a second lever position to deflect the deflectable catheter section. The handle further includes a brake assembly coupled to the hub and rotatable between a first brake position in which the brake assembly applies a first resistance to rotation of the hub and a second brake position in which the brake assembly applies a second resistance to rotation of the hub greater than the first resistance.

In certain implementations, the deflection lever extends from a first side of the housing and the brake assembly includes a brake lever extending from a second side of the housing opposite the first housing. In such implementations, the deflection lever substantially may extend in one of a proximal and a distal direction and the brake assembly may movable between the first brake position and the second brake position by applying a force to a brake lever in the distal and proximal direction, respectively.

In certain implementations, the deflectable catheter may passively return to an undeflected state and the brake assembly may be rotatable into a third brake position in which sufficient resistance is provided to prevent passive return of the deflectable catheter.

In still another embodiment, a handle of a catheter system is provided. The catheter system includes a sheath and a retrieval feature disposed within the sheath. The handle includes a first handle portion including a pawl and a second handle portion including a rack surface extending longitudinally along at least a section of the second handle portion. The rack surface is shaped to engage the pawl and is disposed, at least partially, within the first handle portion. The second handle portion is coupled to the retrieval feature such that the retrieval feature may be retracted by displacing the second handle portion relative to the first handle portion. The second handle portion is movable in a proximal direction from a first position in which the pawl does not engage the rack surface to a second position in which the pawl engages the rack surface.

In certain implementations, the first handle portion may further include a second pawl disposed opposite the pawl.

When in the second position, the rack surface and the pawl may prevent movement of the second handle portion in a distal direction.

In some implementations, the pawl includes a release that, when actuated, causes the pawl to disengage from the rack surface. The pawl may be is supported by a pivot pin and the release may be a push button that, when depressed, causes the pawl to rotate about the pin and to disengage the rack surface. The pawl may also be biased towards engagement with the rack surface by a biasing element. The biasing element may be, for example, at least one of a coil spring or a linear spring coupled to the pawl.

The rack surface may extends about the second handle portion such that, when in the second position, the second handle portion is rotatable relative to the first handle portion without disengaging the pawl from the rack surface. The second handle portion may define a retention feature disposed proximal the rack surface such that the pawl engages the retention feature when the second handle portion is disposed at a distal extent relative to the first handle portion.

In another embodiment, a retrieval system for retrieving an implanted medical device is provided. The retrieval system includes a catheter shaft, a snare extending through the catheter shaft, and a handle coupled to a proximal end of the catheter shaft. The handle further includes a first handle portion and a second handle portion disposed at least partially within the first handle portion. The second handle portion is coupled to the snare such that the snare may be retracted by displacing the second handle portion relative to the first handle portion. The handle further includes a ratchet selectively coupling the first handle portion and the second handle portion. The ratchet allows proximal movement of the second handle portion relative to the first handle portion while resisting distal movement of the second handle portion relative to the first handle portion.

In some Implementations, the first handle portion includes a pawl and the second handle portion includes a rack, the ratchet formed by the pawl and the rack.

The first handle portion may include a release that, when actuated, reduces resistance to distal movement of the second handle portion relative to the first handle portion. The release may, in certain implementations, include at least one button disposed on an exterior surface of the first handle portion.

In some implementations the first handle portion is movable between a first position in which the ratchet does not couple the first handle portion and the second handle portion and a second position in which the ratchet couples the first handle portion and the second handle portion.

The second handle portion may also be rotatable within the first handle portion when the second handle portion is in the second position.

In yet another embodiment, a handle for a catheter system is provided. The catheter system is adapted to retrieve an implanted medical and includes a sheath and a retrieval feature disposed within the sheath. The handle includes a first handle portion Including a first locking feature and a second handle portion including a second locking feature. The second handle portion is coupled to the retrieval feature such that the retrieval feature may be withdrawn into the sheath by displacing the second handle portion relative to the first handle portion. The second handle portion is also movable from a first position in which the first locking feature does not engage the second locking feature to a second position in which the first locking feature engages the second locking surface.

In some implementations the first locking feature and the second locking feature restrict distal movement of the second handle portion after the second handle portion is moved into the second position.

The second handle portion may further include a third locking feature disposed distal the second locking feature, the second handle portion further movable in a proximal direction into a third position in which the locking feature engages the third locking feature.

The first handle portion and the second handle portion may have a common longitudinal axis and the second handle portion may be movable relative to the first handle portion along the common longitudinal axis.

In another implementation, the locking feature may include a release mechanism that, when actuated, disengages the first locking feature from the second locking surface.

In one embodiment of the present disclosure, a handle of a catheter system is provided. The catheter system including a sheath and a snare disposed within the sheath. The handle includes a first handle portion including a wall and a protrusion extending inwardly from the wall and a second handle portion including a ratchet wheel disposed at a distal end of the second handle portion. The second handle portion is movable in a proximal direction from a first position in which the ratchet wheel is not aligned with the protrusion and a second position in which the ratchet wheel is aligned with the protrusion. When in the second position, the second handle portion is rotatable in a first direction but rotation in a second direction opposite the first direction is obstructed by the protrusion. In certain implementations, the first direction is clock-wise and the second direction is counter-clockwise.

In one implementation, the ratchet wheel includes a pair of offset semi-circular lobes.

In another implementation, the protrusion includes a fin. In such implementations the fin may include multiple adjacent fin segments defining gaps therebetween, the gaps being less than a width of the ratchet wheel.

The handle may further include a locking feature that locks the second handle portion in the second position when the second handle portion is moved into the second position. In such implementations, the first handle portion may include a pawl proximal the protrusion and the second handle portion includes a rack surface proximal the ratchet wheel, the locking feature including the pawl and the rack surface.

In certain implementations, the handle may further include a release that, when actuated, releases the second handle portion such that the second handle portion may be moved from the second position to the first position. In such implementations, the first handle portion may include at least one button and the release may include the at least one button.

In yet another embodiment a handle of a catheter system is provided. The catheter system includes a sheath and a snare disposed within the sheath. The handle includes a first handle portion including a pawl and a second handle portion disposed at least partially within the first handle portion. The second handle portion is coupled to the snare such that the snare may be retracted by displacing the second handle portion relative to the first handle portion. The second handle portion includes a rack surface extending longitudinally along at least a section of the second handle portion, the rack surface including a pair of adjacent rack teeth, and a ratchet wheel disposed between the rack teeth of the pair of adjacent rack teeth. The second handle portion is movable in a proximal direction from a first position in which the pawl is disengaged from each of the linear rack and the ratchet wheel and a second position in which the pawl is engaged with each of the linear rack and the ratchet wheel.

In certain implementations, when in the second position, engagement of the pawl with the linear rack resists distal movement of the second handle portion. In such implementations, when in the second position, the second handle portion may be rotatable in a first direction but engagement of the pawl with the ratchet wheel may resist rotation of the second handle portion in a second direction opposite the first direction.

In some implementations, the ratchet wheel may include a plurality of ratchet wheel teeth disposed every sixty degrees about a perimeter of the ratchet wheel.

The handle may, in certain implementations, include a release that, when actuated, disengages the pawl from each of the rack surface and the ratchet wheel such that the second handle portion may be moved in a distal direction from the second position to the first position.

The rack surface may, in some implementations, include a second pair of adjacent rack teeth and a second ratchet wheel disposed between the rack teeth of the second pair of adjacent rack teeth.

In still another implementation of the present disclosure, a retrieval system for retrieving an implanted medical device is provided. The retrieval system includes a catheter shaft, a snare extending through the catheter shaft, and a handle coupled to a proximal end of the catheter shaft. The handle includes a first handle portion including a first counter-rotation feature and a second handle portion including a second counter-rotation feature, the second handle portion coupled to the snare such that the snare is retracted by displacing the second handle portion relative to the first handle portion. The second handle portion is movable from a first position in which the first counter-rotation feature does not engage the second counter-rotation feature to a second position in which the first locking feature engages the second locking surface. In some implementations, when in the second position, the second handle portion may be restricted from moving towards the first position.

In certain implementations, the first counter-rotation feature includes a protrusion extending from a wall of the first handle portion.

The second counter-rotation feature may, in some implementations, include a ratchet wheel disposed on a distal end of the second handle portion. In such implementations, the ratchet wheel may include a pair of offset semi-circular lobes.

The retrieval system may further include a release that, when actuated, reduces the restriction to movement of the second handle portion towards the first position.

In an embodiment of the present disclosure, a system for retrieving an implantable medical device from within a patient is provided. The system includes a torque shaft, a retrieval feature extending through the torque shaft, and a handle coupled to the torque shaft such that rotation of the handle rotates the torque shaft. The handle includes a torsion release assembly coupled to the retrieval feature that further includes a first gear and that is rotationally supported within the handle. The system further includes a shuttle coupled to the handle and including a second gear. The shuttle is translatable between a first shuttle position in which the first gear is engaged with the second gear such that rotation of the handle rotates the torsion release assembly, and a second shuttle position in which the first gear is disengaged from the second gear such that rotation of the handle does not rotate the torsion release assembly. The shuttle may be rotationally fixed relative to the handle. In certain implementations, the first shuttle position corresponds to a proximal shuttle position and the second shuttle position is a distal shuttle position. Further, when in the second shuttle position, the first gear may be disposed within the second gear.

In certain implementations, the system further includes a bearing disposed within the housing such that the torsion release assembly is rotationally supported within the handle by the bearing. The bearing may include a ball bearing including at least one of metal or plastic balls.

The first gear may have a substantially square cross-section and the second gear may define a substantially square cavity into which the first gear is inserted when the shuttle is in the first shuttle position. In such implementations, the second gear may extend along a longitudinal axis normal to a cross-sectional plane of the second gear and the second gear may include a proximal gear end. The proximal gear end may include a first half having a first face defining a first plane oriented at a first angle relative to the cross-sectional plane and a second half having a second face defining a second plane oriented at a second angle relative to the cross-sectional plane such that the first angle and the second angle are supplementary and the first plane and the second plane intersect along a line perpendicular to the longitudinal axis.

In certain implementations, the first gear may include a shaft and a plurality of first splines extending along the shaft. The second gear may include at least one second spline extending parallel to each of the plurality of first splines such that, when in the second position, the at least one second spline is disposed between adjacent splines of the plurality of first splines.

In another embodiment, a torsion release system for an elongated body of a medical device having a rotatable handle is provided. The torsion release system includes a first gear coupled to the elongated body and rotationally supported within the rotatable handle and a second gear rotationally fixed to the rotatable handle. The first gear and the second gear transition between a first configuration in which the first gear is engaged with the second gear such that rotation of the rotatable handle rotates the first gear and transmits torque to the elongated body, and a second configuration in which the first gear is disengaged from the second gear such that rotation of the handle does not rotate the first gear. In certain implementations, transition between the first configuration and the second configuration includes translating the second gear between a first position corresponding to the first configuration and a second position corresponding to the second configuration.

When in the second configuration, the first gear may freely rotatable within the housing. For example, in some implementations, the first gear may be rotationally supported within the rotatable handle by a ball bearing.

When in the second configuration, the first gear may be at least partially disposed within the second gear. In such implementations, the first gear may include has a substantially square cross-section and the second gear may define a substantially square cavity into which the first gear is inserted in the second configuration.

In yet another embodiment, a system for retrieving an implantable medical device from within a patient is provided. The system includes a torque shaft, a retrieval feature extending through the torque shaft, a handle coupled to the torque shaft such that rotation of the handle rotates the torque shaft, a selectively rotatable body coupled to the retrieval feature, and a shuttle rotationally fixed relative to the handle. The shuttle and selectively rotatable body transition between a first configuration in which the shuttle is engaged with the selectively rotatable body, thereby preventing rotation of the selectively rotatable body relative to the handle, and a second configuration in which the shuttle is disengaged from the selectively rotatable body and the selectively rotatable body is permitted to rotate relative to the handle.

In some implementations, the selectively rotatable body includes a first gear and the shuttle includes a second gear, the first gear engaging the second gear when in the first configuration.

In certain implementations, when the retrieval feature is under torsion in a first rotational direction and the system is in the first configuration, transition into the second configuration may release the torsion and causes rotation of the retrieval feature and the selectively rotatable body in a second rotational direction opposite the first direction.

The system may further include a rotatable mount disposed within the handle. In such implementations, the selectively rotatable body may be supported by the rotatable mount within the handle.

In one embodiment of the present disclosure, a system for retrieving an Implantable medical device from within a patient is provided. The system includes a catheter shaft, a handle coupled to a proximal end of the catheter shaft, and a docking cap coupled to a distal end of the catheter shaft. The docking cap defines a docking cap volume and includes a proximal cap end coupled to the catheter shaft, a distal annulus disposed opposite the proximal cap, and a plurality of longitudinal members extending between the distal annulus and the proximal cap end, such that adjacent pairs of the plurality of longitudinal members define openings into the docking cap volume.

In certain implementations, the system includes a sheath disposed over at least a portion of the openings. In such implementations, the sheath may be or include a fluorinated ethylene propylene (FEP) sheet. Also in such implementations, the sheath may be shrink-wrapped about the longitudinal members.

In some implementations, the distal annulus includes a distal face, an internal surface perpendicular to the distal face, and a curved transition between the distal face and the internal surface. The curved transition may have a radius of curvature and an arc length within a predetermined range.

The system may further include a torque feature disposed on an interior surface of at least one of the longitudinal members. The torque feature may be shaped to engage a portion of the implantable medical device during retrieval. For example, the torque may include a protrusion extending into the docking cap volume. In some implementations, the torque feature may be offset from the distal annulus.

The docking cap may be formed from various materials including, without limitation, one or more of stainless steel (such as 304 stainless steel), titanium, and a polymer, such as polyether ether ketone (PEEK). In certain implementations, the material may also be loaded with a radiopaque additive.

In another embodiment, a catheter is provided. The catheter includes a catheter shaft having a distal shaft end and a docking cap coupled to the distal shaft end. The docking cap includes a proximal cap end coupled to the distal shaft end, a distal annulus disposed opposite the proximal cap, and a plurality of longitudinal members extending between the distal annulus and the proximal cap end such that adjacent pairs of the plurality of longitudinal members define openings into the docking cap volume.

In certain implementations, the catheter includes a sheath disposed over at least a portion of the openings. In such implementations, the sheath may be or include a fluorinated ethylene propylene (FEP) sheet that may be shrink-wrapped about the longitudinal members.

In some implementations, the distal annulus includes a distal face, an internal surface perpendicular to the distal face, and a curved transition between the distal face and the internal surface. The curved transition may have a radius of curvature and an arc length within a predetermined range.

The catheter may further include a torque feature disposed on an interior surface of at least one of the longitudinal members. The torque feature may be shaped to engage a portion of the implantable medical device during retrieval. For example, the torque may include a protrusion extending into the docking cap volume. In some implementations, the torque feature may be offset from the distal annulus.

In another embodiment of the present disclosure, a system for retrieving an implantable medical device from within a patient is provided. The system includes a catheter shaft, a torque shaft disposed within the catheter shaft, and a handle including a first handle portion coupled to the catheter shaft and a second handle portion coupled to the torque shaft. The system further includes a drive gear coupled to a distal end of the torque shaft and including a drive gear torque feature, the drive gear rotatable by rotating the torque shaft, and a docking cap rotatably coupled to a distal end of the catheter shaft. The docking cap defines a recess for at least partially receiving the drive gear and includes a recess torque feature disposed within the recess. When received by the docking cap, the drive gear is rotatable in a first direction into an engaged position in which the drive gear torque feature engages the recess torque feature such that further rotation of the drive gear rotates the docking cap in the first direction. In certain implementations, rotation of the drive gear in a second direction opposite the first direction when in the engaged position may disengage the drive gear torque feature from the recess torque feature.

In certain implementations, the drive gear includes a distal portion including a cuboid body having a substantially square shape. The cuboid body may include distal rounded corners. In some implementations, the square distal face may define a diagonal between a pair of opposing corners of the square distal face and the recess may be defined by a pair of first opposing walls and a pair of second opposing walls, the first opposing walls being longer than the diagonal and the second opposing walls being shorter than the diagonal. In such implementations, the recess torque feature is one or both of the first opposing walls and the drive gear torque feature is one or both of the opposing corners of the square distal face.

The docking cap may define a cutout in one of the first opposing walls. In such implementations, the cutout is shaped to receive one of the opposing corners of the drive gear when the drive gear is in the engaged position.

The drive gear may, in certain implementations, include a proximal portion that including a proximally tapering body.

The docking cap may include a protrusion extending laterally into the recess, the recess torque feature being the protrusion. In such implementations, the drive gear includes an outer face including a concave portion shaped to receive the protrusion during rotation of the drive gear in the first direction, a substantially flat portion, and a transition portion coupling the concave portion to the substantially flat portion such that the drive gear torque feature is the transition portion.

The docking cap may include a proximally slanted surface extending into the recess. In such implementations, the proximally slanted surface is shaped to guide the drive gear into the engaged position in response to rotation of the drive gear in the first direction.

In another embodiment, a system for retrieving an implantable medical device from within a patient is provided. The system includes a drive gear and a docking cap shaped to receive a proximal end of the implantable medical device. The drive gear is at least partially retractable within the docking cap and, when at least partially retracted within the docking cap, rotation of the drive gear in a first direction causes interference between the drive gear and the docking cap such that further rotation of the drive gear in the first direction rotates each of the drive gear and the docking cap. In some implementations, the drive gear interferes with the docking cap at a plurality of locations.

In some implementations, the drive gear includes a rounded distal corner and the docking cap includes an internal wall partially defining a recess within the docking cap such that the interference is between the rounded distal corner and the internal wall.

The docking cap may define a recess and include a protrusion extending laterally into the recess. In such implementations, the drive gear includes an outer face including a concave portion shaped to receive the protrusion during rotation of the drive gear in the first direction, a substantially flat portion, and a transition portion coupling the concave portion to the substantially flat portion. In such cases, the interference occurs between the transition portion and the protrusion.

In some implementations, the drive gear includes a distal portion including a cuboid body having a substantially square distal face and distal rounded corners. The drive gear may also include a proximal portion including a proximally tapering body.

In yet another embodiment, a system for delivering and retrieving an implantable medical device from within a patient is provided. The system includes a catheter shaft, a torque shaft disposed within the catheter shaft, and a handle including a first handle portion coupled to the catheter shaft and a second handle portion coupled to the torque shaft. The system further includes a drive gear coupled to a distal end of the torque shaft, the drive gear including a distal portion including a cuboid body having a substantially square distal face and rounded distal corners, and a docking cap rotatably coupled to a distal end of the catheter shaft. The square distal face of the drive gear defines a diagonal between opposing corners of the square distal face. The includes a pair of first opposing internal walls that are each longer than the diagonal, and a pair of second opposing internal walls that are each shorter than the diagonal. The pair of first internal opposing walls and the pair of second opposing internal walls define a recess for at least partially receiving the drive gear.

In some implementations, when received within the recess, the drive gear is rotatable in a first direction to engage at least one of the opposing corners with a respective one of the pair of first opposing internal walls such that, once engaged, rotation of the drive gear rotates the docking cap. In such implementations, when the at least one of the opposing corners is engaged with the respective one of the pair of first opposing internal walls, rotation of the drive gear in a second direction opposite the first direction may disengage the at least one of the opposing corners from the respective one of the pair of first opposing internal walls.

The drive gear may, in certain implementations, include a proximal portion coupled to the distal portion including a proximally tapering body.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A and 1B are, respectively, side and end views of an example leadless cardiac pacemaker.

FIGS. 5A-5C show various close-up views of a distal portion of a retrieval catheter system employing alternative capture mechanisms.

FIGS. 9A-9B are plan views of a handle for use with a retrieval and/or delivery system in an extended and depressed configuration, respectively.

FIGS. 11A-11B are plan views of the handle of FIG. 9B with a brake assembly in a first and second position, respectively.

DETAILED DESCRIPTION

Figure 1C:
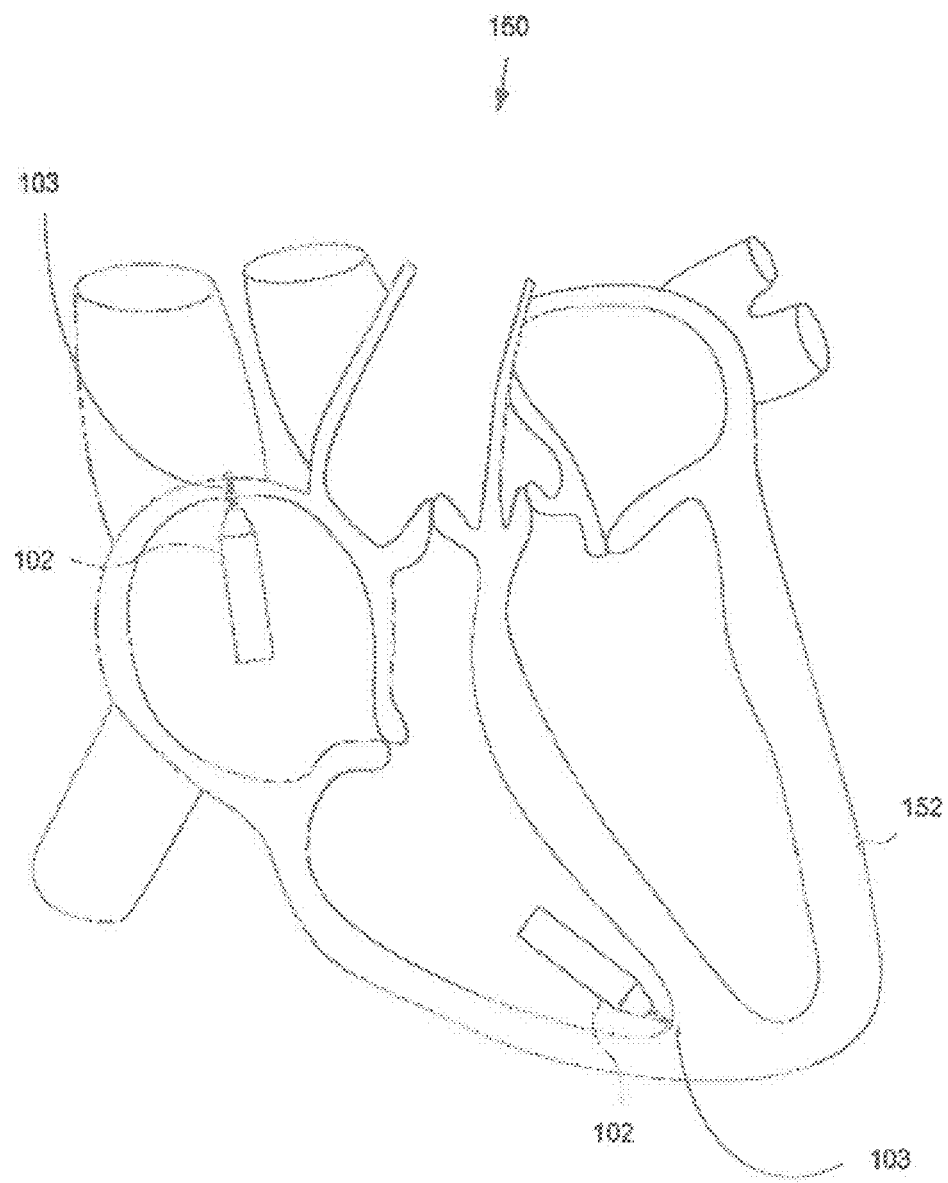
FIG. 1C is a diagrammatic medial-lateral cross section of a patient heart illustrating example implantation of leadless pacemakers in the patient heart.

The present disclosure is directed to a delivery and retrieval systems and associated methodology for delivering and retrieving leadless pacemakers to and from an implantation site in a patient.

As discussed below, in one embodiment, a delivery and retrieval system is provided including a deflectable catheter. To cause deflection of the catheter, a lever is included in a handle of the delivery and retrieval system. The lever is coupled to a hub that is in turn coupled to a deflectable tip of the deflectable catheter by a pull wire. During use, the lever is depressed to cause rotation of the hub, which pulls the pull wire and deflects the deflectable tip. In certain implementations, the lever is adapted for use with a single hand, thereby enabling a physician to perform additional tasks with his or her other hand. The delivery and retrieval system may further include a brake that is movable along a range of positions to increase resistance to rotation of the hub. Accordingly, a physician may depress the lever and apply the brake to reduce or eliminate the need for the physician to maintain force on the lever to maintain deflection of the catheter.

In another embodiment, a retrieval system having a tensioning system is provided. The tensioning assembly is incorporated into a handle of the retrieval system and includes a ratcheting mechanism that enables a user to apply and maintain tension on a snare or similar retrieval mechanism. The ratchet assembly generally couples a proximal handle portion and a distal handle portion of the retrieval system such that when the ratchet mechanism is engaged, the proximal handle portion may be moved proximally relative to the distal handle portion to increase tension but is prevented from translating in a distal direction absent actuation of a release mechanism.

In yet another embodiment, an anti-rotation assembly for a retrieval system is provided. The anti-rotation system resists or prevents rotation of a proximal handle portion of the retrieval system following capture and docking of a leadless pacemaker or similar implantable medical device. The anti-rotation functionality is achieved by a ratchet wheel disposed at the end of a shaft of the proximal handle portion. The ratchet wheel is positioned such that as the proximal handle portion is moved proximally relative to a distal handle portion, the ratchet wheel aligns with protrusions extending inwardly into the distal handle portion. The ratchet wheel and protrusions interact such that rotation in a first direction (generally corresponding to unscrewing of a leadless pacemaker or similar implantable medical device) is permitted while rotation in an opposite direction is obstructed.

In still another embodiment, a torsion release system for a handle of a retrieval system is provided. The system is generally adapted to enable dissipation of tension applied to a snare or similar retrieval mechanism during capture and docking of a Leadless pacemaker or similar implantable medical device. The system includes a first gear that is rotatable mounted within a handle and coupled to the retrieval mechanism. A shuttle is rotationally fixed but translatable relative to the handle such that when in a first position, a second gear coupled to the shuttle engages the first gear and rotation of the handle results in rotation of retrieval mechanism. In a second position, the shuttle is disengaged from the first gear, allowing the first gear to spin freely within a rotatable mount and enabling dissipation of torsion built up within the retrieval mechanism.

In yet another embodiment, an improved docking cap for a retrieval system is provided. The improved docking cap includes various features to improve capture and docking of leadless pacemakers and similar implantable medical devices. Such features includes, among other things, openings in the skies of the docking cap, reduced edges on the distal end of the docking cap, offset placement of an internal torque feature, and application of a sheath around the main body of the docking cap, each of which facilitates docking of a leadless pacemaker by reducing the likelihood that the leadless pacemaker will become caught on portions of the leadless pacemaker.

In another embodiment, an improved drive gear and docking cap design is provided that enables improved docking of the drive gear within the docking cap and self-aligning of the drive gear with the docking cap to facilitate more efficient torque transfer. The docking cap includes a recess into which the drive gear is retracted during docking of a leadless pacemaker. The recess and drive gear are shaped such that the drive gear may be retracted into the recess and subsequently rotated to engage a torque feature of the drive gear with a corresponding torque feature of the recess. For example, in certain implementations, the torque feature of the drive gear is a rounded corner of the drive gear and the torque feature of the recess is an internal wall of the docking cap.

In another embodiment, an atraumatic tip for use with a catheter of a retrieval and/or delivery system is provided. The atraumatic tip may, in certain implementations, include a star-shaped body adapted to expand to accommodate tissue build up around an implanted leadless pacemaker or similar medical device and various sizes of medical devices. The atraumatic tip may further include radiopaque markers for locating the atraumatic tip during use. Methods of manufacturing such atraumatic tips are also provided.

Before beginning a detailed discussion of the locking hub and associated method, a general overview of an example leadless pacemaker and catheter-based delivery system is provided as follows.

A. Overview of Leadless Pacemaker and a Catheter-Based Delivery System

FIGS. 1A-1B illustrate an example leadless cardiac pacemaker 102. The leadless pacemaker 102 can communicate by conducted communication, representing a substantial departure from conventional pacing systems. The leadless pacemaker can perform cardiac pacing that has many of the advantages of conventional cardiac pacemakers while extending performance, functionality, and operating characteristics with one or more of several improvements.

In some implementations of a cardiac pacing system, cardiac pacing is provided without a pulse generator located in the pectoral region or abdomen, without an electrode-lead separate from the pulse generator, without a communication coil or antenna, and without an additional requirement of battery power for transmitted communication.

FIG. 1C illustrates an embodiment of a cardiac pacing system 150 configured to attain these characteristics. The cardiac pacing system 150 includes one or more leadless cardiac pacemakers 102. Each leadless pacemaker is substantially enclosed in a hermetic housing 151 suitable for placement on or attachment to the inside or outside of a cardiac chamber, such as the right atrium and/or right ventricle of the patient heart 152, as can be understood from FIG. 1B. Attachment of a leadless pacemaker to the cardiac tissue can be accomplished via a helical anchor 103 on an anchor mount 155 extending from a distal end of the leadless pacemaker.

As can be understood from FIGS. 1A-1B, the leadless pacemaker 102 can have two or more electrodes 154, 156 located within, on, or near the housing 151, for delivering pacing pulses to muscle of the cardiac chamber and optionally for sensing electrical activity from the muscle, and for bidirectional communication with at least one other device within or outside the body. The housing can contain a primary battery to provide power for pacing, sensing, and communication, for example bidirectional communication. The housing 151 can optionally contain circuits for sensing cardiac activity from the electrodes 154, 156. The housing contains circuits for receiving information from at least one other device via the electrodes and contains circuits for generating pacing pulses for delivery via the electrodes. The housing can optionally contain circuits for transmitting information to at least one other device via the electrodes and can optionally contain circuits for monitoring device health. The housing contains circuits for controlling these operations in a predetermined manner.

In some implementations, a cardiac pacemaker can be adapted for delivery and implantation into tissue in the human body. In a particular embodiment, a leadless cardiac pacemaker can be adapted for implantation adjacent to heart tissue on the inside or outside wall of a cardiac chamber, using two or more electrodes located on or within the housing of the pacemaker, for pacing the cardiac chamber upon receiving a triggering signal from at least one other device within the body.

Leadless pacemakers or other leadless biostimulators are typically fixed to an intracardial implant site by an actively engaging mechanism or primary fixation mechanism such as a screw or helical member 103 that screws into the myocardium. Examples of such leadless biostimulators are described in the following publications, the disclosures of which are incorporated by reference: (1) U.S. Pat. No. 8,457,742, issued on Jun. 4, 2013, entitled "Leadless Cardiac Pacemaker System For Usage in Combination With An Implantable Cardioverter-Defibrillator"; (2) U.S. Pat. No. 9,358,400 issued on Jun. 7, 2016, entitled "Leadless Cardiac Pacemaker"; (3) U.S. Pat. No. 9,216,298, issued on Dec. 22, 2015, entitled "Leadless Cardiac Pacemaker System with Conductive Communication"; (4) U.S. Pat. No. 8,352,025 issued on Jan. 8, 2013, entitled "Leadless Cardiac Pacemaker Triggered by Conductive Communication"; (5) U.S. Pat. No. 7,937,148 issued on May 3, 2011, entitled "Rate Responsive Leadless Cardiac Pacemaker"; (6) U.S. Pat. No. 7,945,333 issued on May 17, 2011, entitled "Programmer for Biostimulator System"; (7) U.S. Pat. No. 8,010,209, issued on Aug. 30, 2011, entitled "Delivery System for Implantable Biostimulator"; and (8) International Application No. PCT/US2006/040564, filed on Oct. 13, 2006, entitled "Leadless Cardiac Pacemaker and System" and published as WO07047681A2 on Apr. 26, 2007.

In addition to the primary fixation mechanism, such as a helix, some leadless biostimulators may further include a secondary fixation mechanism to provide another feature for keeping the leadless biostimulator in place within the body. Secondary fixation mechanisms can be either active (e.g., the secondary fixation mechanism can actively engage tissue, either within or outside the heart), or can be passive (e.g., the secondary fixation mechanism is not attached to tissue but rather prevents the leadless biostimulator from moving around in the body in the case of accidental detachment). Further details on secondary fixation mechanisms can be found in U.S. Pat. No. 8,527,068, issued on Sep. 3, 2013.

Leadless pacemakers or other leadless biostimulators can be delivered to and retrieved from a patient using any of the delivery systems described herein. In some implementations, a leadless pacemaker is attached or connected to a delivery system and advanced intravenously into the heart. The delivery system can include features to engage the leadless pacemaker to allow fixation of the leadless pacemaker to tissue. For example, in implementations where the leadless pacemaker includes an active engaging mechanism, such as a screw or helical member, the delivery system can include a docking cap or key configured to engage the leadless pacemaker and apply torque to screw the active engaging mechanism into the tissue. In other Implementations, the delivery system includes caps designed to match the shape of a feature on the leadless pacemaker and apply torque to screw the active engaging mechanism into the tissue.

Figure 1D:
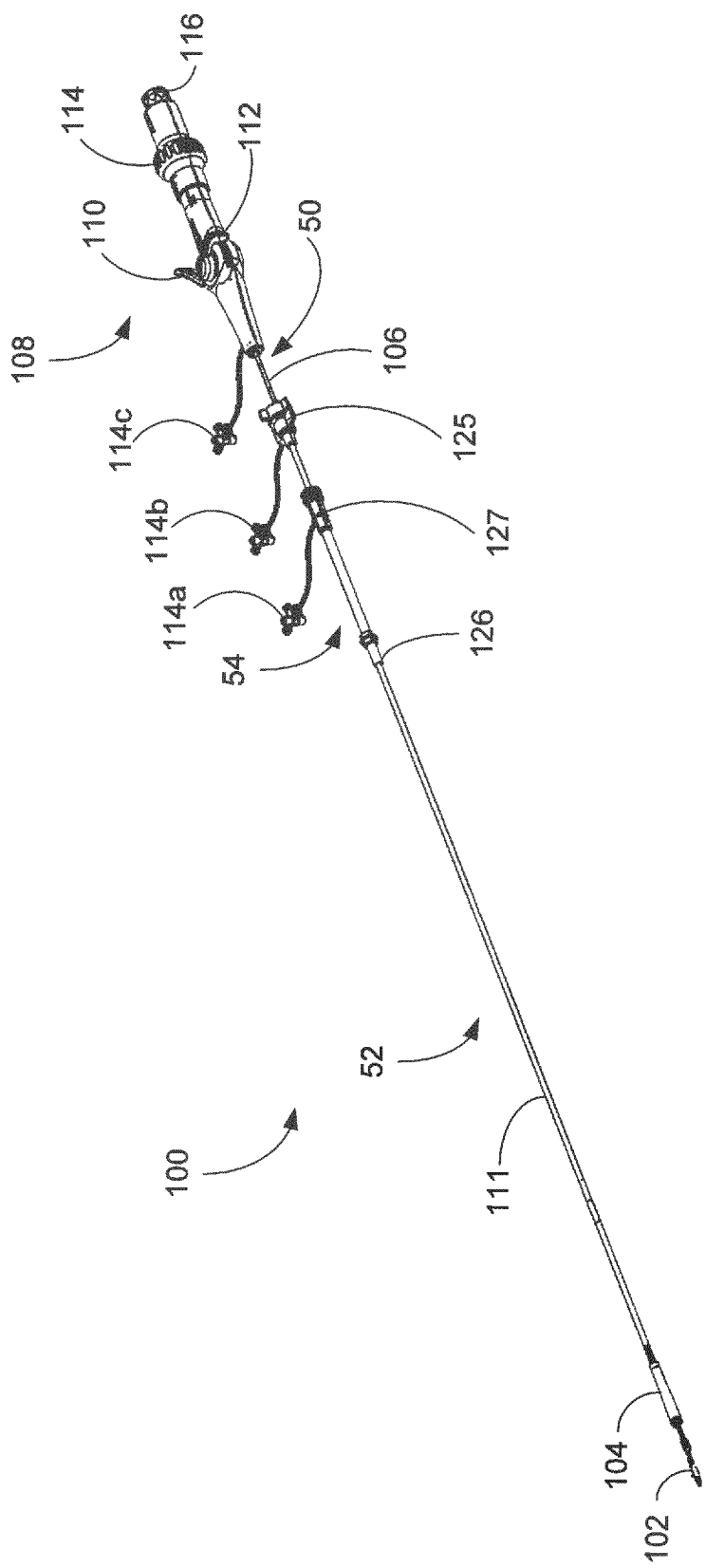
FIG. 1D is one embodiment of a system for delivering and/or retrieving a leadless pacemaker.

FIG. 1D illustrates a system 100 that may be used for delivery and/or retrieval of a leadless pacemaker 102 into or from a patient. The system 100 can include a deflectable catheter 50, a guide catheter 52, and an introducer sheath 54. As can be understood from FIG. 1D, the deflectable catheter 50 extends through the guide catheter 52 and includes a distal end and a proximal end. The distal end of the deflectable catheter is selectively connectable to the proximal end of the leadless pacemaker 102 and the proximal end of the deflectable catheter includes a handle 108 by which the user may cause the deflectable catheter shaft 106 to distally-proximally displace within the length of the guide catheter and, further, by which the user may actuate the distal end of the deflectable catheter to selectively connect and disconnect from a proximal end of the leadless pacemaker. The deflectable catheter 50 may extend from both the distal and proximal ends of the guide catheter 52.

The guide catheter 52 extends through the introducer sheath 54 and includes a distal end and a proximal end. The distal end of the guide catheter 52 includes a protective pacemaker sheath 104. The proximal end of the guide catheter includes a flush port 114b extending from a proximal hub 125. The guide catheter 52 extends from both the distal and proximal ends of the introducer sheath 54. The shaft 111 of the guide catheter 52 may also include one or more sections (not shown) having different durometers such that the reinforcement and corresponding bending resistance of the sections may be modified according to the specific application for which the pacemaker system 100 is being implemented. The introducer sheath 54 includes a distal end 126 and a proximal end. The proximal end of the introducer includes a flush port 114a and a hub 127.

As can be understood from FIG. 1D and for purposes of discussion, the system 100 may be considered to include the various components of the deflectable catheter 50, the guide catheter 52 and the introducer 54. For example, the system 100 may be considered to include the pacemaker sheath 104, the guide catheter shaft 111, the pacemaker introducer sheath 107, the handle 108, and the flush ports 114a, 114b, and 114c. The flush ports 114a, 114b, and 114c can be used to flush saline or other fluids through the introducer 54, the guide catheter 52, and the deflectable catheter shaft 106, respectively. The sheath 107 can be advanced distally over the catheter shaft 111 to provide additional steering and support for the delivery catheter during implantation and to surround the pacemaker as it is introduced through a trocar or introducer into the patient.

The handle 108 may further include additional elements to manipulate and actuate elements of the system 100. In general, the handle 108 may include elements directed to, without limitation, one or more of deflecting the deflectable catheter shaft 106, rotating the deflectable catheter shaft 106 (and any implantable medical device, such as the leadless pacemaker 102, coupled to the deflectable catheter shaft 106), extending and retracting the leadless pacemaker 102 (or other implantable medical device) relative to the protective sheath 104, and engaging or disengaging a coupling mechanism, such as a tether or lasso, to a corresponding feature of the leadless pacemaker 102 to couple the leadless pacemaker 102 to the system 100. For example, the handle 108 includes a deflection lever 110 for actuation of the deflectable catheter shaft 106 and a brake 112 for locking the position or otherwise increasing resistance to rotation of the deflection lever 110. The handle 108 further includes a docking shroud 114 that may rotated to apply torsion to the deflectable catheter shaft 106, thereby rotating the deflectable catheter shaft 106 and the leadless pacemaker 102 when coupled to the deflectable catheter shaft 106. The docking shroud 114 may also translate along the handle 108 to selectively extend and retract the leadless pacemaker 102 from a protective sheath 104 disposed at a distal end of the shaft 111. The handle 108 also includes a release knob 116 that, when rotated, causes engagement or disengagement of the coupling mechanism with the leadless pacemaker 102.

Figure 2A:
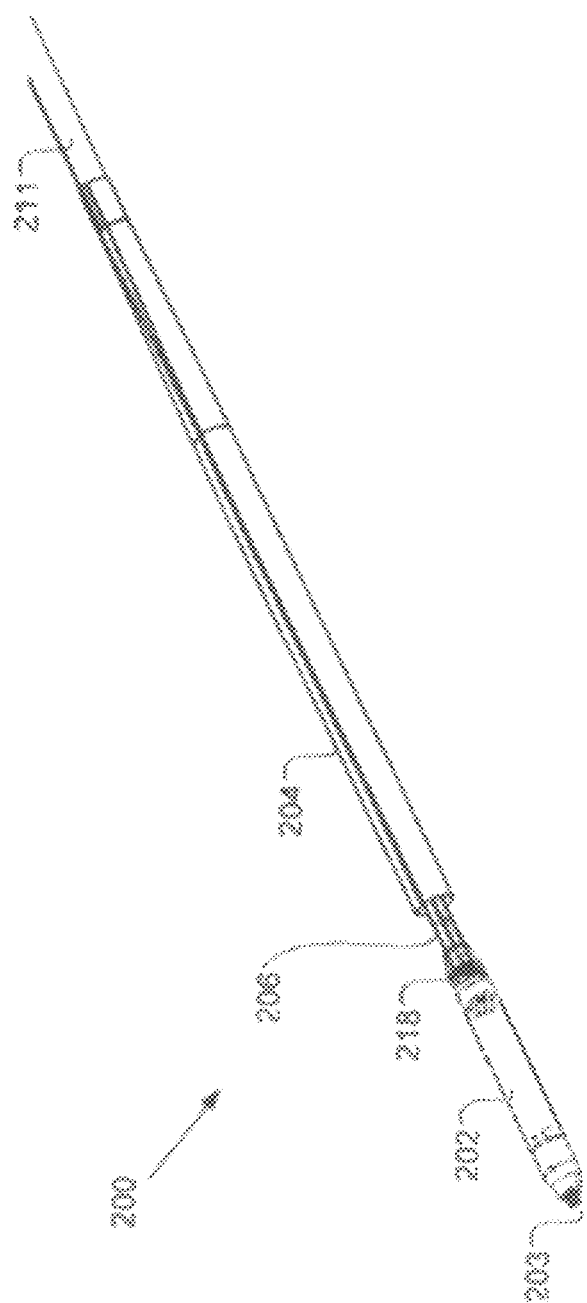
FIGS. 2A-2B are close-up views of a distal portion of the system.
Figure 2B:
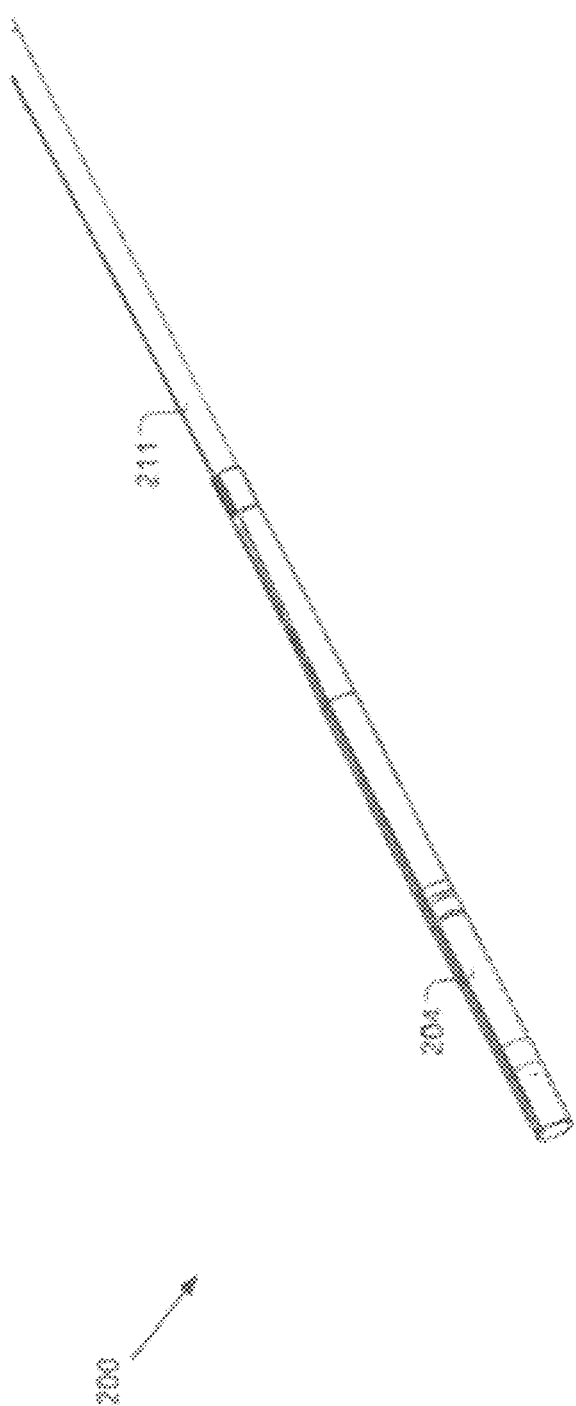

FIG. 2A is a close-up view of a distal portion of a system 200 as used for delivery of a pacemaker 202. The pacemaker 202 of FIG. 2A can include a helix 203 for attachment of the pacemaker to tissue. In FIG. 2A, the pacemaker is attached to a docking cap 218 of a catheter shaft 206. The pacemaker sheath 204 is shown pulled back proximally along the catheter shaft 206 and a guide catheter shaft 211 to expose the pacemaker 202 and the helix 203. In FIG. 2B, the pacemaker sheath 204 is extended distally along the guide catheter shaft 211 to cover the catheter shaft 206, the pacemaker 202, and the helix 203 to protect the tissue from the sharp edges of the helix 203 during implantation. When the pacemaker sheath 204 is pulled back proximally, as shown in FIG. 2A, the pacemaker 202 is in an exposed, delivery configuration. When the pacemaker sheath 204 is advanced distally to protect the pacemaker 202 and the helix 203, as shown in FIG. 2B, the pacemaker 202 is in a protected, advancement configuration.

Figure 3A:
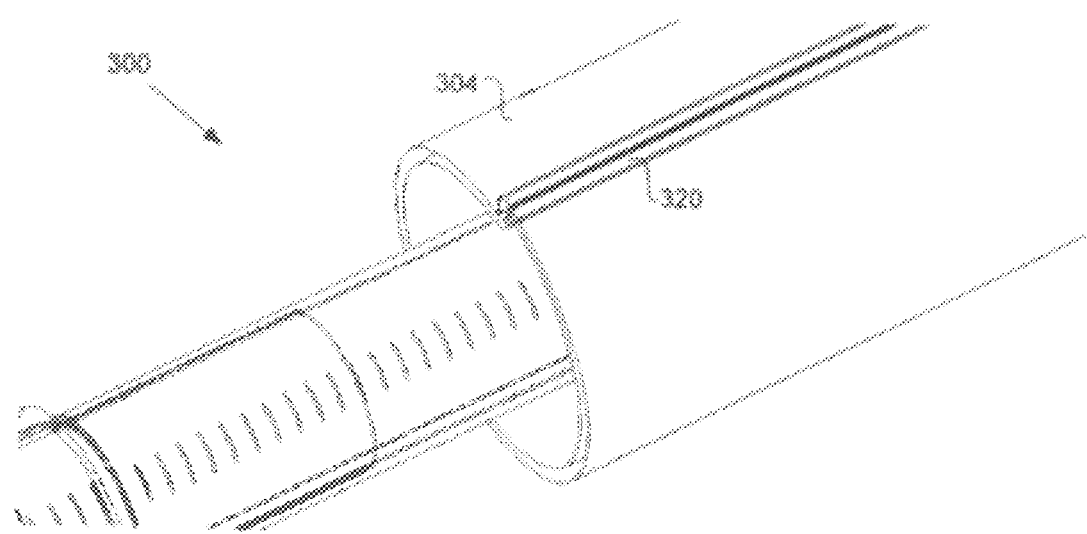
FIGS. 3A-3B are schematic side and cross-sectional views of a pacemaker sheath.
Figure 3B:
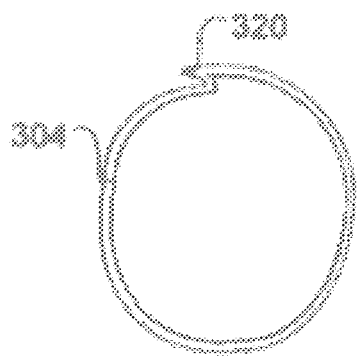

FIGS. 3A-3B are close-up and cross sectional views of a pacemaker sheath 304 of a system 300 as used for delivery of a leadless pacemaker. As shown, the pacemaker sheath 304 can include a crease or fold 320 along the length of the sheath 304. During initial insertion of the system 300 into a patient, a physician can gain access to the patient's venous system with an introducer sheath using the Seldinger technique (not shown). The system 300, including the leadless pacemaker and the catheter shaft, can then be advanced through the introducer sheath into the patient's venous system to facilitate delivery of the pacemaker into the heart. Reducing the diameter of the pacemaker, the delivery system, and thus the introducer sheath, provides for easier and less intrusive access to a patient's venous system.

By designing the pacemaker sheath 304 with a fold 320 that runs longitudinally along the sheath, the cross-sectional diameter of the pacemaker sheath 304 can be reduced by folding the sheath 304 over itself. Thus, during initial implantation of the pacemaker through an introducer sheath into the patient, the pacemaker sheath 304 can be positioned just proximally to the pacemaker, and folded along fold 320 so as to have a cross sectional diameter close to or equal to the same diameter as the pacemaker. This allows a smaller diameter introducer sheath to be used than would normally be necessary, since those delivery systems must incorporate a larger introducer sheath to allow passage of a full sized pacemaker sheath. After the delivery system is inserted through the introducer sheath into the patient, the sheath can be advanced distally over the leadless pacemaker. Advancing the pacemaker sheath 304 distally causes fold 320 to unfold, thereby increasing the diameter of the pacemaker sheath 304 so that it can slide over and cover the pacemaker and fixation helix. FIG. 3B is a cross-sectional view of the pacemaker helix 304 and fold 320, giving another view on how the cross-sectional diameter of the pacemaker sheath 304 can increase and decrease.

Figure 4A:
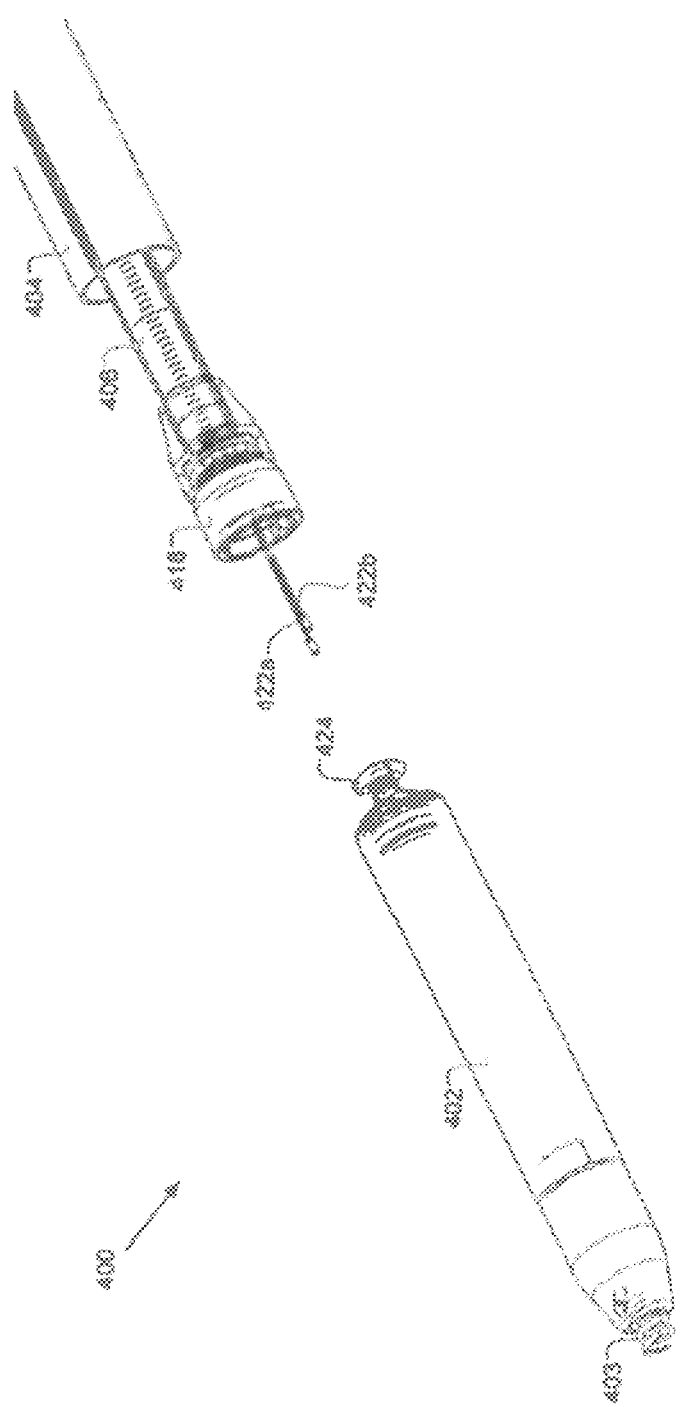
FIGS. 4A-4G are side views of a delivery system approaching, and then attaching to, a pacemaker.

FIG. 4A illustrates a system 400 for delivering a leadless pacemaker, including a pacemaker 402 including a helix 403 and an attachment feature 424, and the system 400 including a pacemaker sheath 404, a catheter shaft 406, a docking cap 418, and tethers 422a, 422b. The tethers 422a, 422b can include wires, shafts, tubes, cords, ropes, strings, or other similar structures that can extend throughout the catheter shaft 406. In some implementations, the tethers 422a, 422b include a shape memory material, such as nitinol. In other implementations, the tethers include stainless steel wires or braids. In FIG. 4A, the pacemaker 402 is not attached to docking cap 418 of the delivery catheter. The process of connecting the pacemaker to the delivery catheter will now be described.

Figure 4B:
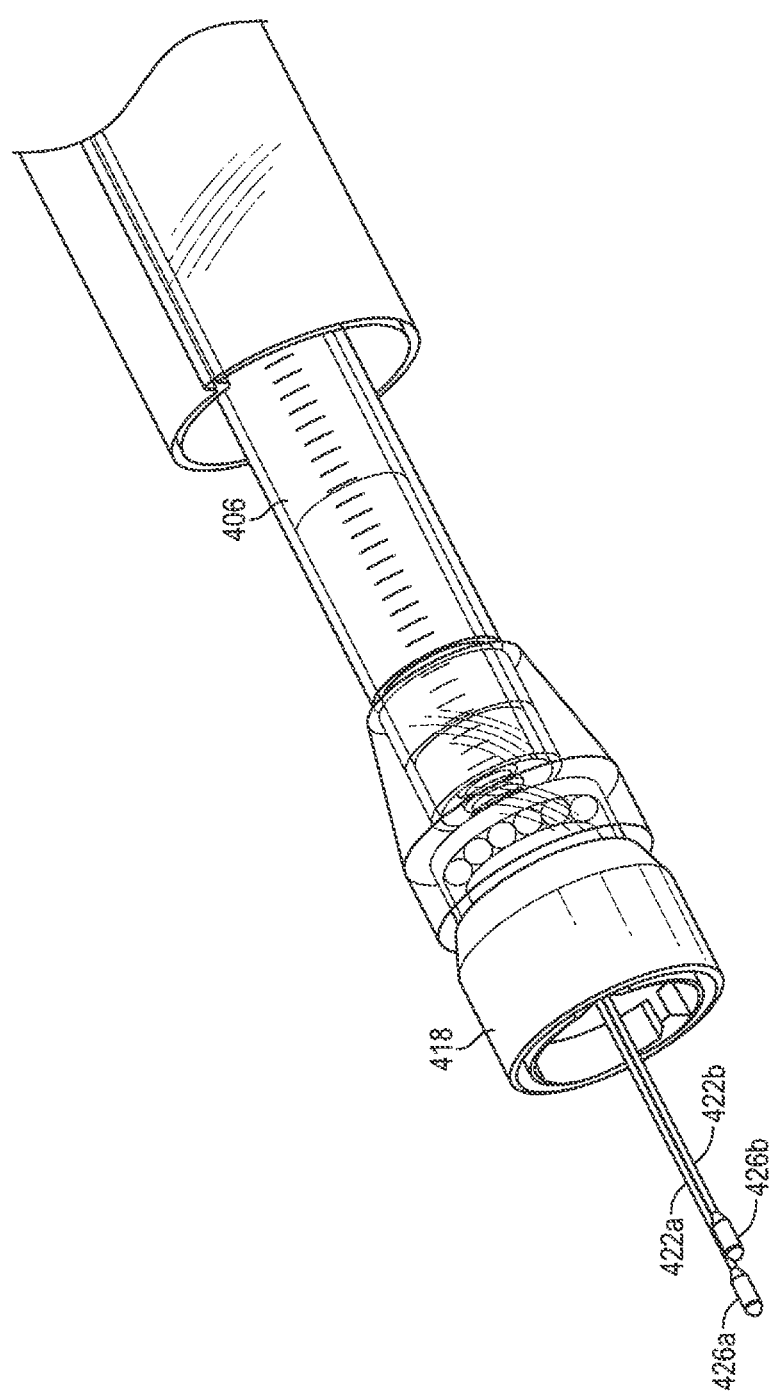

Referring to FIG. 4B, tethers 422a and 422b can include distal features 426a, 426b. The distal features 426a, 426b can be, for example, features on the tethers that protrude radially from the tether, such as bumps, spheres, cylinders, rectangles, or other similar shapes extending outwards from the tethers. In some implementations, the distal features can be expandable, such as balloons or expandable mechanical structures. Generally, the distal features have a cross sectional diameter larger than the cross sectional diameter of the tethers. As shown, in one embodiment, the distal feature 422a can be advanced further from the catheter than the distal feature 422b, so that when the tethers are pushed together, the distal feature 422b rests against the tether 422a. This causes the combined cross sectional diameter of both distal features and tethers to be less than if the distal features were lined up side by side. By way of comparison, in FIG. 4C the distal features 426a, 426b are lined up side by side and therefore have a greater combined cross sectional diameter when pressed together than is shown in FIG. 4B.

Figure 4C:
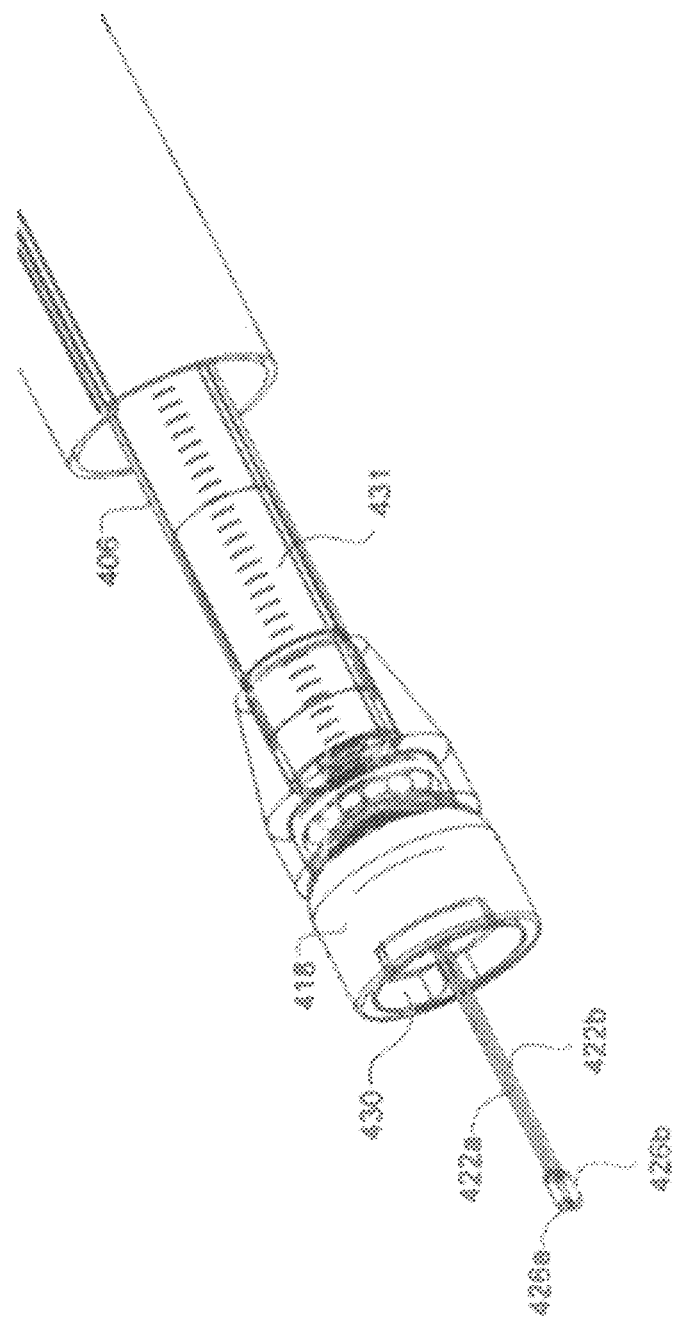
Figure 4D:
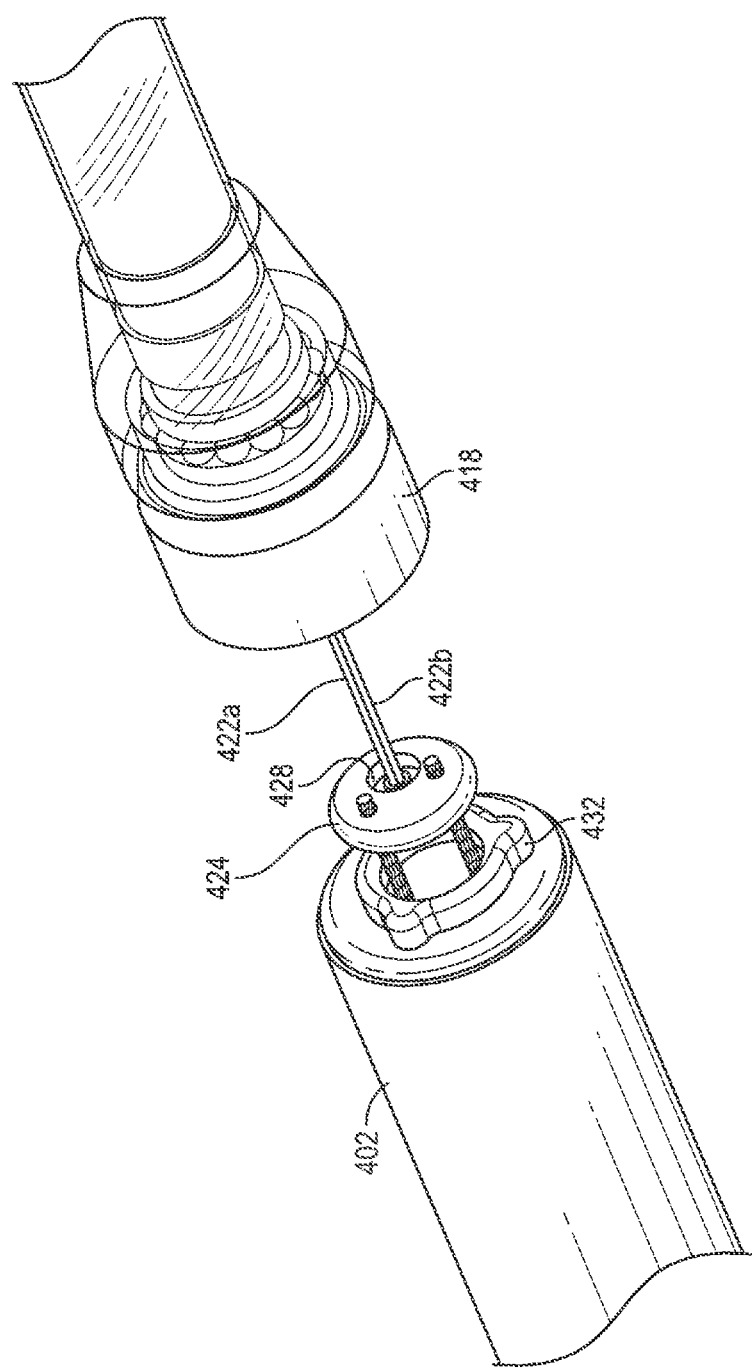
Figure 4E:
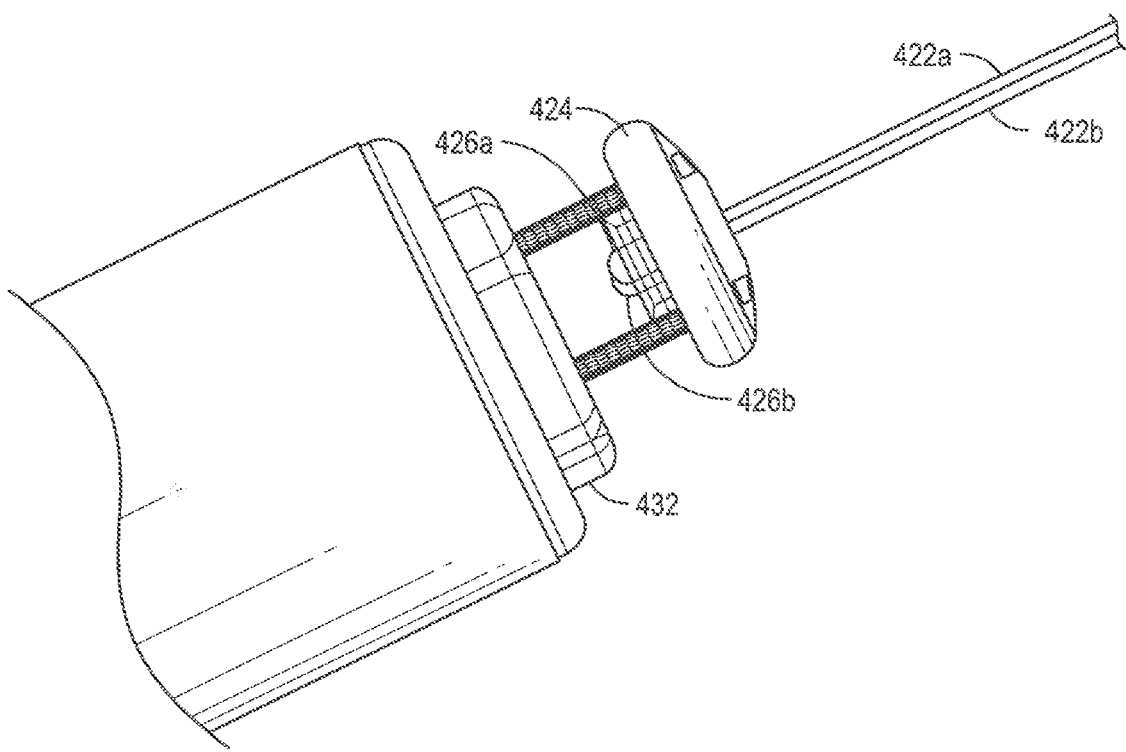
Figure 4F:
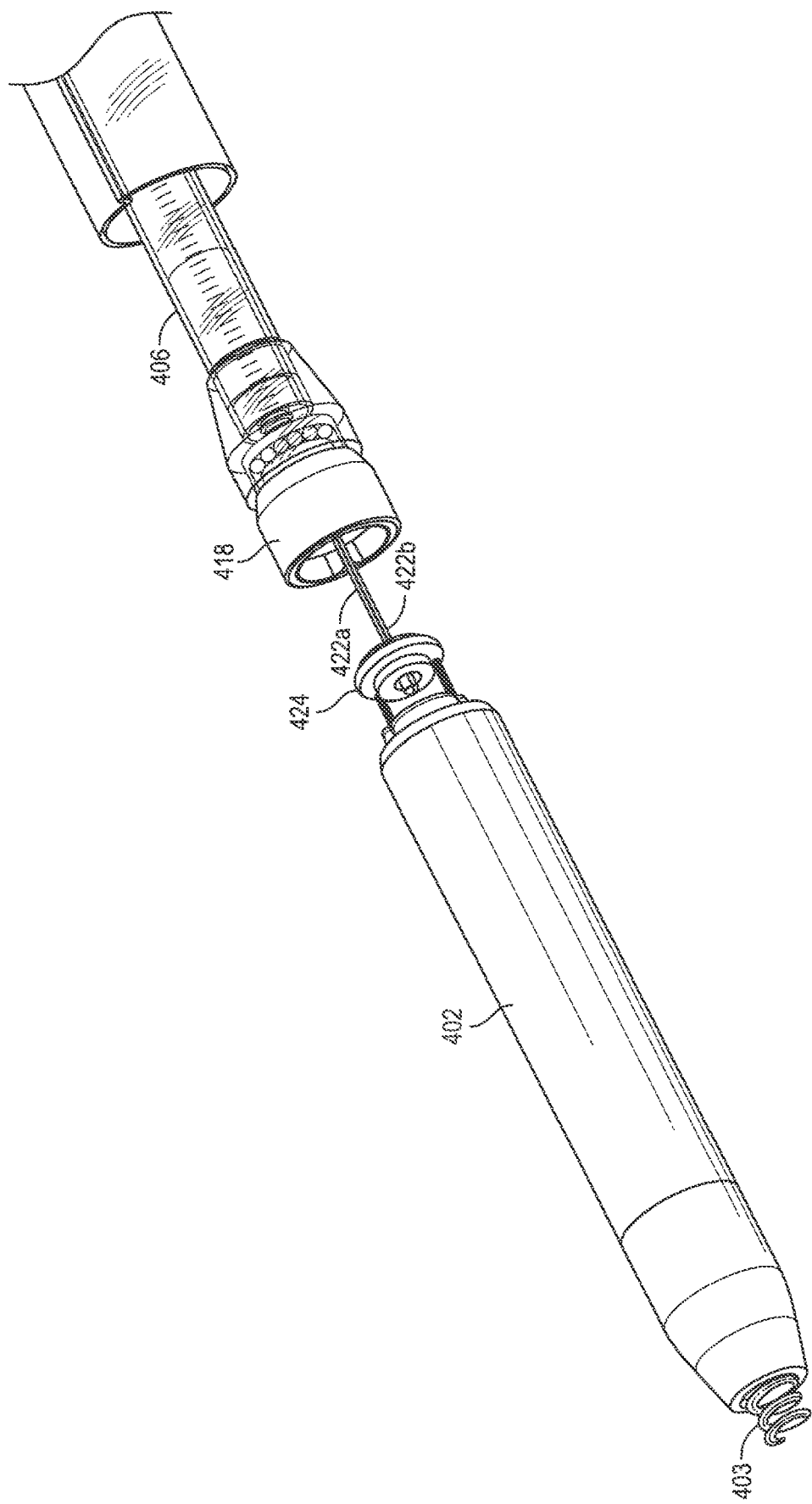

The length of the tethers 422a, 422b and thus the position of the distal features 426a, 426b, can be adjusted so that the distal features 426a, 426b are not aligned in a side by side configuration (e.g., the un-aligned configuration shown in FIGS. 4A-4B). When the tethers and distal features are in this un-aligned configuration, the cross sectional diameter of the distal features is reduced since the distal features are not positioned side by side. The tether distal features 426a, 426b can then be advanced in this un-aligned configuration through a hole 428 of an attachment feature 424 of the leadless pacemaker, as shown in FIGS. 4D-4F. In this implementation, the diameter of the hole 428 should be sufficiently large enough to avow the distal features 426a, 426b of the tethers 422a, 422b to pass when in the un-aligned configuration. Upon passing the distal features through the hole 428, the length of the tethers 422a, 422b can then be adjusted to align the distal features 426a, 426b in the side by side configuration (e.g., as shown in FIGS. 4C and 4E). When the distal features 426a, 426b are positioned side by side, the combined cross sectional diameter of the distal features 426a, 426b becomes larger than the diameter of the hole 428, which essentially locks the tethers 422a, 422b and distal features 426a, 426b in the attachment feature 424 be preventing the distal features 426a, 426b from being able to pass proximally through the hole 428.

Figure 4G:
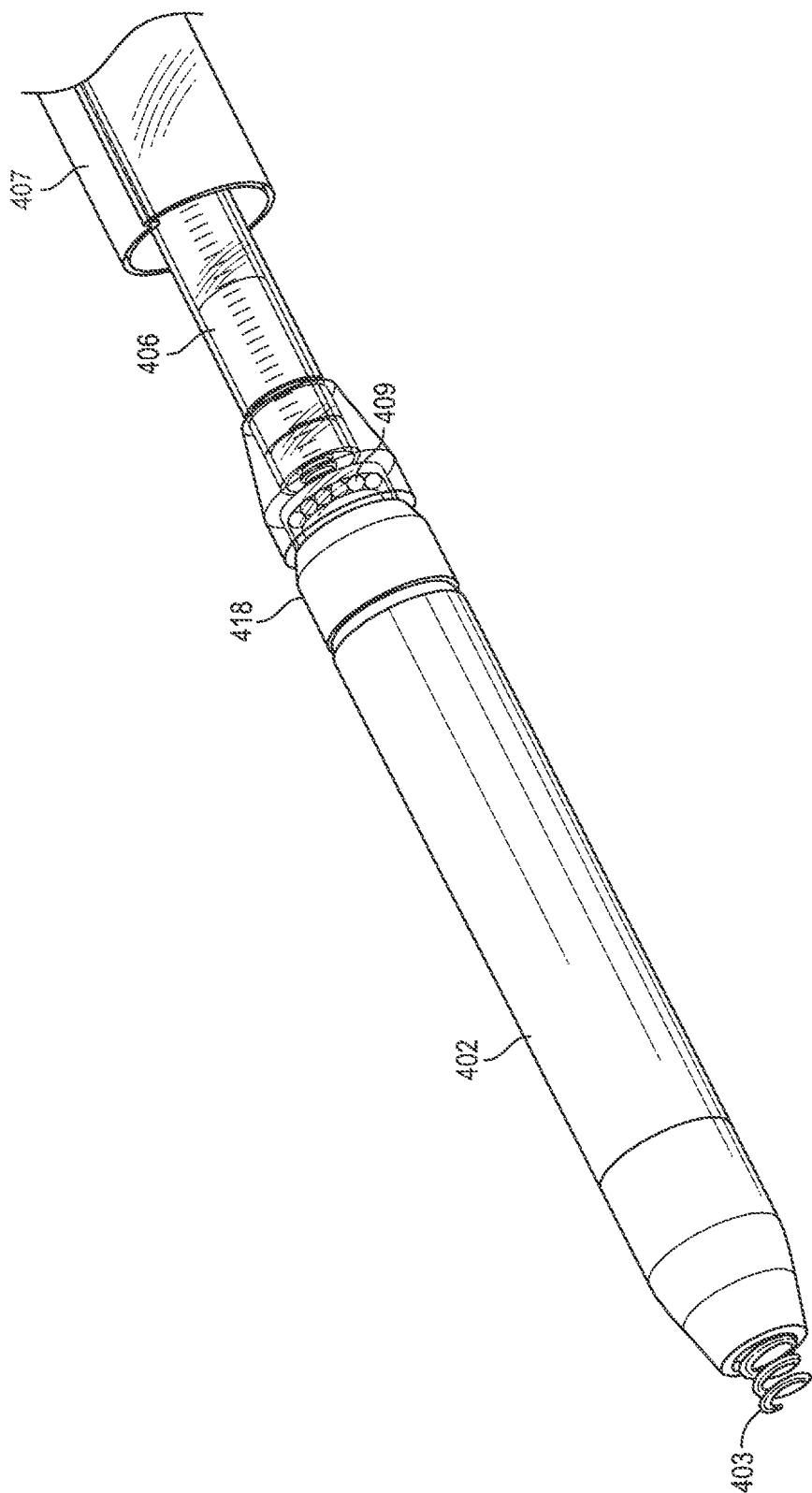

Still referring to FIGS. 4C and 4D, the docking cap 418 of the delivery catheter can include a torque slot 430 (shown in FIG. 4C) sized and configured to mate with a torque key 432 (shown in FIG. 4D) disposed on a proximal end of the pacemaker. The torque slot 430 can be coupled to a torque shaft 431, which runs the length of the delivery catheter extending into the handle (not shown). In FIGS. 4C and 4D, torque key 430 is shown as a "male" key and torque slot 430 is shown as a "female" key, but it should be understood that in other implementations, the "male" key can be located on the attachment feature 418, and the "female" key can be disposed on the pacemaker. It should also be appreciated that key 432 and slot 430 can include any number of shapes, such as square, rectangle, triangle, pentagon, hexagon, cross, "X", etc., so long as key 432 fits within and can apply rotational torque to slot 430. Once the tethers are locked within the attachment feature, the tethers can be pulled proximally to pull attachment feature 424 and the pacemaker towards the catheter and to attach the pacemaker to the delivery catheter, thereby engaging torque slot 430 with torque key 432 (as shown in FIG. 4G).

Figure 5A:
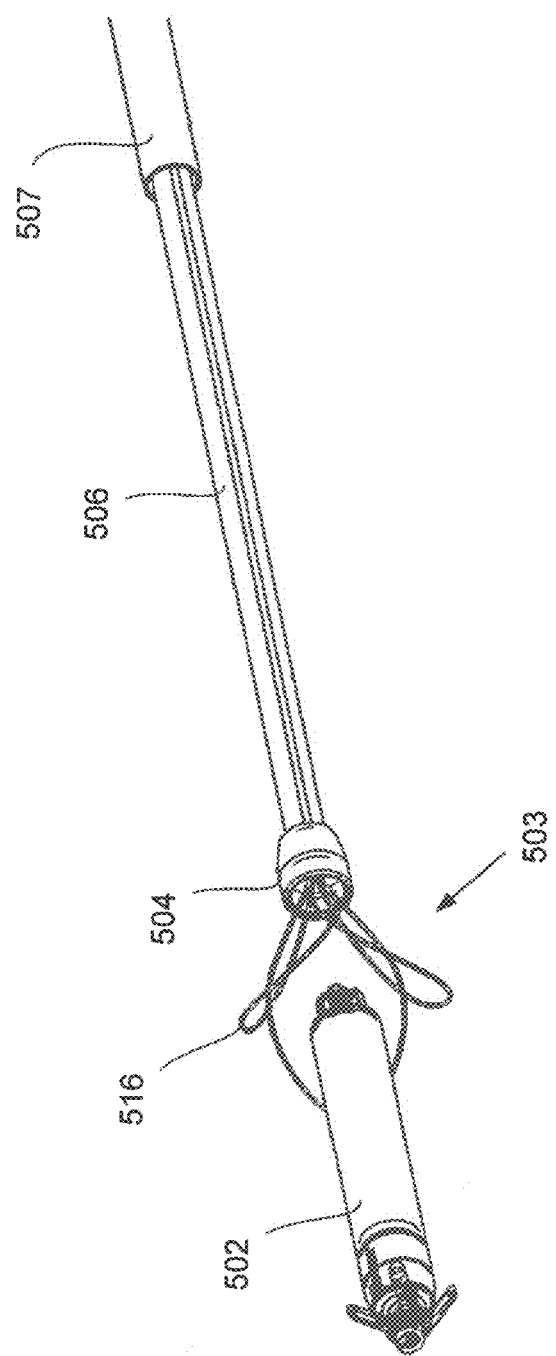

FIG. 5A illustrates a close-up view of one embodiment of a distal portion of the system 100 shown in FIG. 1 as used for retrieval of a leadless pacemaker 502. The distal portion of the retrieval catheter can include a snare 503 configured to grasp a leadless cardiac pacemaker or other medical device, and a docking cap 504 configured to allow docking of the leadless pacemaker 502 with the retrieval catheter after engaging the pacemaker 502 with the snare 503. FIG. 5A also illustrates a catheter shaft 506 terminating at the docking cap 504, and a protective sheath 507 positioned along the catheter shaft 506 slightly proximal to the docking cap 504 and the leadless pacemaker 502.

As shown in FIG. 5A, the snare 503 can include at least one loop 516 extending from the catheter shaft 506. As the snare 503 is advanced distally out of the system 100 from the docking cap 504, the loops 516 can expand in size to aid a user in positioning the snare 503 around or in proximity to the pacemaker 502 to be retrieved. In some implementations, as in FIG. 5A, the snare 503 can include multiple loops, such as three loops. However, any number of loops can be used as long as the catheter shaft contains sufficient volume to accommodate the loops.

Figure 5B:
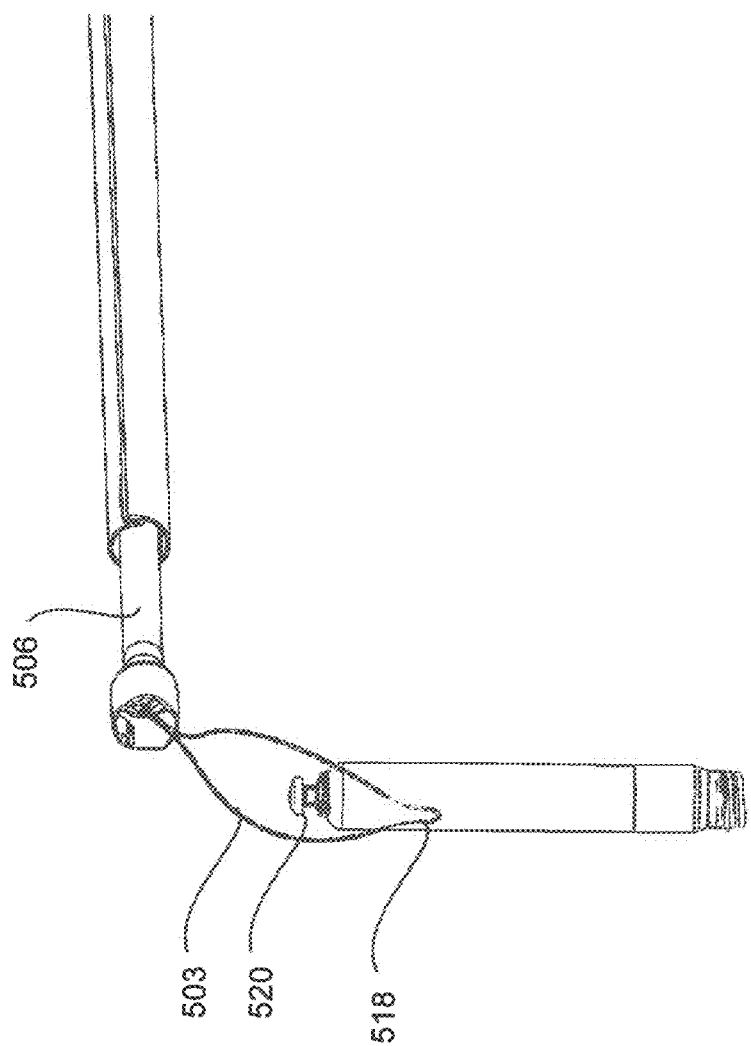

In another embodiment, as shown in FIG. 5B, the snare can include only a single loop. Also shown in FIG. 5B, the loops can include any number of features 518 to aid in grasping a pacemaker or medical device for retrieval. In FIG. 5B, the feature 518 can include, for example, a notch feature. In some implementations, the loops of the snare can be positioned off axis from the center of the catheter shaft to aid in keeping the pacemaker in line with the catheter during removal. For example, in FIG. 5B, the single loop snare 503 can include a notch feature 518 and be positioned off axis from the longitudinal axis of the catheter shaft 506. Since the snare is off axis from the catheter, the snare 503 can be looped around a retrieval feature 620 of the pacemaker by positioning the catheter adjacent to the pacemaker and allowing the loop to come into contact with the housing of the pacemaker. As the catheter is pulled away from the pacemaker, the snare 603 can slide up the pacemaker, and the notch feature 518 can be allowed to engage the retrieval feature 520 of the pacemaker.

FIG. 5C illustrates the snare 503 grasping a retrieval feature 520 of the leadless cardiac pacemaker 502. In the illustrated embodiment, a snare locking sleeve 505 can be advanced distally over the snare from the docking cap 504 of the catheter. As the snare locking sleeve 505 advances distally along the snare 503, it can cause the loops of the snare 503 to reduce in size, thereby grasping or locking onto the retrieval feature 520 of the pacemaker 502. In some implementations, the snare locking sleeve 505 can also include a torque shaft that runs through the length of the catheter. Details of the torque shaft will be described in more detail below, but generally the torque shaft can be rotated independently of the catheter shaft and coupled to the docking cap 604 of the catheter to apply rotational torque to the docking cap, and thus, to a pacemaker or medical device to be retrieved. In implementations where the snare 503 includes a plurality of loops, it may be more likely that one of the loops will grasp the pacemaker than in implementations where the snare 503 includes only a single loop.

Following capture and locking of the snare 502 with the leadless pacemaker 502, the leadless pacemaker may be docked within the docking cap 504. As previously discussed, FIG. 4G illustrates a delivery system in which a leadless pacemaker 402 is retained in a docked position. The configuration illustrated in FIG. 4G may be substantially similar to a configuration in which the leadless pacemaker 402 is docked with a docking cap 418 of a retrieval system. Accordingly, in addition to illustrating docking in a delivery system, FIG. 4G may also be interpreted to illustrate a close-up view of a distal portion of a retrieval catheter with a snare locked onto a retrieval feature (not shown) of the leadless pacemaker 402 and docked within docking cap 418. In some implementations, as will be described in more detail below, the docking cap 418 can include a key or interference feature configured to mate with and engage a corresponding key or feature on the pacemaker 402. In some implementations, the key or slot on the docking cap 418 can match a unique shape or feature of the retrieval feature of the pacemaker 402. Because the key or slot on or in the docking cap 418 can mate with and engage the key or slot on the pacemaker, the retrieval catheter can be configured to apply torque to the pacemaker to unscrew and remove the pacemaker from tissue. FIG. 4G also illustrates a protective sheath 407 positioned slightly proximally to the docking cap 418 along the catheter shaft of the retrieval system.

As shown in FIG. 4G, the docking cap 418 can include ball bearings 409 which allow the docking cap to be free-rotating from the rest of the catheter shaft. This effectively reduces the removal torque and additional forces from the catheter body. The docking cap 418 can be selectively coupled to a torque shaft (not shown) that extends through the length of the catheter to a torque knob on the handle (described below) or other rotatable portion of the handle coupled to the torque shaft. When the torque shaft is coupled to the docking cap 418, rotation or actuation of the torque knob rotates the torque shaft, thereby rotating the docking cap 418 at the end of the retrieval catheter. In some implementations, the docking cap 418 can include a keyed portion or interference feature so as to apply additional torque to the pacemaker when unscrewing.

Referring back to FIG. 2B, a protective sheath 204 is shown disposed over a leadless cardiac pacemaker and positioned at the distal end of guide catheter shaft 211. As described above, the protective sheath can be configured to slide over the pacemaker to prevent any sharp edges or features of the pacemaker from tearing, damaging, or catching onto tissue during removal of the pacemaker. The protective sheath can be slidable along a longitudinal axis of the catheter so as to allow for covering and uncovering of the pacemaker with the sheath. In some implementations, the protective sheath can include other form factors than illustrated in FIG. 2B. For example, in some retrieval scenarios where vegetative growth over the device is significant, the protective sheath may be of a larger diameter to accommodate the increase in size of the device.

The above description of FIGS. 5A-5C can be used to illustrate one embodiment of a method of retrieving a medical device or leadless cardiac pacemaker from a patient. First, a retrieval catheter can be advanced into a patient until the docking cap of the catheter is in the vicinity of the pacemaker. Next, the snare of the retrieval catheter can be advanced distally outward from the catheter to surround the retrieval feature of the pacemaker. Once the snare is surrounding the retrieval feature of the pacemaker, the snare locking sleeve/torque shaft can be advanced distally along the snare to close the snare, causing the snare to grasp the retrieval feature of the pacemaker. Next, the snare and snare locking sleeve can be pulled proximally towards the docking cap of the catheter so as to engage the proximal end or retrieval feature of the pacemaker. Rotational torque can then be applied by the catheter to the pacemaker via the torque shaft and docking cap to unscrew the pacemaker from the tissue. The protective sheath can be advanced over the pacemaker, and the pacemaker can then be removed from the patient.

FIGS. 6-8B show multiple views of various implementations of retrieval features on a leadless cardiac pacemaker. The retrieval features illustrated in these figures can be grasped by the snare of the retrieval catheters described herein, and can also be configured to dock within the docking cap of the retrieval catheter.

Figure 6:
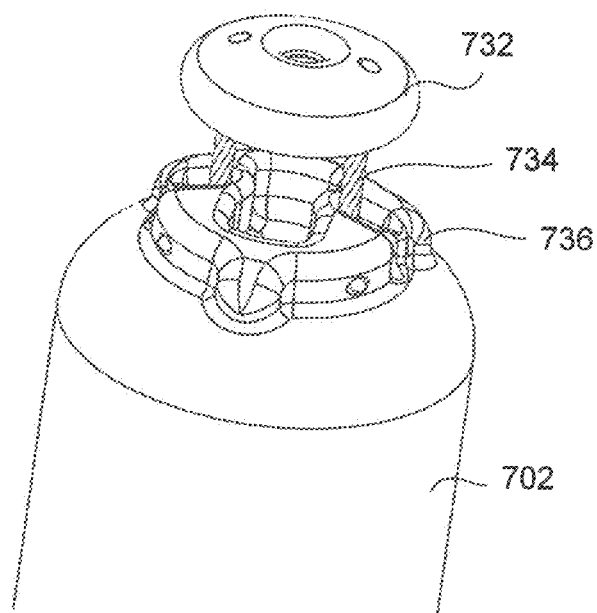
FIGS. 6-7 are various views of one embodiment of a pacemaker having a retrieval feature.
Figure 7:
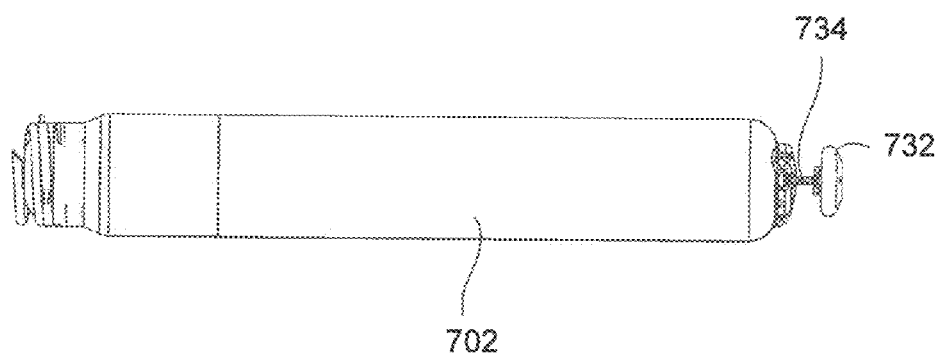

In FIGS. 6-7, the retrieval feature includes a "button" or circular grasping feature 732. The grasping feature 732 can be attached to the pacemaker 702 via at least one flexible stem 734. The flexible stem allows for easier capturing of the pacemaker into the docking cap by allowing the grasping feature and stem(s) to "bend" into the docking cap when the retrieval catheter is off-axis from the pacemaker during a retrieval attempt. The flexible stem(s) also allow the grasping feature 732 to orient itself within the snare and to compensate for the asymmetry of the snare to allow it to align the docking cap with the pacemaker. Additionally, the flexible stem deflection permits torque transmission from the catheter to the leadless pacemaker. The flexible stem can be made of materials such as nitinol, stainless steel or titanium cable, MP35N, or other similar materials. The flexible stem may be connected to the grasping feature and the proximal end of the leadless pacemaker by laser welding, soldering, or other manufacturing processes know in the art.

Also shown in FIG. 6, a proximal portion of the pacemaker 702 can include a key feature 736. The key feature 736 can be sized and configured to mate with the interference feature within the docking cap, as described above. The key feature of the pacemaker and the interference feature of the docking cap and catheter can allow the torque shaft and docking cap of the catheter to apply rotational torque to the pacemaker, such as to unscrew the pacemaker from tissue during retrieval.

Figure 8A:
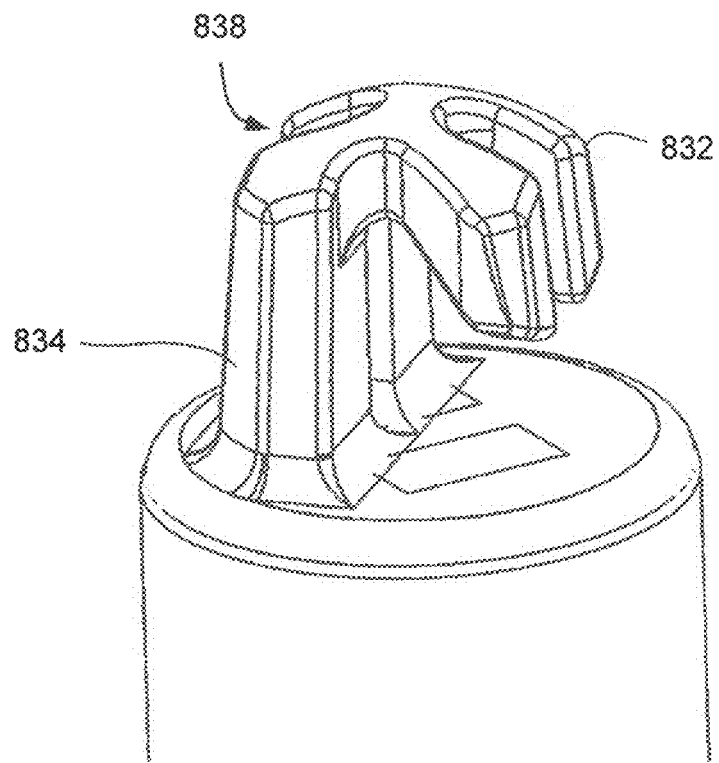
FIGS. 8A-8B are various views of another embodiment of a pacemaker having a retrieval feature.
Figure 8B:
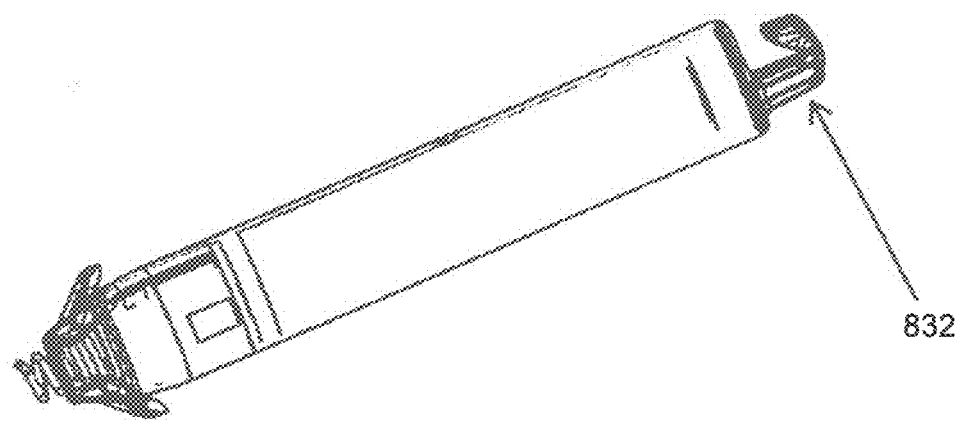

FIGS. 8A-8B illustrate another embodiment of a "hook shaped" retrieval feature 832 on the pacemaker 802. The hook shaped proximal cap can allow for easier grasping by the snare. The "hook shaped" retrieval feature can provide an easily accessible yet atraumatic surface for the snare to grasp. In some implementations, a base portion 834 of the hook shaped feature can include a flexible material, as described above with respect to the flexible stems of the "button" shaped retrieval feature in FIGS. 6-7. The hook shaped retrieval feature can also include cutouts 838 that can serve a similar purpose to the key feature described above in FIGS. 6-7. The cutouts can engage, for example, similarly shaped features in the docking cap or retrieval catheter to allow the catheter to apply rotational torque to the pacemaker for unscrewing the pacemaker from tissue.

As described above, the docking cap itself can include cutouts or recessed slots configured to mate with or engage the retrieval feature of the pacemaker. For example, the circular retrieval feature of FIGS. 6-7 can mate with a similarly shaped recessed slot within the docking cap. Similarly, the hook shaped retrieval feature of FIGS. 8A-8B can mate with a similarly shaped recessed slot within the docking cap.

B. Catheter Delivery System Handle Including Deflection Lever and Lever Brake Systems Catheter delivery and retrieval systems including catheters having deflectable or steerable tips generally include a mechanism on a handle that actuates or otherwise causes the deflection of the catheter tip. In general, such mechanisms include a pull wire coupled to each of the mechanism and the deflectable tip such that actuation of the mechanism pulls the pull wire, thereby causing deflection of the tip.

Conventional actuation mechanisms for deflectable tips have various disadvantages and shortcomings. First, such conventional mechanisms offer little to no mechanical advantage such that the user must exert a force on the actuation mechanism that is substantially equal to the force required to deflect the catheter tip. Such forces may result in excess fatigue during lengthy procedures and/or may be difficult to use with larger catheters or by users with relative small hands. Second, many conventional deflection mechanisms require two hands to operate. Finally, operation of many conventional deflection mechanisms is not intuitive or immediately apparent from the appearance of the mechanism.

In light of the foregoing, the present disclosure provides delivery and retrieval systems having deflectable catheters and that further include improved actuation and locking mechanisms.

In one embodiment, the delivery and retrieval system includes a handle and a lever extending from the handle. The lever is coupled to a hub that is in turn coupled to a deflectable catheter tip by a pull wire. By depressing the lever against the handle, the hub may be rotated, oil/ling the pull wire and deflecting the catheter tip. In certain implementations, the handle may further include a braking or locking mechanism that may be actuated to lock the hub in position or otherwise increase resistance to further rotation or counter-rotation of the hub. In certain implementations, the deflection lever disclosed herein provides significant mechanical advantage such that the input force required to be exerted by a user is reduced relative to the force exerted by the mechanism on the pull wire. For example, in certain implementations the force required to move the deflection lever may be approximately thirty to fifty percent of the force required to move the deflectable catheter directly.

FIGS. 9A-9B are top views of an embodiment of a handle 900 of a delivery and/or retrieval system, such as the system 100 of FIG. 1D. The handle 900 includes a housing 902 into which a deflectable catheter 50 is inserted. The deflectable catheter includes a deflectable section 51 which may correspond to a tip section of the deflectable catheter 50. In other implementations, the deflectable section 61 may instead correspond to a different section of the deflectable catheter 50 proximal the tip section.

The handle 900 includes a deflection lever 904 extending from the housing 902. In FIG. 9A, the deflection lever 904 is shown in an extended position. The extended position generally corresponds to a resting position of the deflection lever 904, such as when no external force is applied to the deflection lever 904. In the resting position, the deflectable section 51 of the deflectable catheter 60 is in a resting position, which in the example of FIG. 9A is a substantially straight configuration. In contrast to FIG. 9A, FIG. 9B illustrates the deflection lever 904 in a depressed position. As the deflection lever 904 is transitioned between the extended and depressed positions, the deflectable section 51 transitions between the resting configuration illustrated in FIG. 9A and the deflected configuration illustrated in FIG. 9B, which in the current example, is a ninety degree deflection in the direction of the deflection lever 904. Accordingly, the deflection lever 904 may be partially depressed in order to achieve configurations of the deflectable section 51 intermediate to those illustrated in FIGS. 9A-9B.

Figure 10A:
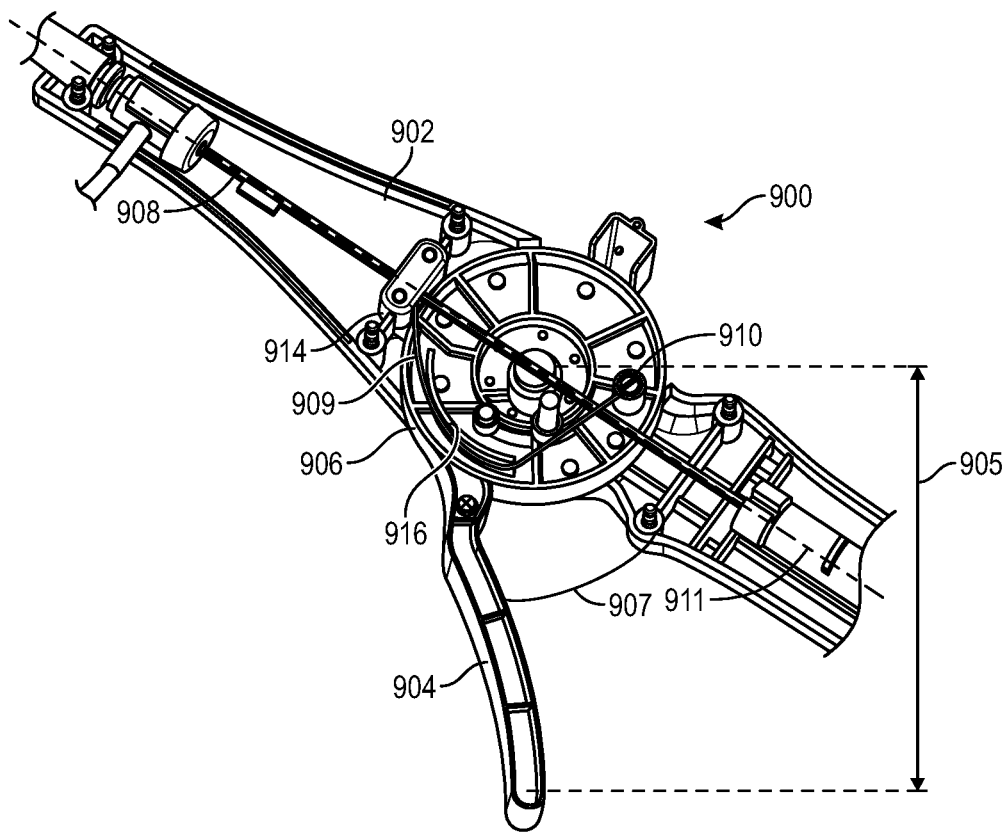
FIGS. 10A-10B are isometric bottom views of the handle of FIGS. 9A-9B, respectively, with a housing portion removed.
Figure 10B:
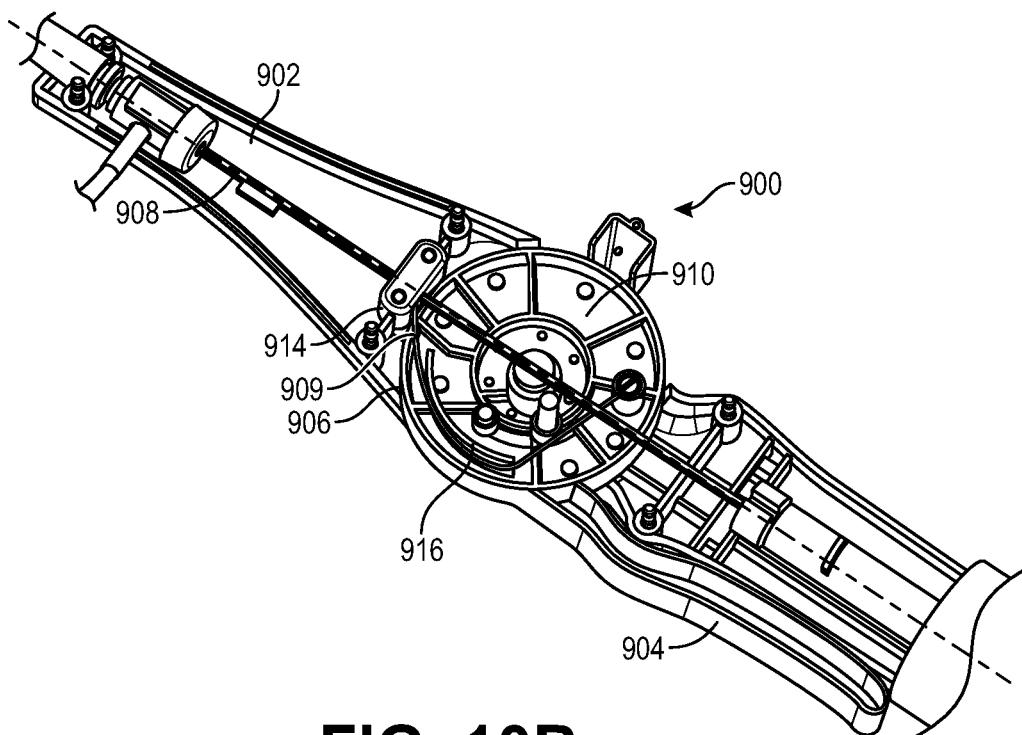
Figure 10C:
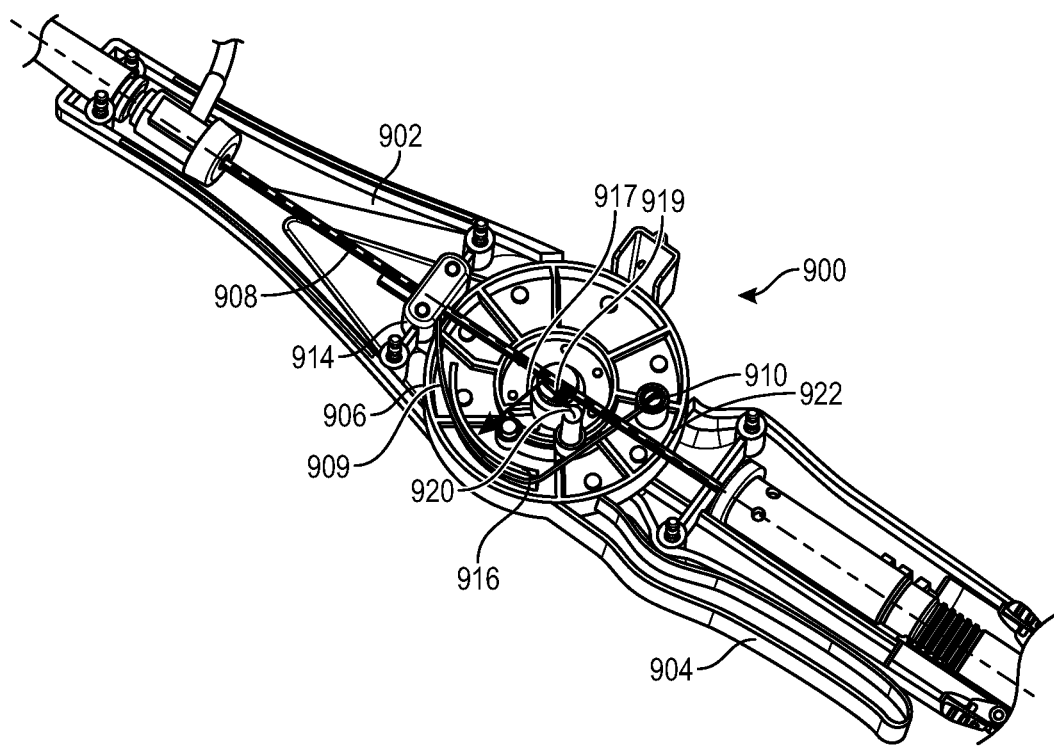
FIG. 10C is a bottom view of the handle of FIG. 9B with a housing portion removed.

FIGS. 10A-10C are bottom views of the handle 900 with a portion of the housing 902 removed to show internal components within the handle 900. FIGS. 10A and 10B, for example, illustrate the handle 900 with the deflection lever 902 in an extended and depressed configuration, respectively, which generally correspond to the extended and depressed configurations illustrated in FIGS. 9A-9B.

The length of the lever 904 may be varied to modify the degree of mechanical advantage provided by the lever 904 to cause deflection of the deflectable catheter. Referring to FIG. 10A, for example, the lever 904 may define a moment arm 905 extending from the center of the hub 906 to the end of the lever 904. In certain implementations, the moment arm 905 is from and including 3.00 inches and including 4.00 inches. For example, in one specific implementation, the moment arm 905 is 3.50 inches. The lever 904 may also extend from the hub 906 at a predetermined angle 907 relative to a longitudinal axis 911 of the handle 900 when the lever 904 is in the extended position. In certain implementations, the angle 907 is from and including 50 degrees to and including 60 degrees. For example, in one implementation, the angle is 57 degrees. Also, full depression of the lever 904 may result in a predetermined rotation of the hub 906. For example, in certain implementations, movement of the lever 904 from the extended position (as illustrated in FIG. 10A) to the depressed position (as illustrated in FIG. 10B) may result in rotating the hub 906 from and including 35 degrees to and including 50 degrees. For example, in certain implementations movement of the lever 904 from the extended position to the depressed position may rotate the hub 906 approximately 45 degrees.

As shown in FIGS. 10A-10C, the deflection lever 904 may be coupled to a hub 906 supported within the housing 902 that rotates within the housing 902 in response to depression of the deflection lever 904. A fiber 909 couples the hub 906 to a pull wire 908 extending from the deflectable section 51 of the deflectable catheter 50 (shown in FIGS. 9A-9B) that, when pulled, causes deflection of the deflectable section 51.

In general, the fiber 909 is coupled to the hub 906 at an anchor 910, which may include a press pin 912, set screw, or similar fixation mechanism for fixing the fiber 909 relative to the hub 906. The housing 902 and the hub 906 may also include additional structural elements for routing and supporting the fiber 909. For example, the housing 902 may include a roller 914 over which the fiber 909 is routed to reduce friction. The hub 906 may also include one or more curved or arced walls 916 over which the fiber 909 is wrapped. In certain implementations, the total travel of the fiber 909 and, by extension, the pull wire 908 is increased by having the fiber 909 wrap around the outside of the arced walls 916 as opposed to following a straight line between the roller 914 and the anchor 910. In certain implementations, the arced wall 916 may be disposed at a radius from and including 0.600 inches to and including 0.900 inches and have an arc length from and including 0.350 inches to and including 0.550 inches. For example, in one implementation, the arced wall 916 may be disposed at a radius of 0.787 inches and have an arc length of approximately 0.484 inches.

Referring to FIG. 10C, the handle 900 may further include a multiplier post 920 about which the fiber 909 is wrapped. In certain implementations, for example, the multiplier post 920 may be coupled to the housing 902 and extend through a post cutout 922 defined by the hub 906. When the multiplier post 920 is used, the fiber 909 is routed around the arced walls 916 and further around the multiplier post 920 such that the path followed by the fiber 909 is a longer and more serpentine as compared to implementations in which the multiplier post 920 is absent or unused (such as illustrated in FIGS. 10A-10B).

Aspects of the hub 906 may conform to specific ranges of predetermined values. For example, in certain implementations, the arced wall 916 is disposed at a first radius 917 relative to the center of the hub 906. For example, the first radius 917 may be from and including 0.55 inches to and including 0.81 inches. The arced wall 916 may also extend along a predetermined arc length. In certain implementations, the predetermined arc length may be from and including 0.25 inches to and including 1.25 inches. Similarly, the multiplier post 920 may be disposed at a second radius 919 from and including 0.405 inches to and including 0.465 inches from the center of the hub 906.

Referring now to FIGS. 11A-11B, the handle 900 may further include a brake assembly 950 disposed opposite the deflection lever 902. In certain implementations, the brake assembly 950 may include a knob 952 from which a brake lever 954 extends. During operation, the brake assembly 950 may be actuated to increase resistance to rotation of the hub 906 and the deflection lever 902 coupled thereto. More specifically, by applying a force to the brake lever 954, the knob 952 may be rotated such that the brake assembly 950 is movable between a first position, shown in FIG. 11A, in which a low resistance (including no resistance) is applied to the hub 906 and a second position, shown in FIG. 11B, in which a high resistance is applied to the hub 906. Although shown as being moved between the first and second positions when the deflection lever 902 is in the depressed position, the brake assembly 950 may be actuated when the deflection lever 902 is disposed in any position. By doing so, the deflection lever 902 may be held by the brake in an intermediate position and, by extension, the deflection section 51 may be held in a partially deflected configuration. In certain implementations, movement of the brake assembly 950 between the first and the second positions includes rotating the knob 950 from and including 0 degrees to and including 65 degrees.

Figure 12:
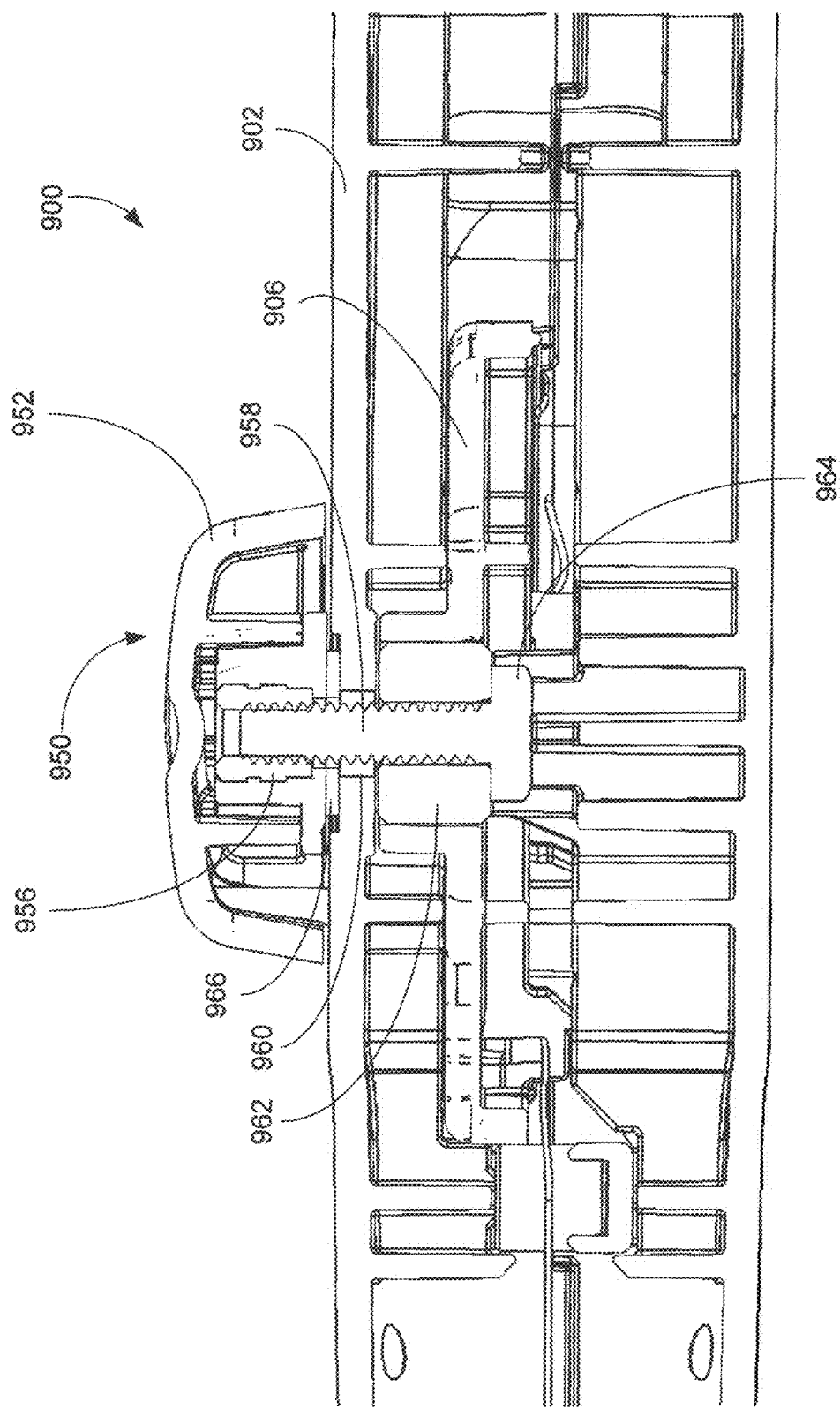
FIG. 12 is a cross-sectional side view of the brake assembly of FIGS. 11A-11B.

FIG. 12 is a cross-sectional view of the handle 900 including the brake assembly 950. In certain implementations, the brake assembly 950 may include a threaded insert 956 coupled to the knob 952 and threadedly coupled to a threaded shaft 958. The threaded shaft 958 extends through an exterior brake washer 966, a hole 960 defined by the housing 902, and an unthreaded hub washer 962 and terminates in a shaft end 964 that is rotationally fixed within the housing 902. The washer 962 is disposed within the hub 906 and is rotationally fixed relative to the hub 906. For example, in certain implementations, the washer 960 may be a hexagonal washer 962 and may be disposed within a hexagonal hole or receptacle 964 defined by the hub 906.

As previously discussed, a braking force applied by the brake assembly 950 and the resulting resistance to rotation of the deflection lever 904 and the hub 906 may be adjusted by rotating the brake assembly 950 and, more specifically, the knob 952 by moving the brake lever 954. In the implementation illustrated in FIG. 12, the braking force/resistance is a result of friction caused by compression of the exterior wall 960 between the brake washer 966 and the hub washer 962. For example, when increasing the braking force/resistance, rotation of the knob 952 causes threaded translation of the threaded insert 956 towards the shaft end 962 of the threaded shaft 958. As a result of the translation, the exterior wall 960 is compressed between the brake washer 966 and the hub washer 962. This compression increases the frictional force on the hub washer 962 and, as a result, the resistance to rotation of the hub 906 as a result of the hub washer 962 being rotationally fixed relative to the hub 906. By varying the degree to which the knob 952 is rotated, the compressive force applied to the exterior wall 960 and the resulting frictional force on the hub washer 962 may be modified as required by the user.

In certain implementations, the knob 952 may be rotated into an intermediate position between the first position (as illustrated in FIG. 11A) and the second position (as illustrated in FIG. 11B). In such an intermediate position, a corresponding intermediate resistance is applied to the hub 906 such that a reduced amount of force is required by the user of the handle 900 to maintain the hub 906 in its current position. So, if a user anticipates that some but relatively infrequent movements of the hub 906 are required but that the hub 906 will primarily be held static, an intermediate resistance may be applied using the braking assembly 950 such that the user is still able to rotate the hub 906 if needed but the overall force required to maintain the position of the hub 906 is reduced.

In certain implementations, the deflectable catheter 50 may be biased toward an undeflected position such that the handle 900 has a passive return feature. In such implementations, an intermediate position of the knob 952 may also be used to apply sufficient resistance to overcome the passive return of the deflectable catheter 50 without otherwise preventing deflection by movement of the lever 904.

The handle 900 illustrated in the example implementations of FIGS. 9A-9B and 11A-11B is shown in a primarily right-handed configuration. When operated using the right hand, the user grips the handle 900 in an overhand grip such that the user's thumb extends in the direction of the catheter 50. When gripped in this manner, the user is able to readily squeeze the handle 904 with his or her fingers and manipulate the brake assembly 950 with his or her thumb. Moreover, the general layout of the handle 900 with the handle 904 extending away from the user results in an intuitive design in which a user is more likely to inherently understand that depressing the lever 904 results in deflection of the tip 51 away from the user. Such intuition is further reinforce in certain implementations by the presence of flush ports (such as the flush ports 114a-114c shown in FIG. 1D) which generally extend away from the user.

Although the handle 900 is shown in a configuration intended for use with an overhanded right hand grip, the handle 900 may nevertheless be operated using other grips including an underhand right hand grip and either an over- or underhand left hand grip. For example, in an underhand left handed grip, the user's thumb would still be directed towards the catheter 50 such that the user can readily manipulate each of the handle 904 and the brake assembly 950 using one hand. With an underhand right hand grip or an overhand left hand grip, the user may still be able to depress the lever 904, however, the user may require their other hand or an assistant to manipulate the brake assembly 950.

In still other implementations, a configuration intended for use with an overhand left hand grip may be achieved by flipping the lever 904 such that the lever 904 extends in the distal direction. In such implementations, depression of the lever 904 would cause the hub 906 to rotate in the opposite direction as in the implementation illustrated in FIGS. 9A-9B. Accordingly, to maintain proper tensioning of the deflectable tip, the fiber wire 909 adapted to pull the deflectable tip may be coupled to the top side of the hub 906 as opposed to the bottom side of the hub 906 as illustrated in FIGS. 10A-10C. The arced wall 916 and multiplier post 920 could also extend from the top of the hub 906 in such implementations. The brake assembly 950 may also be reverse threaded such that that increasing the resistance provided by the brake assembly 950 is achieved by rotating the brake lever 954 in a counterclockwise direction, opposite that illustrated in FIGS. 11A-11B.

The foregoing are merely examples of ways in which the handedness of the handle 900 may be modified in order to accommodate a left- or right-handed user. Moreover, any of the foregoing examples may be substantially mirrored or otherwise modified in order to produce either a left- or right-handed configuration.

C. Catheter Delivery System Handle Including Adjustable Tensioning System

As previously described in the context of FIGS. 1A-1D, leadless pacemakers are anchored into the endocardium using one or more fixation mechanisms. Such fixation mechanisms may include, without limitation, one or more of a helical screw and tines extending from the distal end of the leadless pacemaker.

During delivery and implantation of a leadless pacemaker, firm coupling between the leadless pacemaker and the corresponding delivery system is required such that torque applied using the delivery system is transmitted to the leadless pacemaker. Firm coupling between the leadless pacemaker and a retrieval system is also critical in the event that the leadless pacemaker is to be subsequently relocated or removed from the patient. For example, during the intervening time period between implantation and retrieval, features of the leadless pacemaker may become encapsulated by tissue. In certain cases, for example, mating features of the leadless pacemaker may become partially or entirely encapsulated by tissue and the ability of a physician to couple a catheter of the retrieval system to the mating features may be compromised. As a result, torque transmission from the retrieval system to the leadless pacemaker may be poor and may result in an inability to retrieve the leadless pacemaker.

To address the foregoing issue, a tensioning assembly for use in a handle of a retrieval system is provided that allows a user to obtain and maintain tension on a captured and docked leadless pacemaker. As a result, the contact force between a docking cap or other distal feature of a retrieval catheter of the retrieval system is increased and torque transmission between a torque shaft of the retrieval system and the leadless pacemaker is improved as compared to conventional retrieval systems. The tensioning assembly is auto-locking, thereby preventing a user from accidentally losing grip on a leadless pacemaker once captured and, in particular, during unscrewing of the leadless pacemaker from the endocardium. In addition to the foregoing issues related to tissue encapsulation, the tensioning assembly described herein also accommodates variations in patient anatomy (such as, without limitation, variations in vascular bend angles) and variations in catheter system components.

By incorporating the tensioning assembly into the handle, a user is able to obtain and maintain a firm grip on the leadless pacemaker being retrieved. Moreover, if the retrieval catheter is slipping on the leadless pacemaker as the retrieval catheter during unscrewing of the leadless pacemaker from the endocardium or if the user notices a gap between the retrieval catheter and the pacemaker as a result of tissue or system variation, the user may readily increase tension on the leadless pacemaker. The auto-locking feature maintains tension on the leadless pacemaker and may further provide feedback to the user, such audible or tactile feedback, as tension is increased.

Tensioning assemblies in accordance with this disclosure generally include a handle having a pair of handle portions that are movable relative to each other and coupled by a ratchet mechanism. For example, in one implementation, the handle includes a first, outer handle portion within which a second, inner handle portion may be inserted and translated. The first handle portion includes a pawl that interacts with a rack surface of the second handle portion thereby forming a ratchet mechanism that couples the first handle portion to the second handle portion.

The second handle portion is coupled to a snare or similar retrieval feature such that as the second handle portion is proximally translated relative to the first handle portion, the retrieval feature is cinched or otherwise dosed, such as by retraction of the snare into a torque or retrieval catheter. As the second handle portion is translated, the ratcheting mechanism engages to ensure that tension is maintained on the retrieval feature even if the user releases his or her grip on the second handle portion or otherwise reduces tension applied to the second handle portion.

In certain implementations, the pawl of the first handle portion is coupled to and rotatable about a pin disposed within the first handle portion. In such implementations, the pawl may include a button extending through the housing of the first handle portion and may be biased, such as by a spring, into contact with the rack of the second handle portion. To release the pawl from the rack, a user may depress the button, thereby causing the pawl to rotate about the pin, disengaging the pawl from the rack, and allowing distal translation of the second handle portion relative to the first handle portion.

The rack of the second handle portion includes multiple teeth that extend around the circumference of the second handle portion. As a result, the second handle portion may be rotated relative to the first handle portion while tension is maintained on the snare by the ratchet mechanism.

Figure 13A:
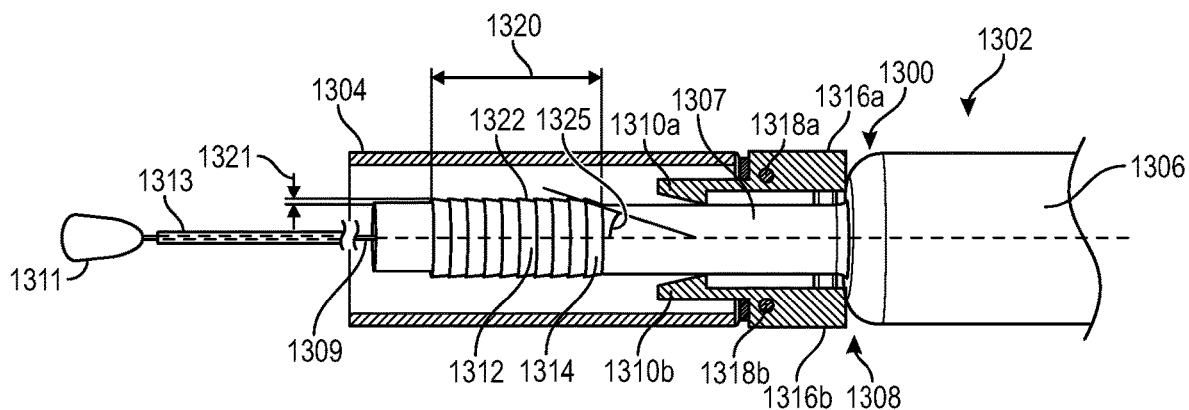
FIGS. 13A-13C are cross-sectional side view of a handle of a retrieval system including a first implementation of a tensioning assembly.
Figure 13B:
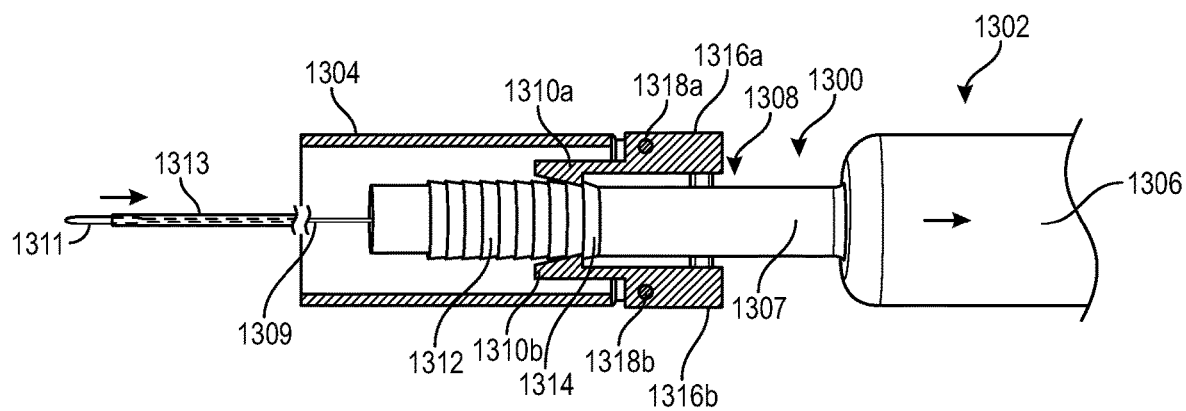
Figure 13C:
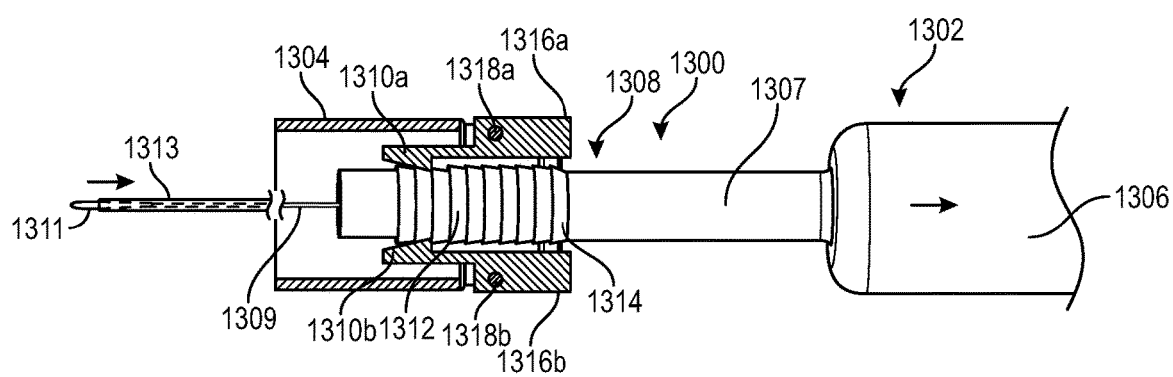

FIGS. 13A-13C are cross-sectional side views of one embodiment of a tensioning assembly 1300 for use in a retrieval system, such as the delivery and retrieval system 100 illustrated in FIG. 1D. The tensioning assembly 1300 is generally disposed within a handle 1302 of the retrieval system and couples a distal handle portion 1304 to a proximal handle portion 1306. As illustrated in FIGS. 13A-13C, the proximal handle portion 1306 includes a shaft 1307 that extends at least partially into the distal handle portion 1304. The proximal handle portion 1306 is coupled to a tensioning member 1309, such as a wire, that extends from the handle 1302 and to a distal end of the retrieval system where the tensioning member 1309 may be coupled to a snare, a tether, a lasso, or similar retrieval feature 1311 couplable to a corresponding retrieval feature of an implantable medical device, such as a leadless pacemaker.

The distal handle portion 1304 and the proximal handle portion 1306 are coupled together by a ratchet mechanism 1308 that includes one or more pawls 1310*a*, 1310*b* of the distal handle portion 1304 and a rack 1312 disposed on the shaft 1307. The rack 1312 includes multiple teeth, such as tooth 1314. As illustrated by the transition between FIGS. 13A-13C, the proximal handle portion 1306 may be translated proximally relative to the distal handle portion 1304 such that the pawls 1310 engage the teeth of the rack 1312.

During operation, a user of the retrieval system including the tensioning assembly 1300 loosely couples the retrieval feature 1311 to the implantable medical device. Once loosely coupled, the proximal handle portion 1306 is translated proximally which applies tension to the tensioning member 1309 and tightens the coupling between the retrieval system and the implantable medical device. For example, as illustrated in the transition from FIG. 13A to FIG. 13C, increasing tension on the tensioning member 1309 may cinch or otherwise tighten the retrieval feature 1311. For example, as illustrated in FIGS. 13A-13C, the retrieval feature 1311 may be disposed and translatable within a catheter shaft 1313, the catheter shaft 1313 being coupled to a distal handle portion 1304 or other portion of the handle fixed relative to the proximal handle portion 1306. Accordingly, as the proximal handle portion 1306 is translated proximally relative to the distal handle portion 1304, the retrieval feature 1311 is similarly translated proximally such that the retrieval feature 1311 is drawn into the catheter shaft 1311. By further translating the proximal handle portion 1306, the retrieval feature 1311 is further drawn into the catheter shaft 1313. Alternatively, if an object, such as an attachment feature of a leadless pacemaker, is retained within the retrieval feature 1311, further translation of the proximal handle portion 1306 causes the retrieval feature to dose more tightly around the object, increasing tension on the tensioning member 1309.

The pawls 1310*a*, 1310*b* and the teeth 1314 are shaped such that when the proximal handle portion 1306 is sufficiently translated in the proximal direction, the pawls 1310*a*, 1310*b* engage the teeth 1314 of the rack 1312 due to the pawls 1310*a*, 1310*b* being biased into engagement with the rack 1312. The rack 1312 defines a locking region of the tensioning assembly 1300 due to the ratcheting mechanism 1308 and, more specifically, by the shape and arrangement of the teeth 1314. Accordingly, once the pawls 1310*a*, 1310*b* engage the teeth 1314 of the rack 1312, subsequent distal translation of the proximal handle portion 1306 relative to the distal handle portion 1304 is resisted or prevented. However, as illustrated by the transition from FIG. 13B to FIG. 13C, the proximal handle portion 1306 may be further translated in a proximal direction, thereby applying further tension on the tensioning member 1309. Such further tensioning of the tensioning member 1309 may be required to overcome one or more sources of variation that can impact the contact/grip force between the catheter retrieval system and the implantable medical device and ultimately torque transmission between the catheter retrieval system and the implantable medical lead. For example, such sources of variation may include, without limitation, variations in patient anatomy resulting in varying bend and approach angles, the severity of tissue encapsulation on coupling features of the implantable medical device, and variations in the shape and properties of components of the catheter retrieval system.

The pawls 1310*a*, 1310*b* may include respective buttons 1316*a*, 1316*b* adapted to disengage the pawls 1310*a*, 1310*b* from the rack 1312 when depressed, thereby allowing distal movement of the proximal handle portion 1306 relative to the distal handle portion 1304. For example, the pawls 1310*a*, 1310*b* of FIGS. 13A-13C include buttons 1316*a*, 1316*b* that, when depressed, cause the pawls 1310*a*, 1310*b* to rotate about respective mounting pins 1318*a*, 1318*b* by which the pawls 1310*a*, 1310*b* are coupled to the distal handle portion 1304. In certain implementations, the mounting pins 1318*a*, 1318*b* may be mechanically pressed or free floating within the distal handle portion 1304 and varying the location of the mounting pins 1318*a*, 138B within the distal handle portion 1304 may vary the degree of mechanical advantage when the buttons 1316*a*, 1316*b* are depressed. Rotation of the pawls 1310*a*, 1310*b* about the mounting pins 1318*a*, 1318*b* disengages the pawls 1310*a*, 1318*b* from the teeth 1314 of the rack 1312, thereby enabling distal translation of the proximal handle portion 1306.

The buttons 1316*a*, 1316*b* may be one of flush with, protruding from, or recessed relative to the distal handle portion 1304. In certain implementations, the position of the buttons 1316*a*, 1316*b* relative to the distal handle portion 1304 may vary depending on whether the pawls 1310*a*, 1310*b* are engaged with or disengaged from the rack 1312. For example, in one implementation, the buttons 1316*a*, 1316*b* may be recessed prior to proximal movement of the proximal handle portion 1304 that engages the ratchet mechanism 1318. However, after engagement, the buttons 1316*a*, 1316*b* may protrude from the distal handle portion 1304 to facilitate depression of the buttons 1316*a*, 1316*b*. The relative position of the buttons 1316*a*, 1316*b* to the distal handle portion 1304 may be controlled by, among other things, the size and the shape of the pawls 1310*a*, 1310*b*, the depth and shape of the teeth 1314 of the rack 1312, and the position of the mounting pins 1318*a*, 1318*b* about which the pawls 1310*a*, 1310*b* rotate.

As illustrated in FIGS. 13A-13C, the rack 1312 may extend about the circumference of the shaft 1307 such that the proximal handle portion 1306 may be rotated without disengaging the pawl 1310 from the rack 1312. As a result, a user may rotate the proximal handle portion 1306 to unscrew the leadless pacemaker or similar Implantable medical device without compromising the coupling between the retrieval system and the implantable medical device. Also, during unscrewing of the implantable medical device, if the user notices a loosening of the coupling to the implantable medical device, the user may simply translate the proximal handle portion 1306 in the proximal direction to apply further tension without modifying the rotational position of the proximal handle portion 1306 relative to the distal handle portion 1304.

In certain implementations, the ratchet mechanism 1308 may be configured to provide tactile and/or audible feedback to a user of a retrieval system implementing the tensioning assembly 1300. Such feedback may come in the form of an audible click or tactile bump as the proximal handle portion 1306 is translated proximally and the pawls 1310 engage successive teeth 1314 of the rack 1312.

The performance characteristics of the tensioning assembly 1300 may be modified by, among other things, adjusting aspects of the rack 1312 including, without limitation, the quantity, spacing, and geometry of the teeth 1314. For example, the quantity of teeth 1314 and length of the rack 1312 may be adjusted to accommodate expected amounts of variation based on the operation undertaken using a retrieval system including the tensioning assembly 1300. Spacing between adjacent teeth of the rack 1312 may also be modified to change the resolution by which the tension applied and maintained by the tensioning assembly 1300 may be modified. The angle of the teeth 1314 of the rack 1312 may also be modified to vary the resistance provided by the rack 1312 against proximal translation of the proximal handle portion 1306. For example, each tooth 1314 may have a ramped tooth surface 1322 that forms an angle 1325 relative to a longitudinal axis of the shaft 1308. The angle 1325 may be increased or decreased to impart a corresponding change in the resistance provided by the rack 1312 to proximal translation of the proximal handle portion 1306. Although shown in FIG. 13 as having a linear ramped tooth surface 1322, in other implementations, each tooth 1314 may instead have a contoured or curved profile to further vary the resistance profile provided as the proximal handle portion 1306 is translated.

Referring to FIG. 13A, the rack 1312 may have a rack length 1320 corresponding to a length of the shaft 1308 over which the rack 1312 extends. In certain implementations, the rack length 1320 may be from and including 0.08 inches to and including 1.25 inches. The rack 1312 may also have a tooth density from and including 13.33 teeth per inch to and including 5 teeth per inch. Each of the teeth 1314 may have a tooth height 1321 from and including 0.02 inches to and including 0.07 inches. Each tooth may also have a ramped tooth surface 1322 forming an angle 1325 from and including 10 degrees to and including 75 degrees relative to a longitudinal axis 1324 of the shaft 1308.

Figure 14A:
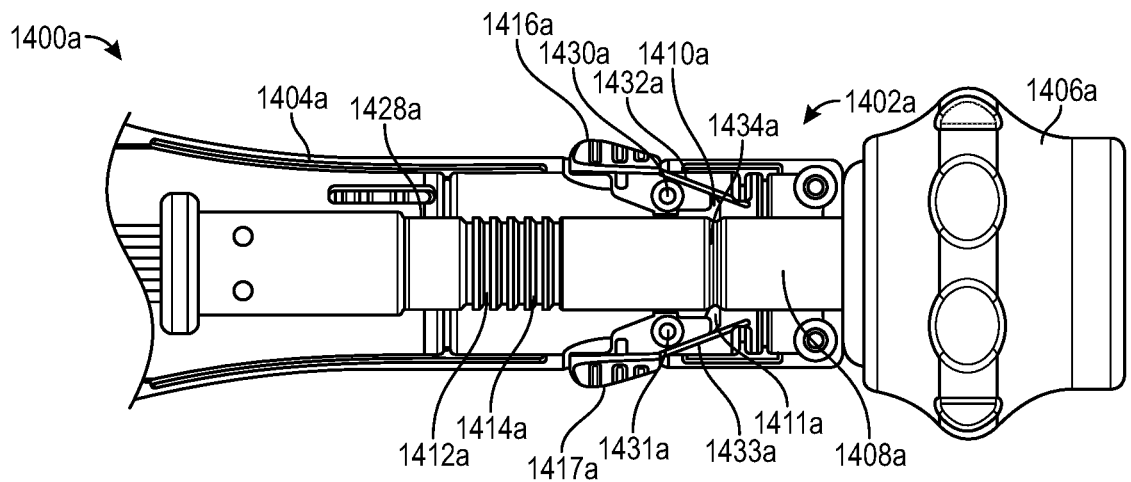
FIGS. 14A-14B are cross-sectional side views of alternative handles of a retrieval system including an alternative implementation of a tensioning assembly.
Figure 14B:
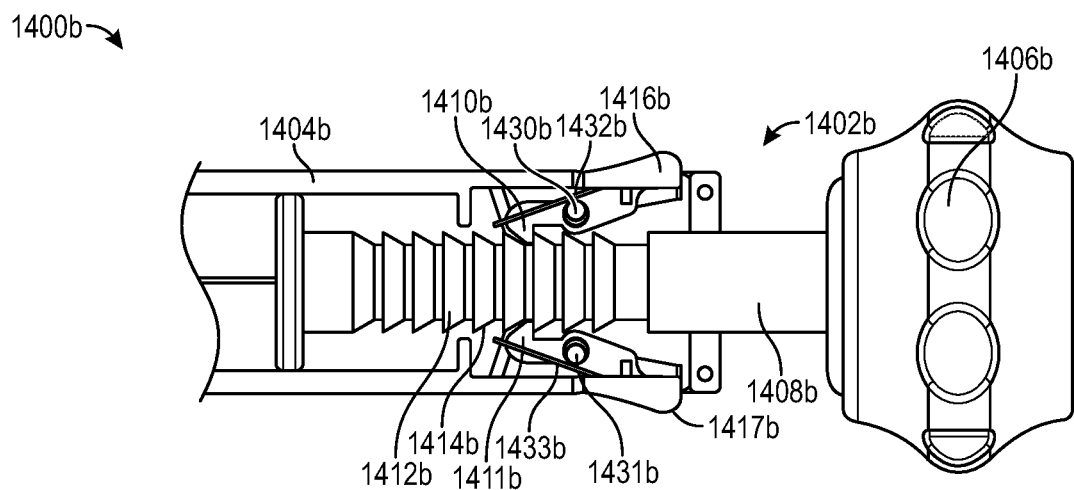

FIGS. 14A-14B illustrate alternative implementations of tensioning assemblies in accordance with this disclosure, each of which may be implemented in a retrieval system, such as the system 100 of FIG. 1D.

Referring first to FIG. 14A, a tensioning assembly 1400a according to another implementation is illustrated. Similar to the tensioning assembly 1300 of FIGS. 13A-13C, the tensioning assembly 1400a includes a handle 1402a including a distal handle portion 1404a and a proximal handle portion 1406a having a shaft 1408a that is disposed and translatable within the distal handle portion 1404a. The shaft 1408a includes a rack 1412a including a plurality of teeth 1414a adapted to receive a pair of pawls 1410a, 1411a coupled to the distal handle portion 1404a. In contrast to the teeth 1314 of the rack 1312 of FIGS. 13A-13C, which extended from the shaft 1308, the teeth 1414a of the rack 1412a are formed into the shaft 1408a and, as a result, extend inwardly from an exterior surface 1428a of the shaft 1408a.

As shown in FIG. 14A, the pawls 1410a are coupled to mounting pins 1430a, 1431a extending through the distal handle portion 1404a. Each of the pawls 1410a, 1411a includes a button 1416a, 1417a that, when depressed, causes rotation of the respective pawl 1410a, 1411a about the mounting pins 1430a, 1431a. Each of the pawls 1410A, 1411a further includes a biasing member 1432a, 1433a adapted to bias the pawl 1410a towards the shaft 1408a. In the example implementation of FIG. 14A, the biasing members 1432a, 1433a are in the form of sheet metal springs. In other implementations, each biasing member 1432a, 1433a may instead be, among other things, a torsion spring coiled about a respective mounting pin 1430a, 1431a.

The shaft 1408a may further define a retention groove 1434a disposed proximal the rack 1420a. The retention groove 1434a may be positioned along the shaft 1408a such that the pawls 1410a engage the retention groove 1434a when the proximal handle portion 1406a in a distal-most position, such as illustrated in FIG. 14A. The retention groove 1434a may be shaped such that when engaged with the pawls 1410a, 1411a proximal movement of the proximal handle portion 1406a relative to the distal portion 1404a is prevented or resisted. To disengage the pawls 1410a, 1411a from the retention groove 1434a, a user may simply depress the buttons 1416a, 1417a to rotate the pawls 1410a, 1411a out of engagement with the retention groove 1434a, thereby enabling unrestricted proximal movement of the proximal handle portion 1406a. Although illustrated in FIG. 14A as being proximally displaced along the shaft relative to the rack 1402a, the retention groove 1434a may instead be a proximal tooth of the rack 1402a provided the rack 1402a extends sufficiently along the shaft 1408a that the pawls 1410a, 1411a engage the proximal tooth of the rack 1402a when the proximal handle portion 1406a is in a distal-most position.

Referring next to FIG. 14B, a tensioning assembly 1400b according to yet another second implementation is illustrated. Similar to the tensioning assembly 1300 of FIGS. 13A-13C, the tensioning assembly 1400b includes a handle 1402b including a distal handle portion 1404b and a proximal handle portion 1406b having a shaft 1408b that is disposed and translatable within the distal handle portion 1404b. The shaft 1408b includes a rack 1412b including a plurality of teeth 1414b adapted to receive a pair of pawls 1410b, 1411b coupled to the distal handle portion 1404b. In contrast to the pawls 1410a, 1411a of FIG. 14A, which extended in a proximal direction, the pawls 1410b, 1411b of FIG. 14B extend in a distal direction. In either implementation, resistance to distal movement of the proximal handle portion may be a result of one or both of spring force exerted by biasing members and mechanical interference between the pawls and the rack.

In further contrast to the tensioning assembly 1400a of FIG. 14A, the tensioning assembly 1400b of FIG. 14B excludes a retention groove and instead includes an elongated rack 1412b including a proximal rack segment 1413b shaped to receive the pawls 1410b, 1411b when the proximal handle portion 1406b is disposed in a distal-most position relative to the distal handle portion 1404b. As shown in FIG. 14B, the pawls 1410b, 1411b are coupled to mounting pins 1430b, 1431b extending through the distal handle portion 1404b and each of the paws 1410b, 1411b includes a button 1416b, 1417b that, when depressed, causes rotation of the respective pawls 1410b, 1411b about the mounting pins 1430b, 1431b, such rotation causing disengagement of the pawls 1410b, 1411b from the rack 1412b. Each of the pawls 1410b, 1411b further includes respective biasing members 1432b, 1433b adapted to bias the pads 1410b, 1411b towards the shaft 1408b.

Figure 15A:
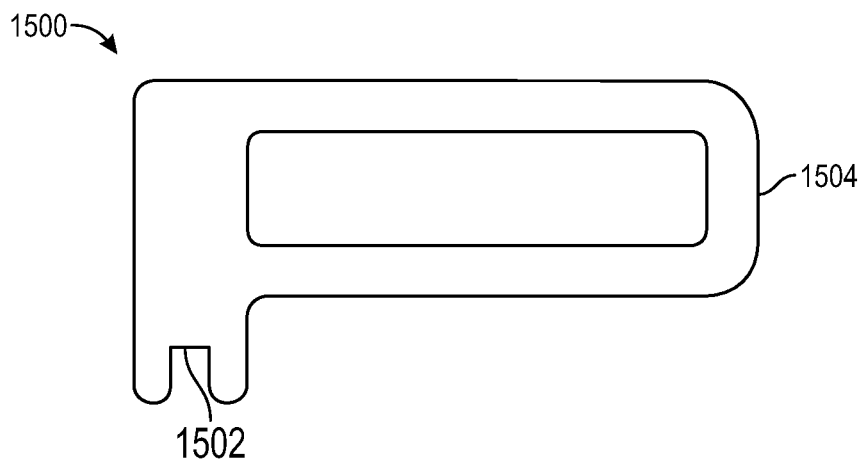
FIG. 15A is a plan view of a spring for use in the tensioning assemblies of FIGS. 14A-14B.
Figure 15B:
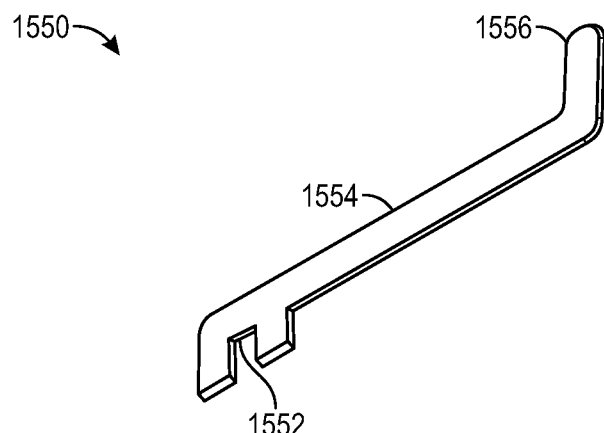
FIG. 15B is an isometric view of a spring for use in the tensioning assemblies of FIGS. 14A-14B.

FIG. 15A is a top plan view of a first example biasing member 1500 and FIG. 15B is an isometric view of a second example biasing member 1550, each of which may be implemented as the biasing members 1432a, 1433a and 1432b, 1433b of FIGS. 14A and 14B, respectively. Each of the example biasing members 1500, 1550 may be formed from sheet metal using, among other processes, laser cutting and stamping. The first example biasing member 1500 includes a coupling feature 1502 coupled to a looped spring body 1504. Similarly, the second example biasing member 1550 includes a coupling feature 1552 coupled to an elongated spring body 1554 that terminates in a tab 1556. Each of the coupling features 1502, 1552 is shaped to mate with or otherwise be retained by a corresponding feature of the pawls shown in FIGS. 14A-14B. With reference to FIG. 14A, the spring bodies 1502, 1552 may extend from the buttons 1416a, 1417a of the pawls 1410a, 1411a and past the mounting pins 1430a, 1431a such that the spring bodies 1502, 1552 abut or are otherwise retained by internal features of the distal handle portion 1402a.

The biasing force provided by the biasing members 1500, 1550 may be varied by changing, among other things, the material, thickness, and overall shape of the biasing members 1500, 1550. In certain implementations, the biasing members 1500, 1550 may be formed from, among other things, steel and nitinol and may have a thickness from and including 0.004 inches to and including 0.022 inches.

Figure 15C:
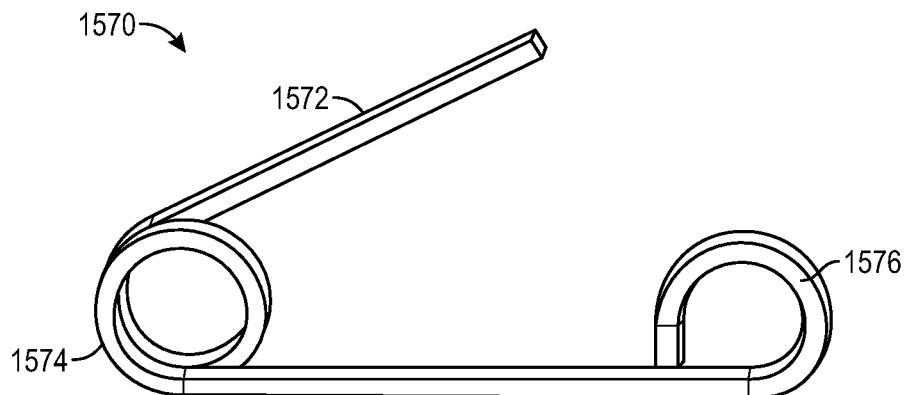
FIG. 15C is a side elevation view of a spring for use in the tensioning assemblies of FIGS. 14A-14B.

FIG. 15C is a side elevation view of a third example of a biasing member 1570 that may be implemented in the as the biasing members 1432a, 1433a and 1432b, 1433b of FIGS. 14A and 14B, respectively. The biasing member 1570 including a free leg 1572, a first loop 1574 and a second loop 1576. In certain implementations, the biasing member 1570 may have a substantially square cross-section and be formed from a substantially resilient material such as, without limitation, 304V stainless steel. With reference to FIG. 14A, when installed, each of the first loop 1574 and the second loop 1576 may be supported by respective pins extending through the handle housing such that the free leg rests underneath and applies an outward force on the buttons 1416a, 1417a. In certain implementations, one of the pins may include one the mounting pins 1430a, 1431a about which the pawls 1410a, 1411a rotate. Alternatively, one or both of the pins supporting the biasing member 1570 may be separate from the mounting pins 1430a, 1431a.

D. Catheter Retrieval System Handle Including Counter-Rotation System

As previously discussed in the context of FIGS. 1A-8B, leadless pacemakers may be fixed to the endocardium by a helical screw or similar fixation mechanism disposed on a distal end of the leadless pacemaker. As a result, fixation of the leadless pacemaker generally involves rotating the leadless pacemaker in a first rotation direction such that the helical screw sufficiently penetrates and screws into the endocardium to maintain the leadless pacemaker in place. Subsequent retrieval and removal of the implanted leadless pacemaker generally includes coupling the leadless pacemaker to a catheter of a retrieval system and counter-rotating the leadless pacemaker to unscrew and disengage the helical screw from the endocardium.

Rotation of the helical screw in the proper direction during each of implantation and retrieval of the leadless pacemaker is critical during each procedure. During implantation, for example, the helical screw will generally not engage the endocardium if rotated in the incorrect direction. During retrieval, failure to rotate the leadless pacemaker in the proper direction can be even more problematic. In addition to failing to disengage the helical screw from the endocardium, rotation in the fixation direction may drive the helical screw deeper into the endocardium and, in certain cases, may pierce through the endocardium or otherwise cause excessive trauma to the heart.

To address the foregoing issues, retrieval systems according to the present disclosure include a counter-rotation feature that prevents the user from rotating a proximal handle portion in a predetermined direction. In certain implementations, the counter-rotation feature is only engaged after an implantable medical device is captured and docked with a retrieval catheter of the retrieval system. As a result, a user may freely manipulate the proximal handle portion and a snare, tether, or similar retention mechanism coupled to the proximal handle portion during initial capture of the implantable medical device while subsequently being protected from improper rotation following docking of the implantable medical device.

The counter-rotation feature disclosed herein increases safety of catheters while retrieving leadless pacemakers and other implantable medical devices. The counter-rotation ensures correct rotation of a proximal handle portion of a retrieval system when the pacemaker is docked such that the leadless pacemaker or similar implantable medical device cannot be further rotated into tissue, such as the heart wall. The counter-rotation feature is only active while the leadless pacemaker or implantable medical device is docked to the retrieval system. Notably, the user is not generally required to perform additional steps to activate or deactivate the counter-rotation feature. Rather, the counter-rotation feature is engaged or disengaged automatically during the regular course of capturing and docking the implantable medical device. In certain implementations, the counter-rotation feature may also produce an audible click or tactile bump every time the proximal handle portion is rotated a predetermined number of degrees, thereby providing additional information and feedback to the user during unscrewing of the leadless pacemaker or other implantable medical device.

Figure 16A:
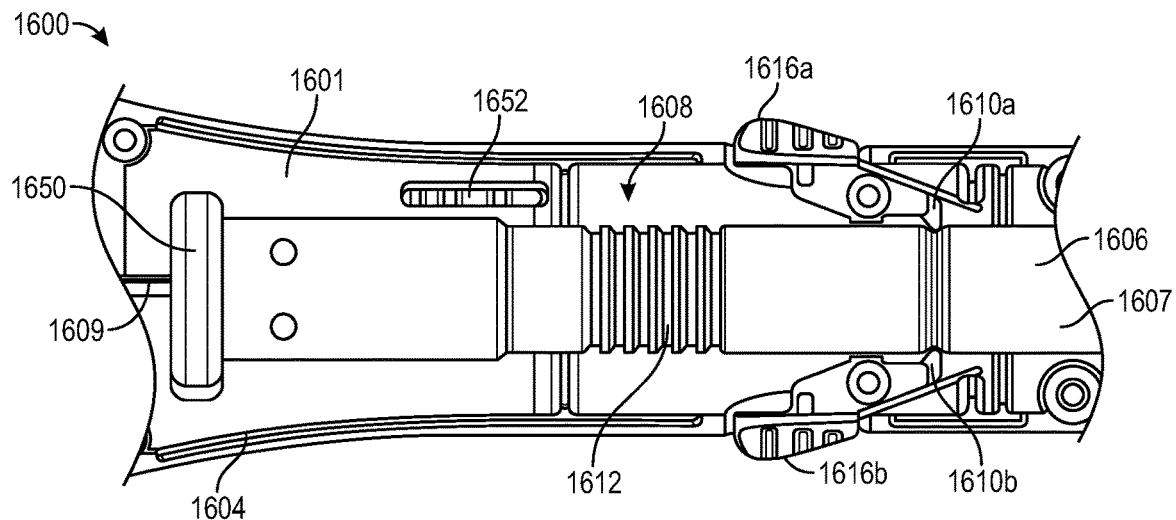
FIG. 16A is a cross-sectional side view of a handle of a retrieval system including an anti-rotation assembly.

FIG. 16A is a side view of a handle 1600 including a counter-rotation assembly 1601 for use in a retrieval system, such as the system 100 illustrated in FIG. 1D. The handle 1600 generally includes a distal handle portion 1604 and a proximal handle portion 1606. As illustrated in FIG. 14A, the proximal handle portion 1606 includes a shaft 1607 that extends at least partially into the distal handle portion 1604. The proximal handle portion 1606 is coupled to a tensioning member 1609, such as a wire, that extends from the handle 1602 and to a distal end of the retrieval system where the tensioning member 1609 may be coupled to or may terminate in a snare, tether, lasso, or similar retrieval feature that may be coupled to a corresponding mating feature of an implantable medical device, such as a leadless pacemaker.

Similar to the implementation previously described in the context of FIGS. 13A-14B, the distal handle portion 1604 and the proximal handle portion 1606 may be coupled together by a ratchet mechanism 1608 that includes one or more pawls 1610a, 1610b of the distal handle portion 1604 and a rack 1612 disposed on the shaft 1607. As described in more detail in the context of FIGS. 13A-14B, the proximal handle portion 1606 may be pulled and translated proximally to apply tension to the tensioning member 1609. As the proximal handle portion 1606 is further pulled in the proximal direction, the ratchet mechanism 1608 engages such that the proximal handle portion 1606 becomes "locked" relative to the distal handle portion 1604. In the locked configuration, distal movement of the proximal handle portion 1606 is prevented by engagement of the pawls 1610a, 1610b with the rack 1612 while further proximal translation of the proximal handler portion 1606 may be allowed to increase tension on the tensioning member 1609.

The handle 1600 may be configured such that engagement of the ratchet mechanism 1608 corresponds to docking of the implantable medical device with a catheter of the retrieval system, such as described in the context of FIGS. 5A-6B. Accordingly, the initial tension applied by the proximal handle portion 1606 may coincide with operation of the retrieval feature (e.g., cinching or tightening of a snare) and subsequent drawing together of the implantable medical device and the catheter. When the implantable medical device and the catheter are in contact, as evidenced by engagement of the ratchet mechanism 1608, the implantable medical device may be considered docked with respect to the catheter and a user may sheath the implantable medical device with a guide catheter of the retrieval system. The proximal handle portion 1606 may then be rotated counterclockwise to unfix the leadless pacemaker from the heart wall.

During retrieval of an implantable medical device, there is the potential that a user of the retrieval system may incorrectly rotate the proximal handle portion 1606 in a clockwise direction resulting in further screwing in of the implantable medical device into the corresponding tissue. For example, clockwise rotation may cause the helix of a leadless pacemaker to dig further into cardiac tissue. To prevent such rotation, the handle 1600 includes anti-rotation functionality provided by interaction between a ratchet wheel 1650 disposed on a distal end of the second handle portion 1606 and a protrusion 1652 extending towards the shaft 1607 from the housing 1602.

In certain implementations, the protrusion 1652 and the ratchet wheel 1650 are arranged with respect to each other such the ratchet wheel 1650 is aligned with the protrusion 1652 when the proximal handle portion 1606 is proximally translated into a position corresponding to docking of an implantable medical device being retrieved. In implementations including a ratchet mechanism, such as the ratchet mechanism 1608, such a position may be signaled to the user by engagement of the ratchet mechanism 1608. The ratchet wheel 1650 is shaped such that when aligned with the protrusion 1652, the protrusion 1652 substantially blocks rotation of the ratchet wheel 1650 in a clockwise direction, thereby preventing a user from rotating the proximal handle portion 1606 in a clockwise direction.

To disengage the anti-rotation functionality, a user may simply depress buttons 1616a, 1616b or similar features adapted to release the pawls 1610a, 1610b from the rack 1612. Once released, the proximal handler portion 1606 may be translated distally to misalign the ratchet wheel 1650 and the protrusion 1652, thereby allowing bi-directional rotation of the proximal handle portion 1606. Accordingly, in the event that a user must unlock the leadless pacemaker from the retrieval catheter, the anti-rotation functionality is automatically disengaged without additional intervention by the user.

Figure 16B:
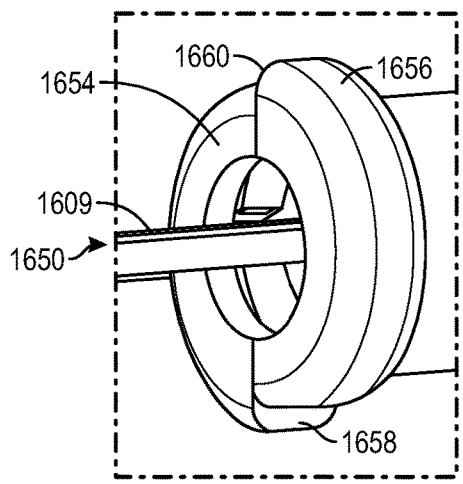
FIG. 16B-16C are isometric detail views of the anti-rotation assembly of FIG. 16A.
Figure 16C:
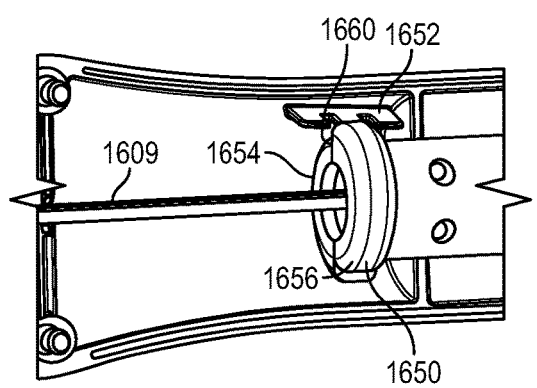

FIG. 16B is an isometric view of the ratchet wheel 1650. In certain implementations, the ratchet wheel 1650 may include two or more lobes 1654, 1656 coupled to each other in an offset manner. By being offset, each lobe 1654, 1656 forms a respective, stopping face 1658, 1680 that abuts the protrusion 1652 when the ratchet wheel 1650 is aligned with the protrusion 1652, as shown in FIG. 16C, and a clockwise rotation is applied to the proximal handle portion 1606. In certain implementations, the ratchet wheel 1650 may be formed with the shaft 1607 or, alternatively, may be formed separately from the shaft 1607 and coupled to the shaft, such as by using ferrol or similar pins.

In the example of FIG. 16B, the ratchet wheel 1650 includes two offset lobes 1654, 1656 having semi-circular shapes such that the ratchet wheel 1650 provides a ratcheting effect every half rotation of the proximal handler portion 1606. In other implementations, the quantity of lobes may be increased such that a more discrete ratcheting effect is achieved. For example, in certain implementations, the ratchet wheel 1650 may be composed of four offset quarter-circular lobes such that ratcheting is provided every quarter turn.

In addition to preventing clockwise rotation of the shaft 1607, the interaction between the ratchet wheel 1650 and the protrusion 1652 also provides audial and/or tactile feedback when the shaft 1607 is rotated in the counterclockwise direction. Such feedback may be useful to a user of the handle 1600 to determine the number of counterclockwise rotations that have been applied to the proximal handle portion 1606 and, as a result, a leadless pacemaker coupled to the retrieval catheter of the retrieval system.

Audial and/or tactile feedback is provided by interaction between the ratchet wheel 1650 and the protrusion 1662 during counterclockwise rotation of the proximal handle portion 1607. In contrast to clockwise rotation during which the ratchet wheel is obstructed by the protrusion 1652, counterclockwise rotation causes the protrusion 1662 to travel along the outer surface of the lobes 1654, 1656, flex or deflecting the protrusion 1652. In certain implementations, such deflection of the protrusion 1652 may increase resistance to further counterclockwise rotation of the proximal handle portion 1606, thereby providing tactile feedback to the user. Moreover, the outer surface of the lobes 1664, 1656 may further be modified to produce a predetermined resistance profile. For example, the outer surface of the lobes 1664, 1656 as illustrated in FIGS. 16A-16C are semi-circular and, as a result, generally produce a resistance profile in which the resistance to counterclockwise rotation increases gradually, peaks, and then decreases gradually as the proximal handle portion 1606 is rotated. In another implementation, the outer surface of the lobes 1654, 1656 may include a linear ramp such that the rotational resistance linearly increases as the proximal handle portion 1606 is rotated.

As counterclockwise rotation is continued, the protrusion 1652 passes the stopping faces 1658, 1660 of the lobes 1654, 1656. In certain implementations, a click or other sound may occur along with a bump or sudden decrease in rotational resistance provided by the protrusion 1652. During a retrieval process, a user may count the clicks and/or changes in rotational resistance to track the number of counterclockwise rotations that have been applied to the proximal handle portion 1606. For example, the ratchet wheel 1650 would produce a click or bump every half-turn.

Figure 17A:
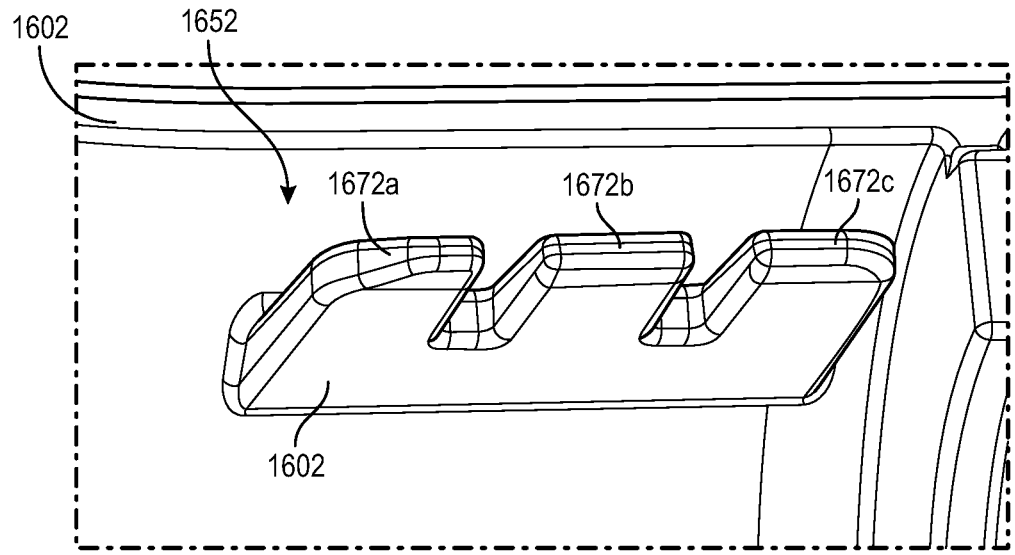
FIG. 17A-17B are detail views of protrusions that may be incorporated into the anti-rotation assembly of FIG. 16A.

In addition to varying the quantity and shape of the ratchet wheel 1660, performance characteristics of the handle 1600 may further be modified by varying the design of the protrusion 1652. FIG. 17A illustrates the protrusion 1652 of the handle 1600 in further detail. As shown, the protrusion 1662 is a multi-part fin 1652 extending from an internal surface of the housing 1602. More specifically, the multi-part fin 1652 includes a base 1670 from which three fin segments 1672a, 1672b, 1672c extend.

Each of the fin segments 1672a-1672c may be positioned such that the distal shaft end 1650 aligns with one or more of the fin segments 1672a-1672c as the distal shaft end 1650 is moved between different locked positions. The fin segments 1672a-1672c are generally spaced such that the distal shaft end 1650 is unable to be rotated between any two adjacent pairs of the fins segments 1672a-1672c.

The size, shape, and construction of the protrusion 1652 may be modified to change the resistance provided by the protrusion 1652 to counterclockwise rotation of the proximal handle portion 1606. For example, the length the fin segments 1672a-1672c may be increased or the thickness of the fin segments 1672a-1672c may be decreased in order to reduce the rigidity of the fin segments 1672a-1672c and, as a result, reduce the resistance provided by the fine segments 1672a-1672c to counterclockwise rotation of the proximal handle portion 1606. Conversely, the length of the fin segments 1672a-1672c may be shortened or the thickness of the fin segments 1672a-1672c may be increased to increase the rigidity of the fin segments 1672a-1672c. The material used for the fin segments 1672a-1672c may also be selected to impart specific rigidity to the fin segments 1672a-1672c.

Figure 17B:
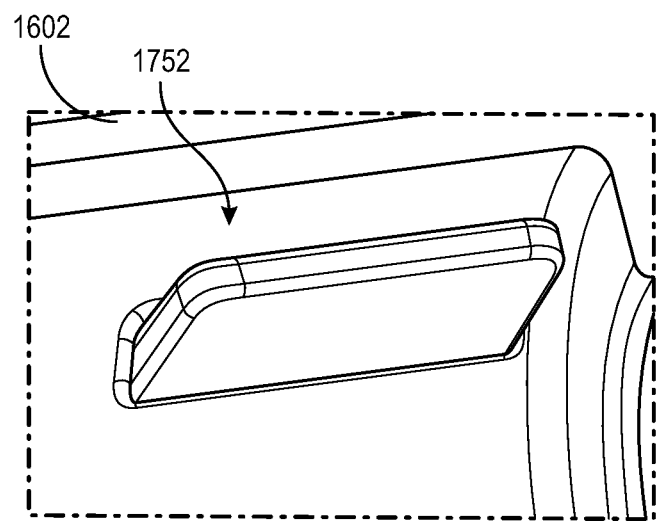

In other implementations, more or fewer fin segments may be implemented. For example, FIG. 17B illustrates a one-piece fin 1752 extending from the housing 1602.

Figure 18A:
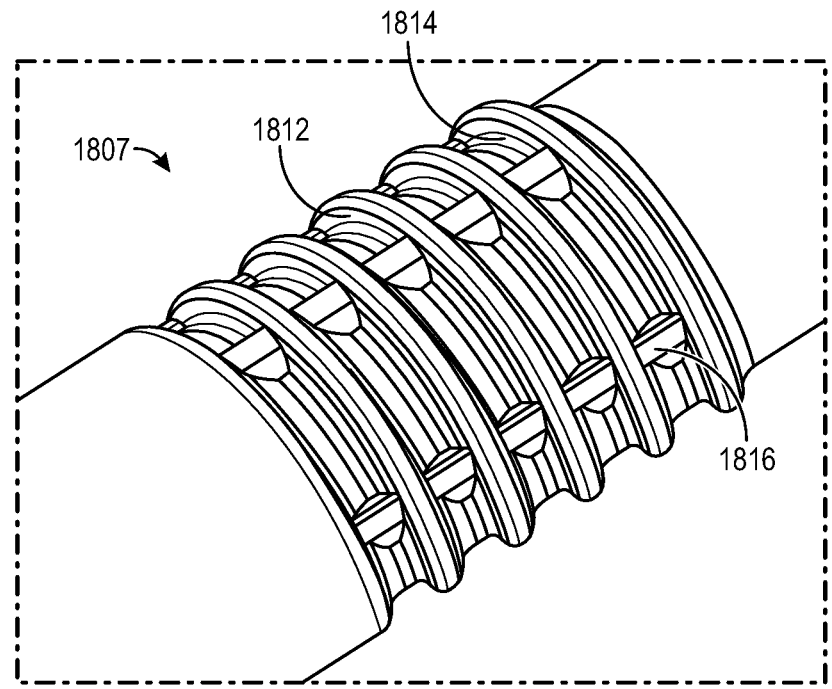
FIG. 18A is an isometric view of a proximal handle portion shaft for use in a handle of a retrieval system including anti-rotation features.
Figure 18B:
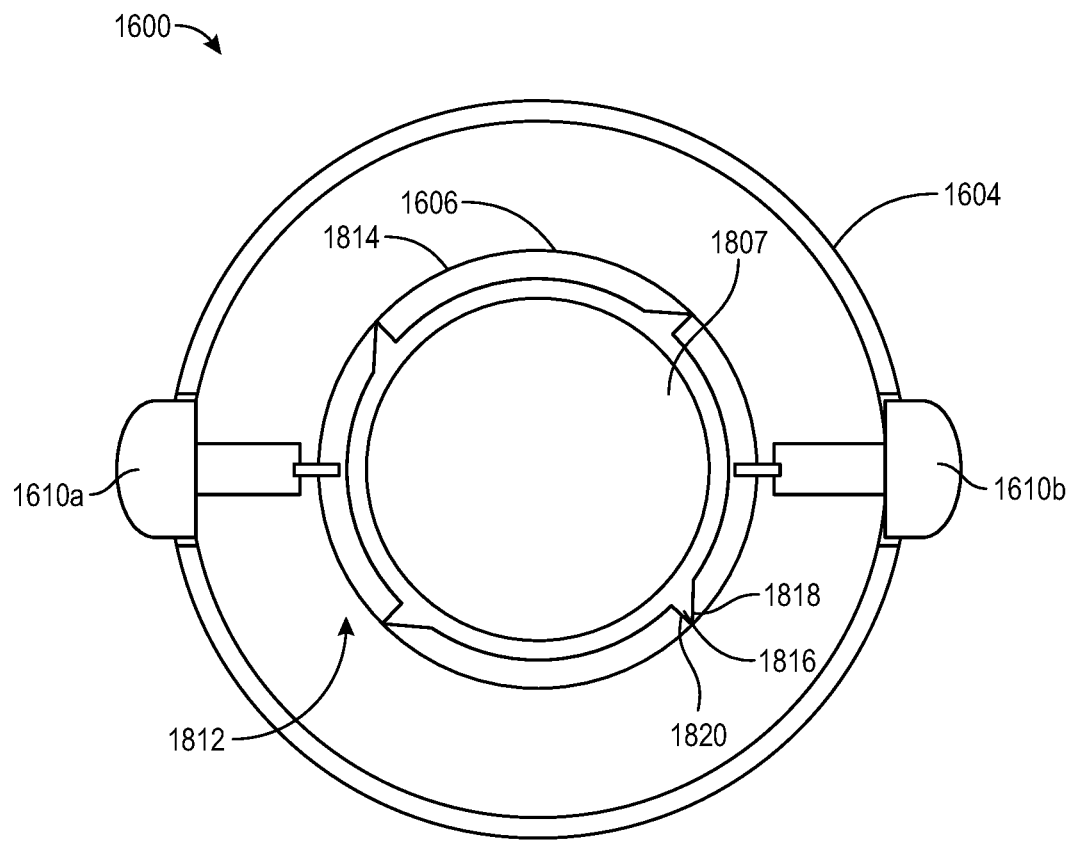
FIG. 18B is a cross-sectional view of a handle including the shaft of FIG. 18A.

FIG. 18A is an isometric view of an alternative shaft 1607 that may be implemented as part of the proximal handle portion 1606 of the handle 1600. FIG. 18B is a cross sectional view of the handle 1600 including the shaft 1807.

Similar to the shaft 1607 illustrated in FIG. 16A, the shaft 1807 includes a rack 1812 adapted to engage corresponding pawls 1610 of a distal handle portion 1604 (each shown in FIG. 16A) into which the shaft 1807 is inserted. In particular, the rack 1812 includes a plurality of teeth 1814 shaped to engage the pawls 1610 to restrict distal movement of the proximal handle portion 1606 while still enabling further proximal movement of the proximal handle portion 1606. Between adjacent pairs of teeth 1814 of the rack 1812, secondary teeth 1816 are disposed about the circumference of the shaft 1807. The secondary teeth 1816 are shaped and positioned to block clockwise rotation of the shaft 1807 when the pawls 1610a, 1610b have engaged the rack 1812. Accordingly, each of the sections disposed between adjacent teeth 1814 of the rack defines an independent ratchet wheel adapted to allow rotation of the shaft 1807 in a first direction while obstructing rotation of the shaft 1807 in a second direction opposite the first direction as determined by the shape and orientation of the secondary teeth 1816.

Referring to FIG. 18B the anti-rotation functionality provided by the secondary teeth 1816 is further illustrated. FIG. 18B is a simplified cross-sectional view of the handle 1600 including the alternative shaft 1807 in taken in a distal direction. The distal handle portion 1604 is shown with the pawls 1610a, 1610b engaging a tooth 1814 of the rack 1812 formed into the surface of the shaft 1807. As previously noted, a plurality of secondary teeth 1816 are circumferentially distributed about the shaft 1807 between adjacent teeth 1814 of the rack 1812.

Each of the secondary teeth 1816 generally includes a ramped tooth surface 1818 and a stopping face 1820. The ramped tooth surfaces 1818 of the secondary teeth 1816 are oriented such that counterclockwise rotation of the shaft 1807 causes the pawls 1610 to ride over the secondary teeth 1816. In contrast, the stopping faces 1820 are oriented such that clockwise rotation of the shaft 1807 causes the pawls 1610 to abut the stopping faces 1820, thereby preventing further clockwise rotation of the shaft 1807.

Similar to the interaction between the distal shaft end 1650 and the protrusion 1652, interaction between the secondary teeth 1816 and the pawls 1610A, 1610B may result in one or both of audial and tactile feedback. As the shaft 1807 is rotated in a clockwise direction and the pawls ride over the secondary teeth 1816, interference between the secondary teeth 1816 and the pawls 1610, 1610B may result in an increased resistance to clockwise rotation of the shaft 1807. When the secondary teeth 1816 are overcome by further rotation of the shaft 1807, a corresponding bump or click may result as the interference between the pawls 1610A, 1610B and the secondary teeth 1816 is eliminated. Although illustrated in FIG. 18B as being substantially linear, the ramped tooth surfaces 1818 may have other shapes selected to provide a specific rotational resistance profile as the pawls 1610A, 1610B are passed over the secondary teeth 1816. For example, the ramped tooth surfaces 1818 may be curved or include multiple sections having different ramp angles.

The quantity and distribution of the secondary teeth 1816 may also be varied to provide finer or more granular feedback to a user of the handle 1600 and to limit the amount of clockwise rotation permitted by the handle 1600. For example, the shaft 1807 of FIG. 18B includes four secondary teeth 1816, thereby providing a bump or click in response to every quarter turn of the shaft 1807 and limiting clockwise rotation to no more than a quarter turn of the shaft 1807. In certain implementations, additional secondary teeth 1816 may be included to provide more frequent feedback and to further limit the amount of permissible rotation in the clockwise direction. Similarly, fewer secondary teeth 1816 may be included to provide less frequent feedback and to enable a larger amount of clockwise rotation.

E. Catheter Delivery System Handle Including Torsional Strain Relief System

Conventional retrieval systems for implantable medical devices, such as leadless pacemakers, include a snare or similar retrieval feature that is adapted to couple with a button or similar feature of the leadless pacemaker. In the case of a snare, tension may then be applied to the snare to close or cinch the snare about the coupling feature of the leadless pacemaker and to dock the leadless pacemaker within a docking cap or similar structure disposed on a distal end of a retrieval catheter of the retrieval system.

Once docked, the leadless pacemaker may be unscrewed from tissue in which the leadless pacemaker is implanted by applying torque to a torque shaft that is coupled to the retrieval catheter by a drive gear. In conventional retrieval systems, transmission of torque from a handle of the retrieval system to the leadless pacemaker requires that the drive gear of the torque shaft properly seat in and engage the docking cap. If the drive gear does not engage the docking cap, torque is not transmitted through the torque shaft as intended, but is instead transmitted through the snare. Buildup of torque in the snare can lead to several unwanted events. For example, the snare may be permanently damaged or fracture such that the snare is unable to function properly or the snare may cause the coupling feature of the pacemaker to be damaged.

In light of the foregoing, the present disclosure provides a handle for a retrieval system for use in retrieving leadless pacemakers and similar implantable medical devices that includes a torsion release mechanism. The torsion release mechanism rotationally decouples the retrieval feature from the retrieval catheter once the leadless pacemaker or other implantable medical device is properly docked. Prior to docking, the retrieval feature is rotationally coupled to the handle to enable a user to position the retrieval feature by making rotational adjustments to the handle. However after docking, the retrieval feature is allowed to unwind and release built up torsional energy. Accordingly, the mechanism disclosed herein allows for positioning of the retrieval feature prior to docking and allows for relief of torsional buildup on the retrieval feature snare without losing tension on the implantable medical device.

The torsional strain relief mechanism of the present disclosure generally includes a handle within which a first gear is rotationally supported, for example, by a ball bearing. The first gear is coupled to the retrieval feature such that rotation of the first gear causes rotation of the retrieval feature. The torsional strain relief mechanism further includes a shuttle having a second gear. The shuttle is rotationally fixed to the handle but is translatable along the handle between a first shuttle position and a second shuttle position. In the first shuttle position the first gear and the second gear are engaged such that rotation of the handle causes rotation of the retrieval feature. In the second shuttle position, the first gear and the second gear are disengaged. When disengaged, the first gear is able to rotate freely within the housing because of the rotational mounting of the first gear to the housing. As a result, the first gear can spin to unwind the retrieval feature and dissipate any torsion that may be built up on the retrieval feature. Any further rotation of the handle when the first and second gears are disengaged results in rotation of the rotational mount about the first gear without generating torsion on the retrieval feature.

Figure 19A:
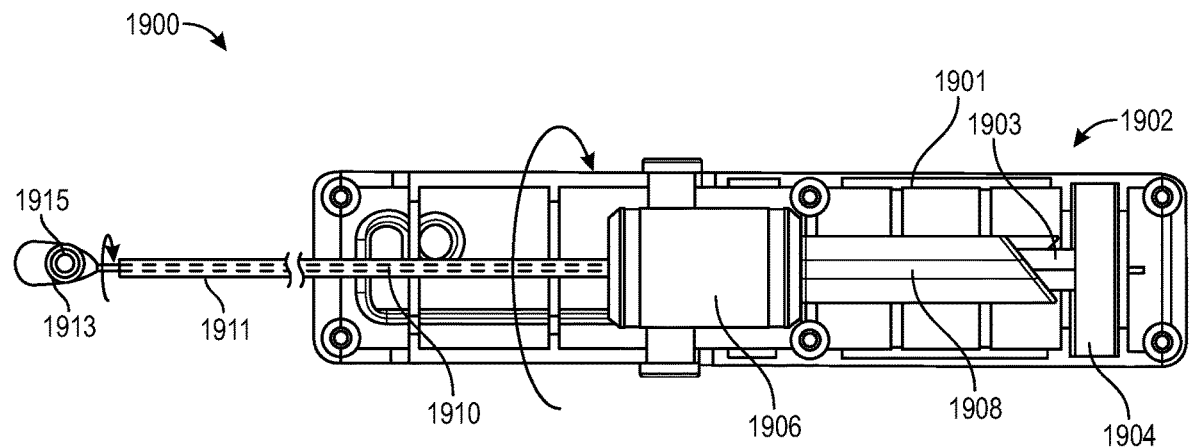
FIGS. 19A-19B are cross-sectional side views of a handle including a torsion relief mechanism in an engaged and disengaged configuration, respectively.
Figure 19B:
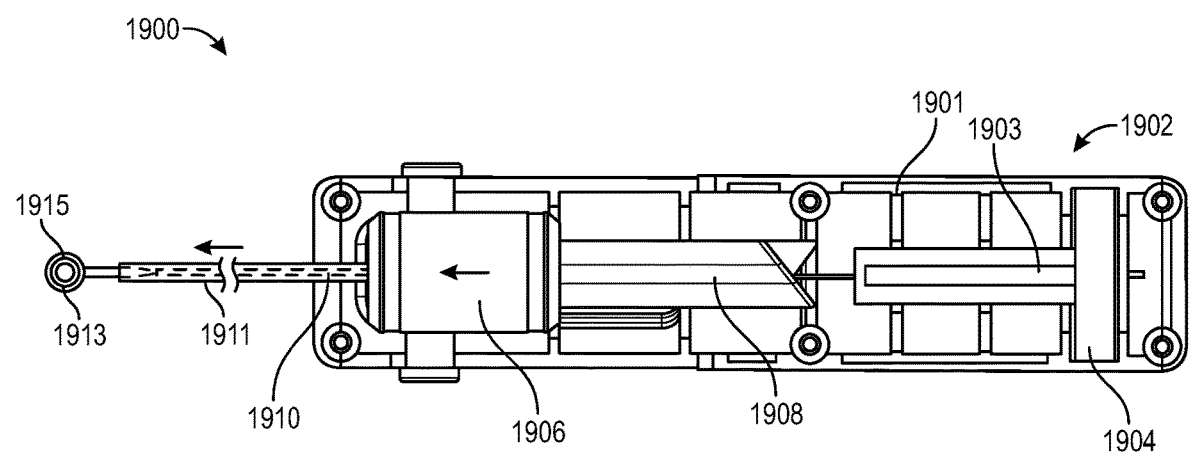

FIGS. 19A-19B are cross-sectional side view of a handle 1900 in accordance with the present disclosure. The handle 1900 generally includes a housing 1901 and a torsion release assembly 1902 including a first gear 1903 supported by a rotational mount 1904 that is further supported within the housing 1901. The first gear 1903 is fixed to a snare 1910 or similar retrieval feature such that rotation of the first gear 1903 results in rotation of the snare 1910. The handle 1900 further includes a shuttle assembly 1906 that is rotationally fixed to the housing 1901 and includes a second gear 1908. As shown in the transition between FIGS. 19A and 19B, the shuttle assembly 1906 is translatable along the housing 1901 between a first shuttle position (shown in FIG. 19A), which generally corresponds to a proximal position of the shuttle assembly 1906, and a second shuttle position (shown in FIG. 19B), which generally corresponds to a distal position of the shuttle assembly 1906. Also, as illustrated in FIG. 19B, in certain implementations the snare 1910 may extend through the shuttle assembly 1906 to be coupled to the first gear 1903.

The snare 1910 may generally be disposed within a catheter shaft 1911 coupled to the shuttle assembly 1906. Accordingly, as the shuttle assembly 1906 is translated between the first shuttle position and the second shuttle position, the catheter shaft 1911 similarly translates. As a result of such translation of the catheter shaft 1911, the snare 1910 may be drawn into the catheter shaft 1911 such that the snare 1910 is cinched. Such cinching may be used, for example, to capture an attachment feature 1915 of a leadless pacemaker 1913 or other implantable medical device with the snare 1910, as shown in FIG. 19B.

Referring first to FIG. 19A, when in the first shuttle position, the first gear 1903 and the second gear 1908 engage each other. Because the second gear 1908 is coupled to the shuttle assembly 1906 which is in turn rotationally fixed relative to the housing 1901, engagement of the first gear 1903 to the second gear 1908 results in the first gear 1903 being similarly rotationally fixed relative to the housing 1901. Accordingly, rotation of the handle 1900 when the shuttle assembly 1906 is in the first shuttle position results in rotation of each of the shuttle assembly 1906, the second gear 1908, the first gear 1903, and the snare 1910.

In contrast, FIG. 19B illustrates the shuttle assembly 1906 in the second shuttle position in which the second gear 1908 is disengaged from the first gear 1903. When disengaged from the second gear 1908, the first gear 1903 may freely rotate relative to the housing 1901 by virtue of the rotational mount 1904. For example, in implementations in which the rotational mount 1904 is a ball bearing including an inner race and an outer race, the outer race may be coupled to the housing 1901 while the inner race may be coupled to the first gear 1903. Accordingly, the housing 1901 and the first gear 1903 may rotate independently of each other absent any additional coupling of the first gear 1903 to the housing 1901.

During operation, a user may initiate capture of a leadless pacemaker with the shuttle assembly 1906 disposed in the first shuttle position, thereby allowing the user to rotate and manipulate the snare 1910 by rotating the handle 1900 to facilitate capture of the leadless pacemaker. Subsequent docking of the leadless pacemaker may be achieved by translating a torque shaft over a distal end of the snare 1910 such that the snare 1910 is cinched or otherwise tightened. In certain implementations, the shuttle assembly 1906 may be coupled to the torque shaft of the retrieval system such that distal translation of the shuttle assembly 1906 translates the torque shaft over the distal end of the snare 1910.

In addition to translating the torque shaft over the snare 1910, distal translation of the shuttle assembly 1906 disengages the first gear 1903 from the second gear 1908, allowing the first gear 1903 to freely rotate within the housing 1901. To the extent that any torsion had been bunt up in the snare 1910 during the capture and docking processes, such torsion is relieved by free rotation of the first gear 1903 within the rotational mount 1904 counter to the direction of the torsion. With the first gear 1903 free to rotate within the rotational mount 1904, any subsequent rotation of the handle 1901 with the shuttle assembly 1906 in the second shuttle position does not result in additional torsion being applied to the snare 1910. As a result, inadvertent over-torsion of the snare 1910 is avoided.

In certain implementations, the shuttle assembly 1906 is configured to translate over a one inch travel range relative to the housing 1901. In such implementations, the first shuttle position in which the first gear 1903 is engaged with the second gear 1908 may correspond to the shuttle assembly 1906 being disposed within the proximal three-quarters of an inch of the travel range. Conversely, the second shuttle position in which the first gear 1903 is disengaged from the second gear 1908 may correspond to the distal one-quarter inch of the travel range.

As previously noted, the rotational mount 1904 supports the torsion release assembly 1902 within the housing 1901 such that the first gear 1903 is freely rotatable within the housing 1901 absent engagement with the second gear 1908. In certain implementations, the rotational mount 1904 may be a bearing including ball, roller, or similar rolling elements. Tension on the snare 1910 during use of the handle 1900 to retrieve a leadless pacemaker or similar implantable medical device generally results in the torsion release assembly 1902 being pulled in a distal direction. To resist such forces, the rotational mount 1904 may be selected to include roller elements having high compressive strength, such as ball bearings made of steel or other metals.

Figure 20A:
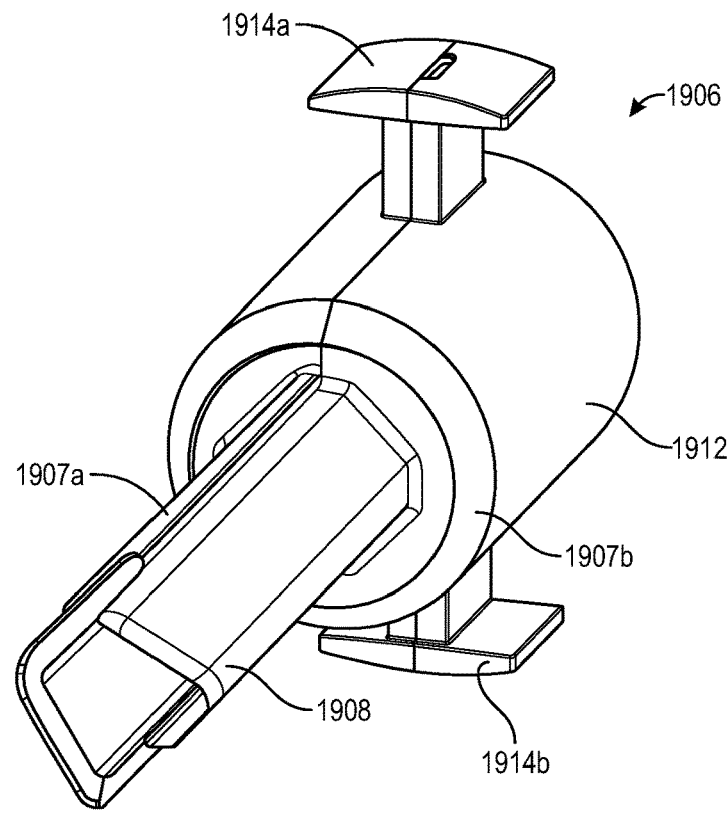
FIG. 20A is an isometric view of a shuttle assembly for use in the handle of FIGS. 19A-19B.

FIG. 20A is an isometric view of the shuttle assembly 1906 and the second gear 1908. As shown, the shuttle assembly 1906 may include a shuttle body 1912 from which grip features 1914a, 1914b extend. The grip features 1914a, 1914b extend through the housing 1901 (as shown in FIGS.

19A-19B) such that a user may push or pull the grip features 1914*a*, 1914*b* or structural features of the handle 1900 in contact with the grip features 1914*a*, 1914*b* to translate the shuttle assembly 1906 within the housing 1901. To improve moldability and manufacturing of the shuttle assembly 1906, the shuttle assembly 1906 and second gear 1908 may be formed from two shuttle assembly halves 1907*a*, 1907*b* that are coupled together.

Figure 20B:
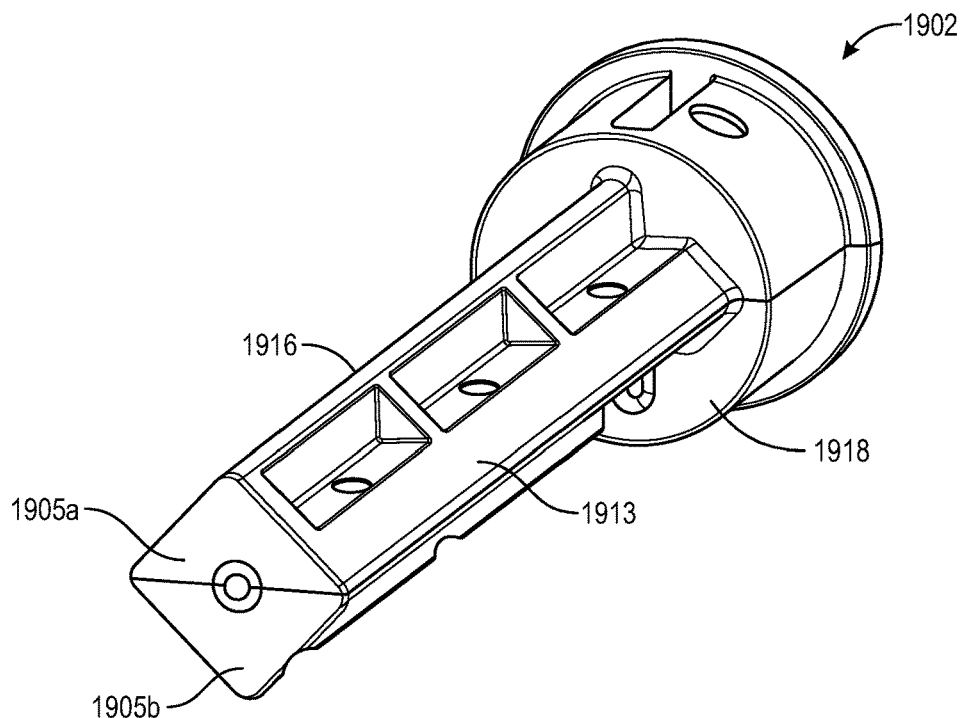
FIG. 20B is an isometric view of a torsion release assembly of the handle of FIGS. 19A-19B.

FIG. 20B is an isometric view of the torsion release assembly 1902. As illustrated, the first gear 1903 generally includes a gear shaft 1916 coupled to a gear hub 1918, the gear hub 1918 being adapted to be received within the rotational mount 1904 (shown in FIG. 19A-B). As shown in FIGS. 20A and 20B, each of the first gear 1908 and the second gear 1902 are substantially square in shape. Similar to the shuttle assembly 1906, in certain implementations, moldability and manufacturing of the shuttle torsion release assembly 1902 may be improved by forming the torsion release assembly from two torsion release assembly halves 1905*a*, 1905*b* that are subsequently coupled together.

Figure 20C:
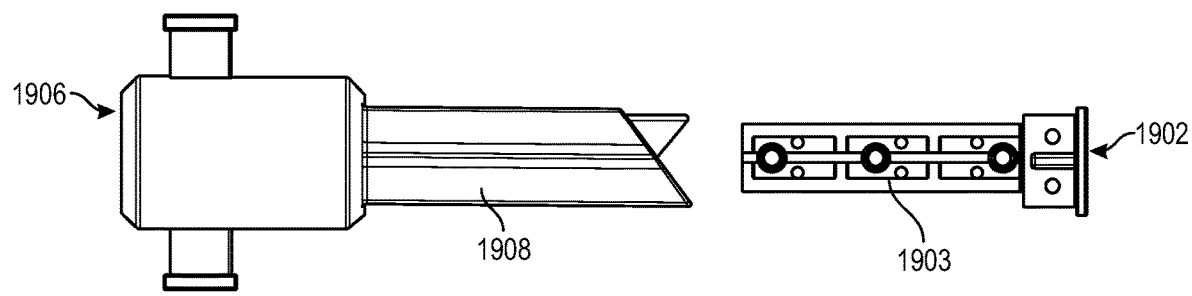
FIGS. 20C-20D are side views of the shuttle assembly of FIG. 20A and the torsion release assembly of FIG. 20B in disengaged and engaged configurations, respectively.
Figure 20D:
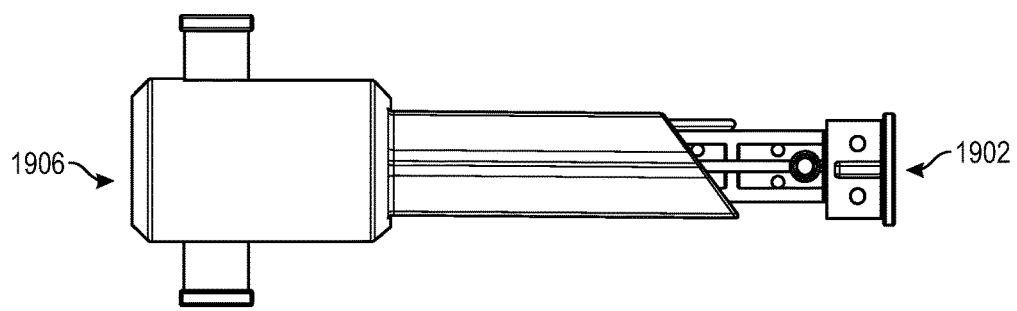

FIGS. 20C and 20D are side views of the shuttle assembly 1906 and the second gear 1908 in a disengaged and engaged configuration, respectively. When engaged, as in FIG. 20D, the first gear 1903 is inserted into the second gear 1908, thereby coupling the first gear 1903 to the shuttle assembly 1906.

FIGS. 20C and 20D illustrate engagement of the first gear 1903 and the second gear 1908 when the first gear 1903 and the second gear 1908 are oriented such that the first feat 1902 is properly aligned with the second gear 1908. Such orientation is likely to be rare during actual use and, as a result, the second gear 1908 may include self-aligning functionality adapted to rotate the first gear 1903 into the docking orientation. For example, in certain implementations, the second gear may include proximal guide surfaces that rotate the first gear 1903 into proper engagement orientation.

Figure 20E:
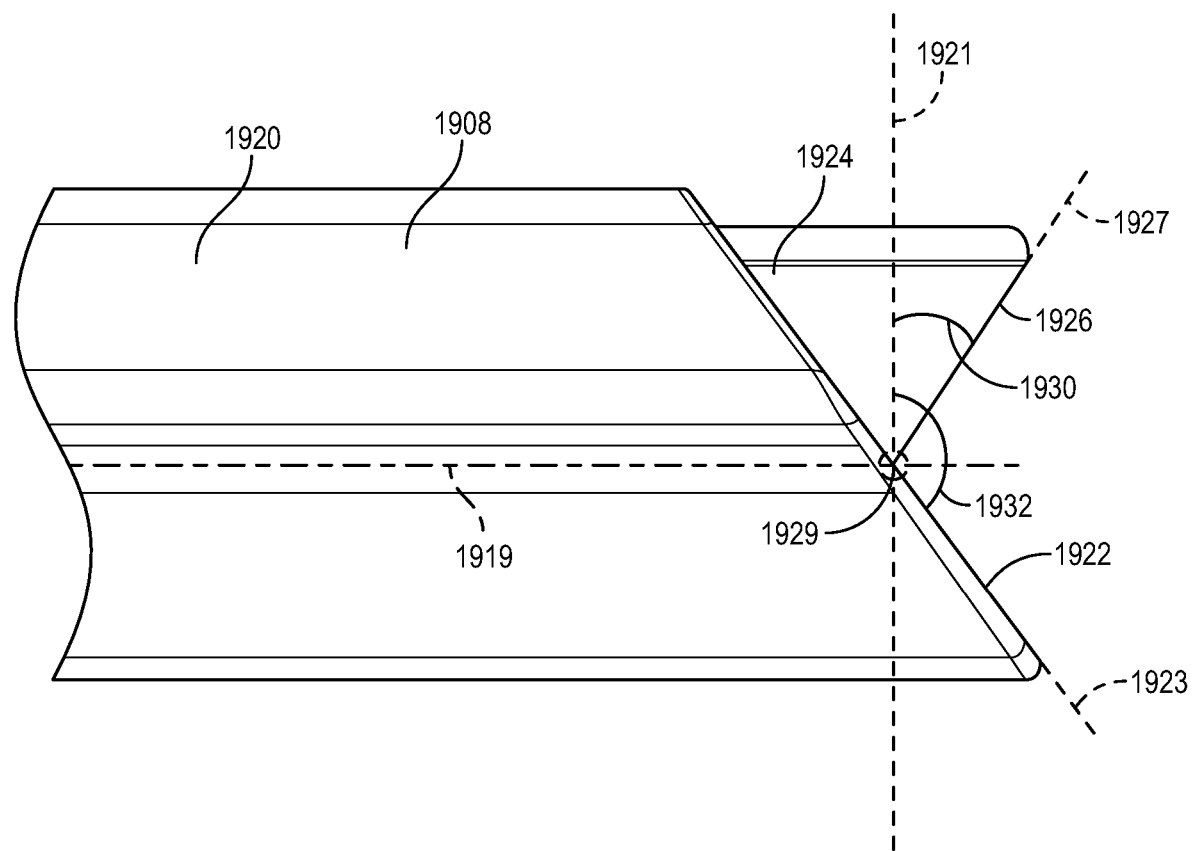
FIG. 20E is a side detail view of a proximal portion of the shuttle assembly of FIG. 20A.

FIG. 20E is a side view of the proximal end of the second gear 1908 and illustrates such guide surfaces. As shown in FIG. 20E, the second gear 1908 may define a longitudinal axis 1919 extending along the second gear 1908 normal to a cross-sectional plane 1921. The second gear 1908 may further include a first half 1920 having a first guide surface 1922 defining a first plane 1923 and a second half 1924 having a second guide surface 1926 defining a second plane 1927. The first plane 1923 is oriented at a first angle 1930 relative to the cross-sectional plane 1921 while the second plane 1927 is oriented at a second angle 1932 relative to the cross-sectional plane 1921 that is supplementary to the first angle 1926. As a result, the first and second planes 1923, 1927 intersect along a line 1929 (extending into the page of FIG. 20E) that is perpendicular to the longitudinal axis 1919. In certain implementations, the first angle 1930 may be from and including 35 degrees to and including 55 degrees.

Figure 20F:
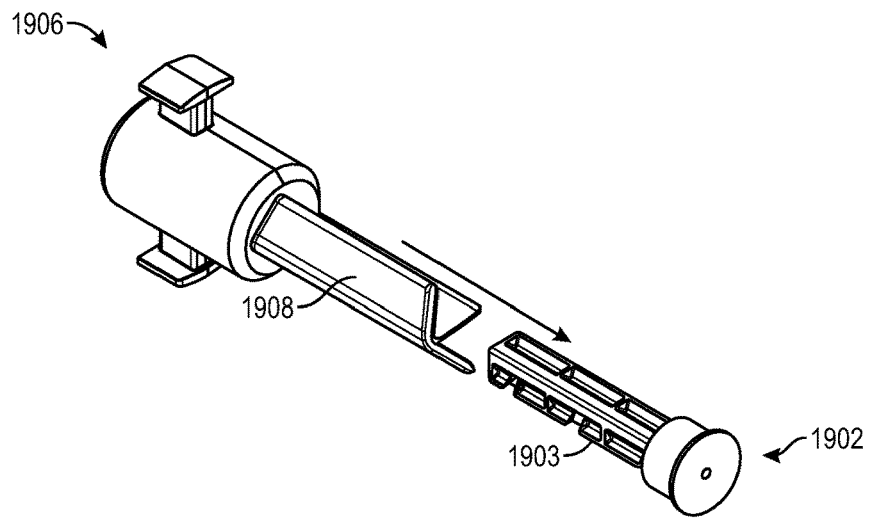
FIGS. 20F-20H are isometric views of the shuttle assembly of FIG. 20A and the torsion release assembly of FIG. 20B illustrating engagement of the shuttle assembly and the torsion release assembly.
Figure 20G:
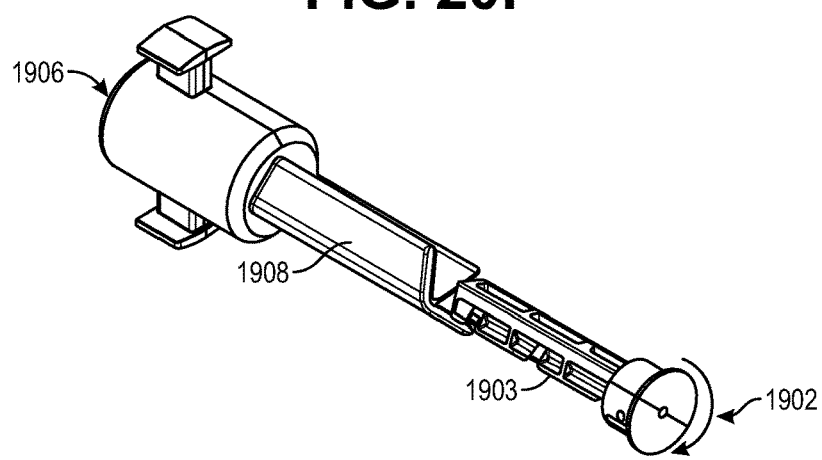
Figure 20H:
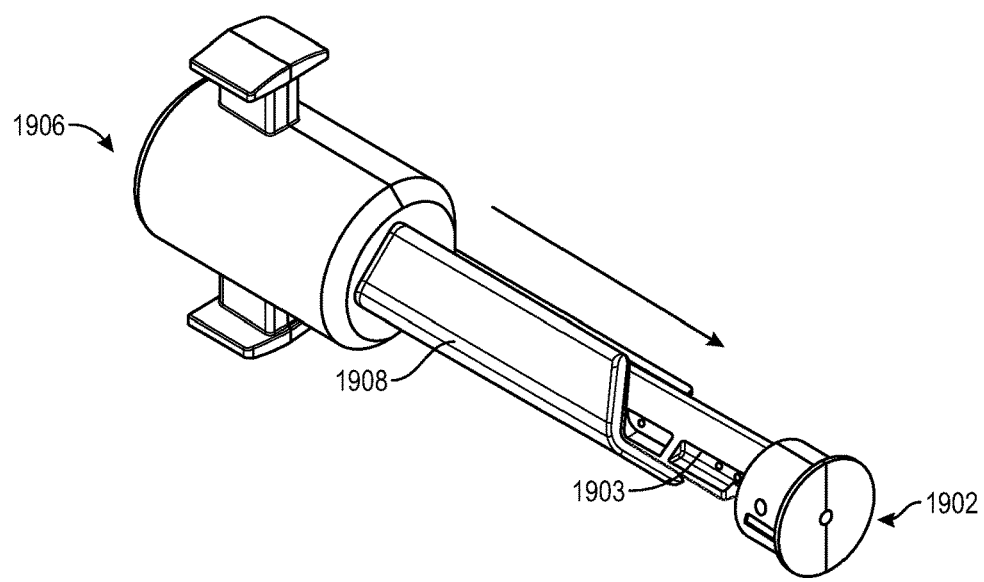

FIGS. 20F-20H are isometric views of the shuttle assembly 1906 and the first gear 1903 during alignment and engagement of the first gear 1903 and the second gear 1908 when the first gear 1903 and the second gear 1908 are initially out of alignment. Referring first to FIG. 20F, the shuttle assembly 1906 is translated proximally towards the first gear 1903. Next, as shown in FIG. 20G, the proximal end of the second gear 1908 meets the distal end of the first gear 1903 and the guide surfaces 1922, 1926 contact the distal end of the first gear 1903. As the shuttle assembly 1906 is further translated, the first gear 1903 is rotated into proper orientation. Once in proper alignment, further translation of the shuttle assembly 1906 results in insertion of the first gear 1903 into the second gear 1908 and engagement of the first gear 1903 with the second gear 1908, as shown in FIG. 20H.

Figure 21:
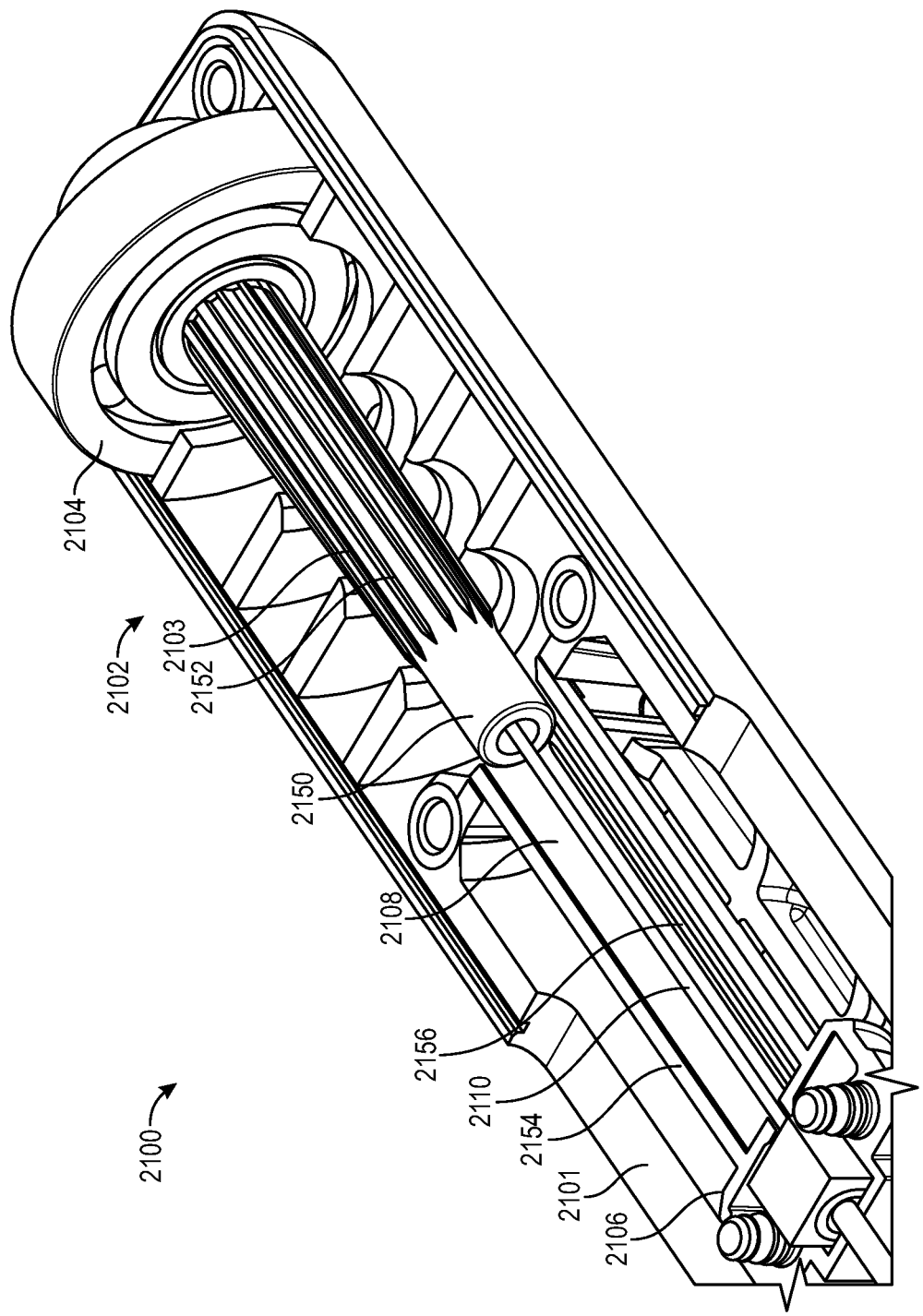
FIG. 21 is an isometric view of an alternative handle including a torsion relief mechanism.

FIG. 21 is an isometric view of an alternative embodiment of a handle 2100 according to the present disclosure. The handle 2100 includes a housing 2101 that is partially removed. Similar to the handle 1900 illustrated in FIGS. 19A-20H, the handle 2100 includes a torsion release assembly 2102 including a first gear 2103 supported by a rotational mount 2104, such as a ball bearing. The first gear 2103 is coupled to a snare 2110 or similar retrieval feature such that rotation of the first gear 2103 results in rotation of the snare 2110. The handle 2100 further includes a shuttle assembly 2106 that is rotationally fixed to the housing 2101 and that includes a second gear 2108. The shuttle assembly 2106 is translatable along the housing 2101 between a first shuttle position in which the first gear 2103 is disengaged from the second gear 2108 and a second shuttle position In which the first gear 2103 is engaged with the second gear 2108.

Engagement between the first gear 2103 and the second gear 2108 is achieved by corresponding splines extending longitudinally along each of the first gear 2103 and the second gear 2108. As illustrated in FIG. 21, for example, the first gear 2103 may include a first gear shaft 2150 and multiple first splines, such as first spline 2152, arranged circumferentially about the first gear shaft 2150. The second gear 2108 includes a tubular body 2154 defining a channel into which the first gear shaft 2150 is inserted when the shuttle 2106 is disposed in the second shuttle position. The second gear 2108 further includes at least one second spline 2156 extending inwardly from the tubular body 2154 such that as the first gear shaft 2150 is inserted into the tubular body 2154, the second spline 2156 is inserted between an adjacent pair of the first splines 2152. As a result, the first gear 2103 and the second gear 2108 become rotationally coupled and subsequent rotation of the handle 2100 rotates the snare 2110.

F. Docking Cap for Leadless Pacemaker Retrieval

As previously described in the context of FIGS. 4A-4G, retrieval of a leadless pacemaker or similar implantable medical device generally includes coupling the leadless pacemaker and docking the leadless pacemaker to a docking cap. To do so, a snare, tether, lasso, or similar retrieval feature mechanism is extended from a retrieval catheter and coupled to an attachment feature, such as an attachment button, of the leadless pacemaker. Once coupled, the retrieval feature is proximally retracted, thereby docking the leadless pacemaker within the docking cap.

Figure 22B:
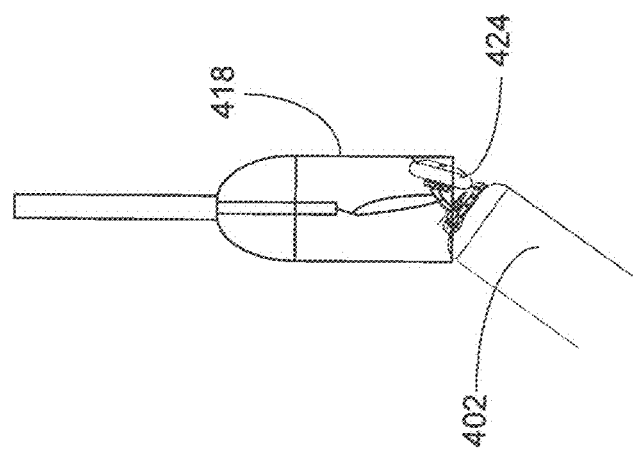
FIGS. 22A-22B are top views of a distal end of a catheter retrieval system during capture and docking of a leadless pacemaker.
Figure 22A:
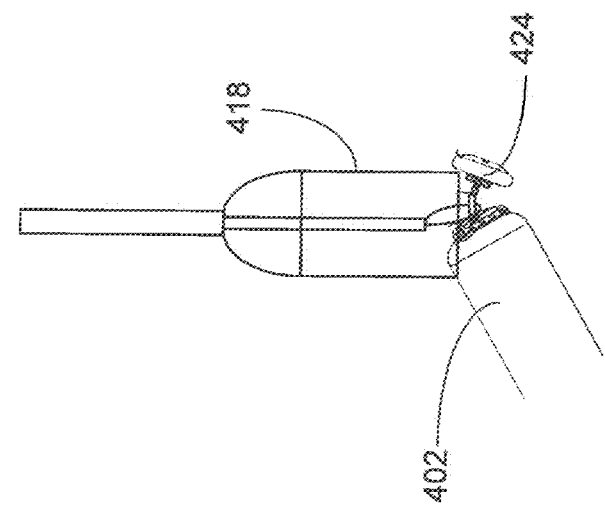

With conventional leadless pacemakers and retrieval systems, the foregoing capture and docking process generally requires that the leadless pacemaker and docking cap be substantially aligned as the leadless pacemaker is drawn into the docking cap. If such alignment does not occur, interference between the attachment feature and the docking cap may occur, preventing complete docking of the leadless pacemaker. For example, as illustrated in FIG. 22A, the retention feature 424 may interfere with a leading edge of the docking cap 418 or, as illustrated in FIG. 22B, the retention feature 424 may enter the docking cap 418 at an angle such that the retention feature 424 obstructs entry of the leadless pacemaker 402 into the docking cap 418. Accordingly, if alignment between the leadless pacemaker 402 and the docking cap 418 is not sufficient, a failed docking interface may result which necessitates another docking attempt. In certain conventional systems, an acute angle between the leadless pacemaker 402 and the docking cap 418 maybe avoided by applying tension to the leadless pacemaker 420 following capture and prior to docking. However, applying such tension risks damage to the tissue in which the leadless pacemaker 402 is implanted and undue strain on the snare and retention feature 424 which may lead to breakage of either the snare or the retention feature 424. Repeated docking and tension on the system may also induce additional stress on the heart wall during the retrieval procedure.

In light of the foregoing, the current disclosure is directed to a docking cap having improved docking and, in particular, a docking cap that reduces the degree of alignment required between the docking cap and proximal end of the leadless pacemaker for successful docking.

The docking cap disclosed herein includes various features directed to improved docking between the docking cap and a leadless pacemaker or similar implantable medical device. In contrast to the edge of conventional docking cap designs, the docking cap includes a profiled distal end that guides a retention feature of a leadless pacemaker into the internal volume defined by the docking cap. Once the retention feature is disposed within the internal volume, interference between the retention feature and the docking cap is reduced by cutouts or openings disposed about the docking cap. Such cutouts enable the retention feature to travel outside the internal volume of the docking cap during docking, reducing the likelihood that the retention feature will become jammed within the docking cap and prevent docking of the leadless pacemaker. In certain implementations, a flexible sheath is disposed about the openings such that the retention feature is able to travel outside the envelope of the docking cap, but the sheath maintains an inward force on the retention feature such that the retention feature is biased towards the internal docking cap volume. By doing so, the likelihood that the retention feature will become lodged or otherwise interfere with structural features of the docking cap is reduced.

Figure 22C:
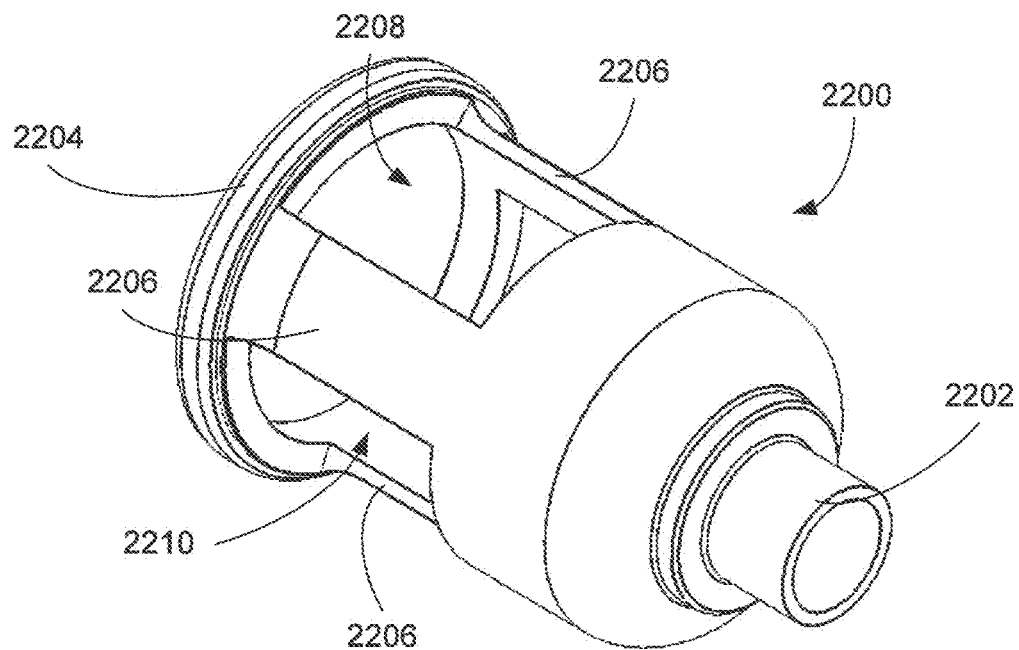
FIGS. 22C-22D are isometric views of a docking cap for use with a retrieval system.
Figure 22D:
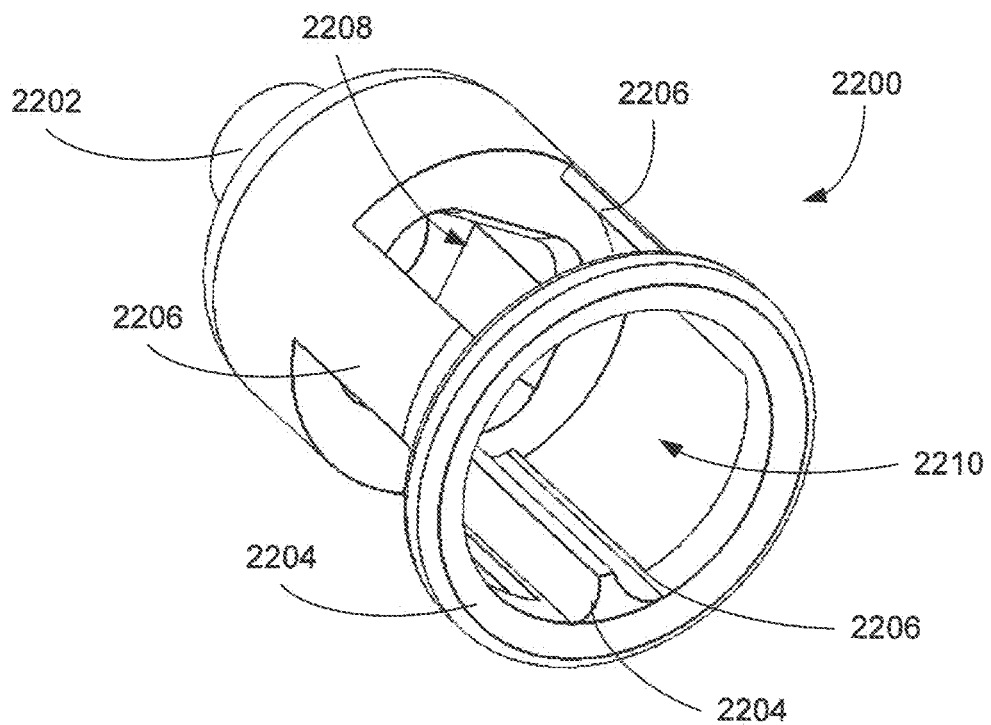
Figure 22E:
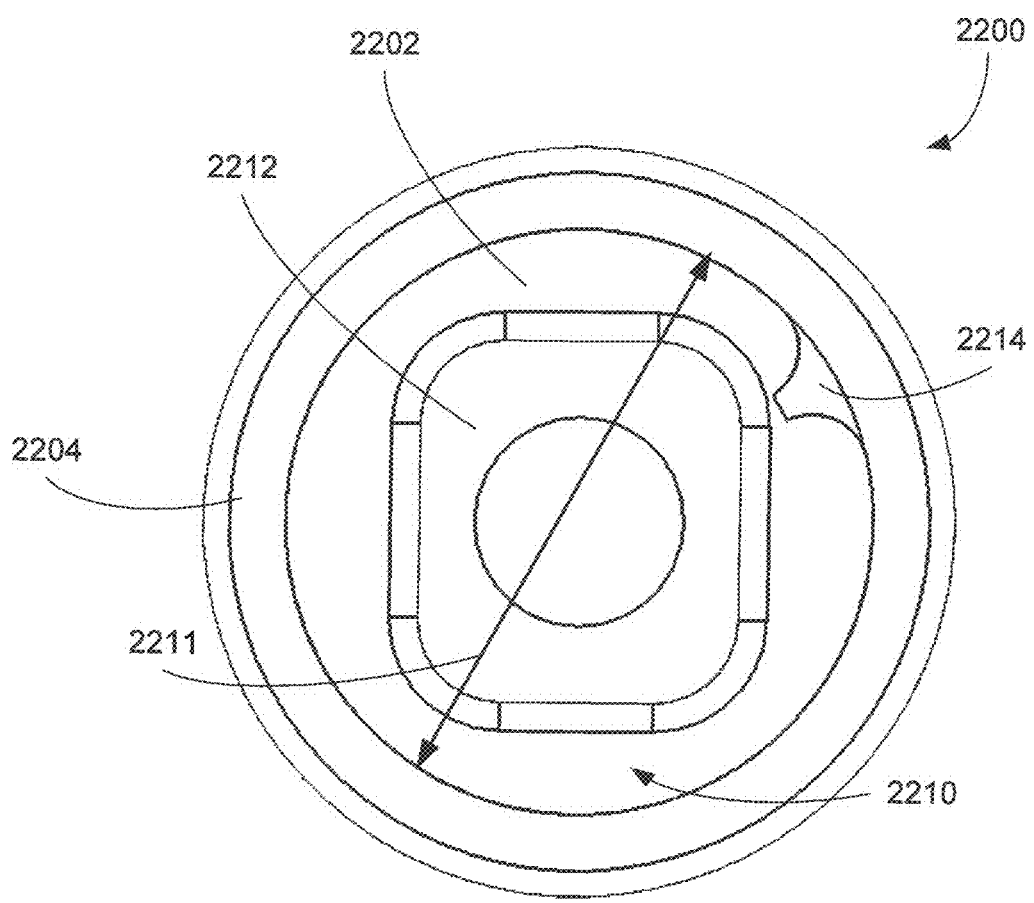
FIG. 22E is an end view in a proximal direction of the docking cap of FIGS. 22C-22D.

FIGS. 22C and 22D are isometric views of a docking cap 2200 in accordance with the present disclosure. FIG. 22E is a bottom view of the docking cap 2200. In general, the docking cap 2200 forms a cage-like structure defining an internal docking cap volume 2210 adapted to receive the proximal end of a leadless pacemaker or similar implantable medical device. The docking cap 2200 includes a proximal cap end 2202 adapted to be coupled to the retrieval catheter shaft and a distal annulus 2204 disposed opposite the proximal cap end 2202. As shown in FIG. 22E, the proximal cap end 2202 may define a receptacle 2212 shaped to receive a drive gear during retrieval of the leadless pacemaker. In certain implementations, the docking cap 2200 may be formed using at least one of stainless steel (such as 304 stainless steel), titanium, and a polymer, such as polyether ether ketone (PEEK). In certain implementations, the material used to form the docking cap 2200 may be loaded with a radiopaque additive or otherwise visible using fluoroscopy or a similar imaging technique.

As shown in FIG. 22E, the internal docking cap volume 2210 may have an internal diameter 2211. In certain implementations, the internal diameter may be from and including 0.200 inches to and including 0.250 inches and may be depend on the size of the introducer or catheter to which the docking cap 2200 is coupled. In conventional docking caps, docking of the leadless pacemaker and its retention feature is generally limited by the internal diameter 2211 of the internal docking cap volume 2210. However, referring back to FIGS. 22C-D, docking caps according to the present disclosure include longitudinal members 2206 extending between the proximal cap end 2202 and the distal annulus 2204 to define openings, such as opening 2208, between adjacent longitudinal members 2206. The openings 2208 are sufficiently sized to allow the proximal end of a leadless pacemaker and, in particular, the coupling feature disposed at the proximal end of the leadless pacemaker to pass at least partially through the openings 2208 during the capture and retrieval processes, thereby expanding the effective diameter of the docking cap beyond the internal diameter 2211.

To accommodate the proximal end of the leadless pacemaker and/or the coupling feature of the leadless pacemaker, the longitudinal members 2206 are generally disposed about the docking cap 2200 such that the minimum distance between adjacent longitudinal members 2206 is greater than the width of the proximal end of the leadless pacemaker and/or the coupling feature of the leadless pacemaker. Accordingly, while illustrated in FIGS. 22C-22E as including three longitudinal members 2206 and three corresponding openings defined between the longitudinal members, other docking caps in accordance with this disclosure may have more or fewer longitudinal members 2206 and corresponding openings provided they can accommodate the leadless pacemaker of the particular application.

In certain implementations, a torque transmission feature 2214 may be coupled to one of the longitudinal members 2206 and extend into the docking cap volume 2210. The torque transmission feature 2214 is positioned and shaped such that after docking of the leadless pacemaker, rotation of the docking cap 2200 causes the torque transmission feature 2214 to contact the docked leadless pacemaker and transmit torque from the docking cap 2200 to the leadless pacemaker such that the leadless pacemaker may be unscrewed from tissue.

Figure 22F:
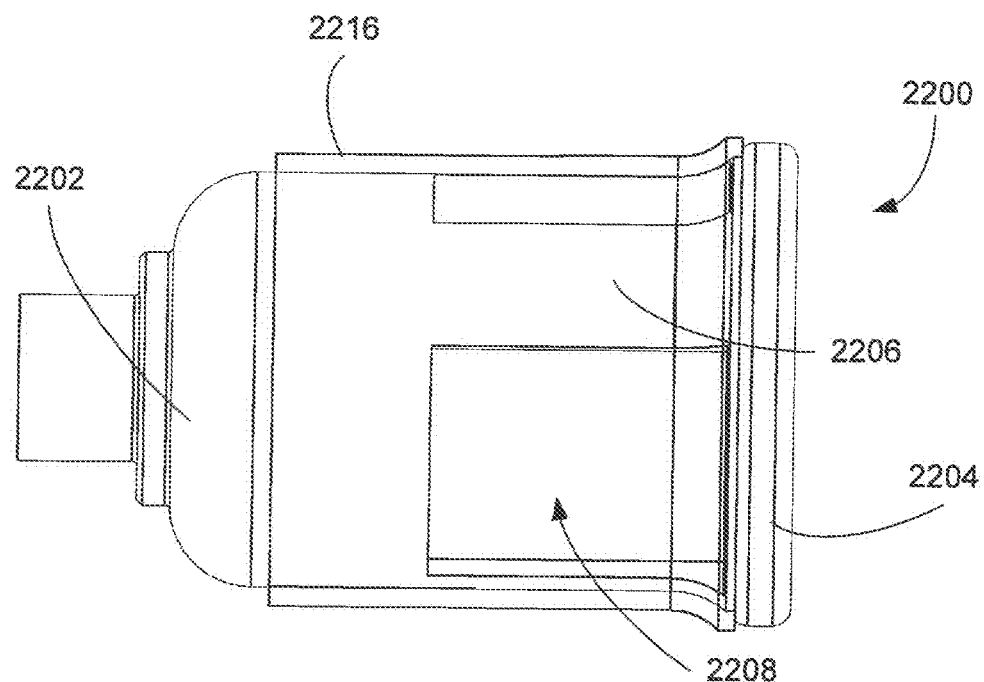
FIGS. 22F-22G are a side view and a side cross-sectional view of the docking cap of FIGS. 22C-22D.
Figure 22G:
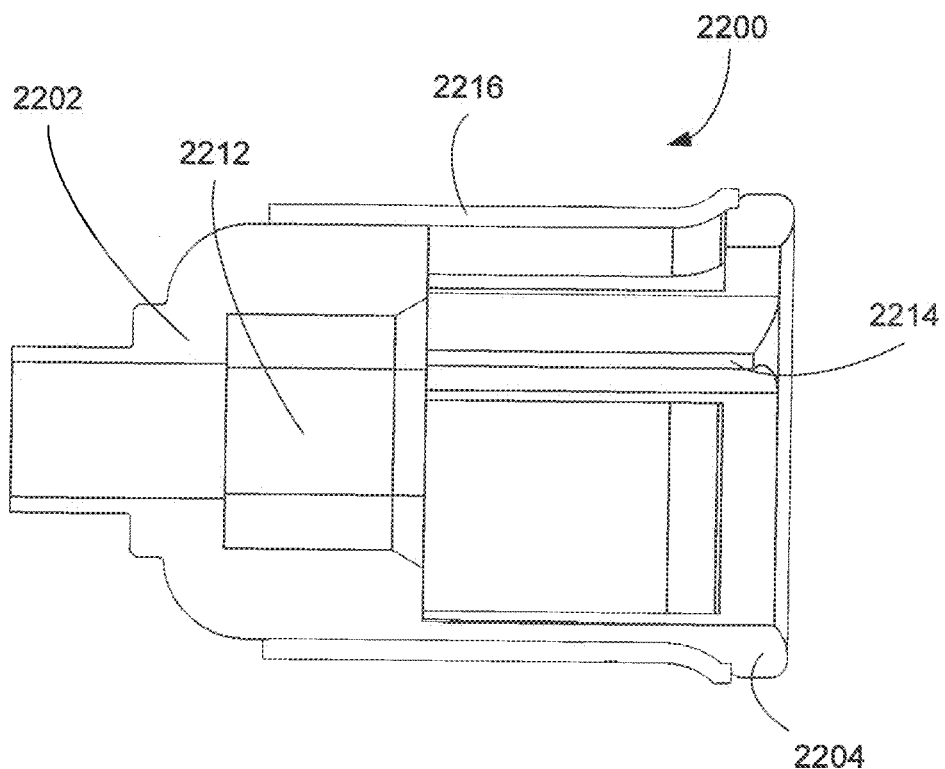

FIGS. 22F and 22G are a side view and a cross-sectional side view, respectively of the docking cap 2200. As shown in FIGS. 22F-22G, the docking cap 2200 may include a sheath 2216 disposed over a portion of the docking cap 2200 including the openings 2208. The sheath 2216 is generally formed from an elastic material. By doing so, the sheath 2216 allows the retention feature of a leadless pacemaker to extend through the openings 2208 while maintaining inward pressure that biases the retention feature into the internal docking cap volume 2210. As a result of the inward biasing provided by the sheath 2216, the retention feature is directed away from edges and other features of the docking cap 2200 on which the retention feature may become bound up. In addition to assisting during docking of a leadless pacemaker, the inward force provided by the sheath 2216 on the retention feature also facilitates alignment of the retention feature with the distal annulus 2204 should undocking of the leadless pacemaker be required.

In certain implementations, the sheath 2216 may be formed from one or more of a copolymer, polytetrafluoroethylene (PTFE), and perfluoroalkoxy alkane (PFA) and may have a thickness from and including 0.006 inches to and including 0.020 inches. For example, in one implementation, the sheath 2216 is formed from a fluorinated ethylene propylene (FEP) sheet having a thickness of 0.012 inches that is applied to the docking cap 2200 by heat shrinking the FEP sheet onto the outside surface of the docking cap 2200.

Figure 22H:
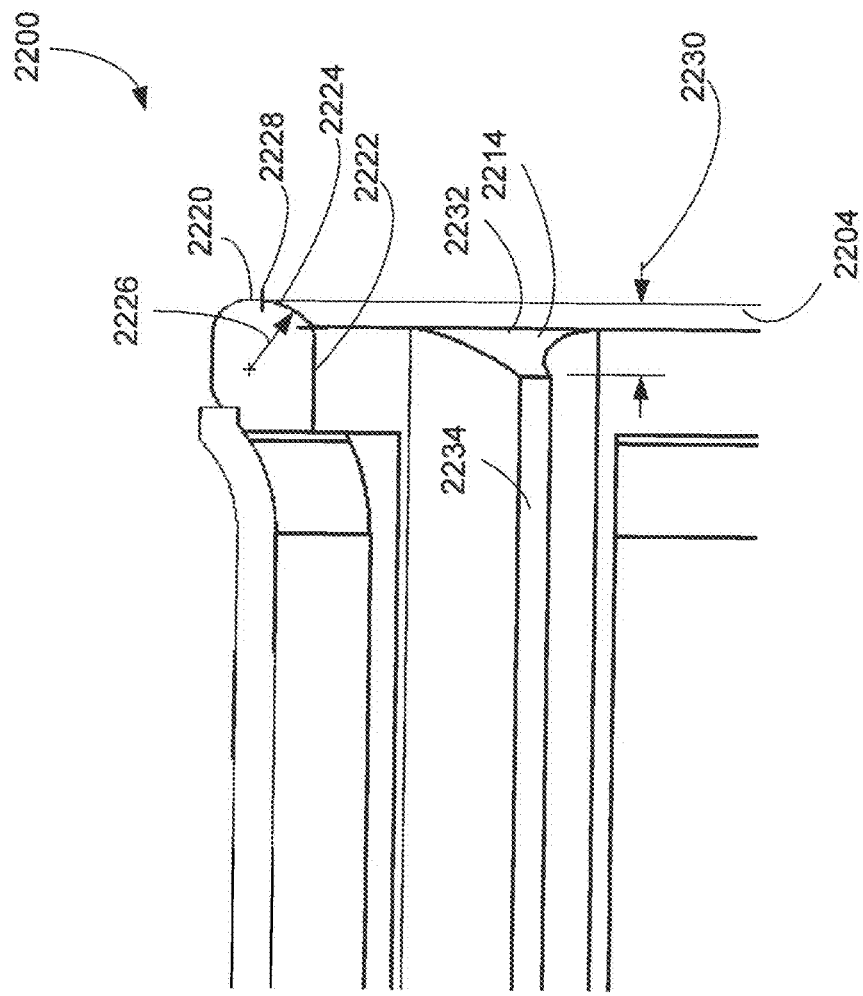
FIG. 22H is a side cross-sectional detail view of the docking cap of FIGS. 22C-22D.

FIG. 22H is a detailed view of the distal annulus 2204 of the docking cap 2200. In certain implementations, to facilitate entry of an implantable medical device, such as a leadless pacemaker, into the docking cap 2200 during the docking process, the distal portion of the distal annulus 2204 may be shaped to reduce edges on which the implantable medical device may become caught. For example, in certain implementations, the distal annulus 2204 may include a distal face 2220 and an internal surface 2222 substantially perpendicular to the distal face 2220. A curved transition 2224 may extend between the distal face 2220 and the internal surface 2222 to guide a captured implantable lead into the docking cap 2200 during the docking process. In certain implementations, the curved transition may have a radius of curvature 2226 from and including 0.017 inches to and including 0.150 inches and an arc length 2228 from and including 0.017 inches to and including 0.035 inches.

To further reduce the likelihood of the leadless pacemaker becoming caught at or near the distal annulus 2204, the torque feature 2214 may also be offset from the distal face 2220 of the distal annulus 2204. For example, the torque feature 2214 may originate from a proximal edge of the curved transition 2224 and include a concave scallop 2232 that terminates in a longitudinal face 2234. Accordingly, in certain implementations, the longitudinal face 2234 may have an offset 2230 from and including 0.065 inches to and including 0.120 inches relative to the distal face 2220.

G. Self-Aligning Drive Gear Assembly for Leadless Pacemaker Retrieval

As previously discussed in the context of FIGS. 4A-6B, retrieval of a leadless pacemaker or similar implantable medical device may be accomplished by snaring or otherwise capturing an attachment feature, such as a button, on the proximal end of the leadless pacemaker with a retrieval catheter, retracting the pacemaker into a docking cap, and unscrewing the pacemaker from the cardiac tissue.

Transmission of torque from the handle of the retrieval system to the docked pacemaker may be accomplished by a drive gear disposed on a distal end of the retrieval catheter or other torque shaft. More specifically, as the retrieval catheter or torque shaft is retracted during docking of the leadless pacemaker, the drive gear seats or otherwise engages with a corresponding feature of the docking cap. Once mated, rotation of the drive gear causes rotation of the docking cap, which transfers torque to unscrew the leadless pacemaker. Notably, if the drive gear does not properly engage with the docking cap, torque is not transmitted through the torque shaft as intended, but through the snare or other retrieval feature. Buildup of torque in the snare can lead to several unwanted events. For example, the snare may be permanently damaged and not function correctly, the snare could fracture, or the snare could cause the attachment feature of the pacemaker to detach and become embolic.

Conventional drive gear and docking cap arrangements require a precise fit and a specific orientation to mate and deliver torque. Due to tension in the torque cable and the geometry of the legacy components during docking, the drive gear does not self-align inside the docking cap recess if it is not correctly seated initially. Subsequently, the torque performance of the retrieval catheter suffers, In light of the foregoing, the present disclosure is directed to a docking cap and drive gear design with improved seating and interfacing between the docking cap and drive gear. As a result, drive gears and docking caps in accordance with the present disclosure provide more orientation options that still result in proper mating between the components and allow the drive gear to self-align and seat within the docking cap if perfect mating orientation is not initially achieved.

The drive gear and docking cap have been designed with geometry that encourages seating of the drive gear within the docking cap. Additionally, the interface between the drive gear and docking cap includes a limited number of interference points, thereby allowing more orientations for proper seating and fewer opportunities for interference which forfeits torque performance. Moreover, if the drive gear is initially drawn into the docking cap in an orientation that interferes with proper seating of the drive gear or in which the drive gear does not fully engage the docking cap, the drive gear self-aligns after torque is applied such that the drive gear seats within the docking cap and torque transfer performance is maintained.

The docking cap geometry has been designed to work in tandem with the drive gear to facilitate self-alignment between the components. The docking cap recess, which receives the drive gear, is generally deep enough to maintain and transmit torque should an interference configuration be achieved. Also, at least a portion of the recess is shaped to avoid interference with the drive gear after the drive gear has been retracted into the docking cap. As a result, the drive gear may be rotated within the recess to facilitate self-alignment.

FIGS. 23A-23E illustrate general operation of a docking system 2300 in accordance with the present disclosure. The docking system 2300 includes a drive gear 2302 disposed on the end of a torque shaft 2304 or retrieval catheter. The torque shaft 2304 extends through a docking cap 2306 and is translatable relative to the docking cap 2306. As previously discussed in the context of FIGS. 4A-6B, the docking cap 2306 may be disposed at a distal end of a catheter shaft and, in certain implementations, may be coupled to the distal end of the catheter shaft using a rotatable coupling such that the docking cap 2306 is able to rotate relative to the catheter shaft. The docking cap 2306 may, but does not necessarily include the various docking cap features previously discussed in the context of FIGS. 22C-H.

Figure 23A:
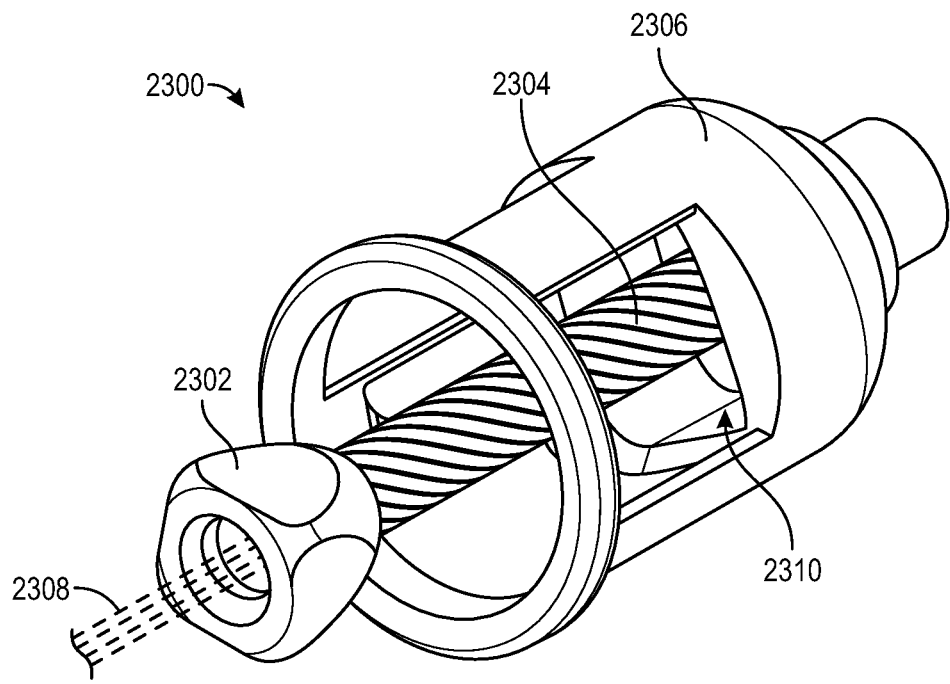
FIGS. 23A-23C are isometric views of a docking system at different stages of a docking operation.

A retrieval feature 2308 (shown in FIG. 23A in dashed lines for clarity) generally extends through the torque shaft 2304 such that the retrieval feature may be used to capture a corresponding attachment feature of a leadless pacemaker or other implantable medical device. To facilitate such capture, the torque shaft 2304 may be extended from the docking cap as illustrated in FIG. 23A.

Figure 23B:
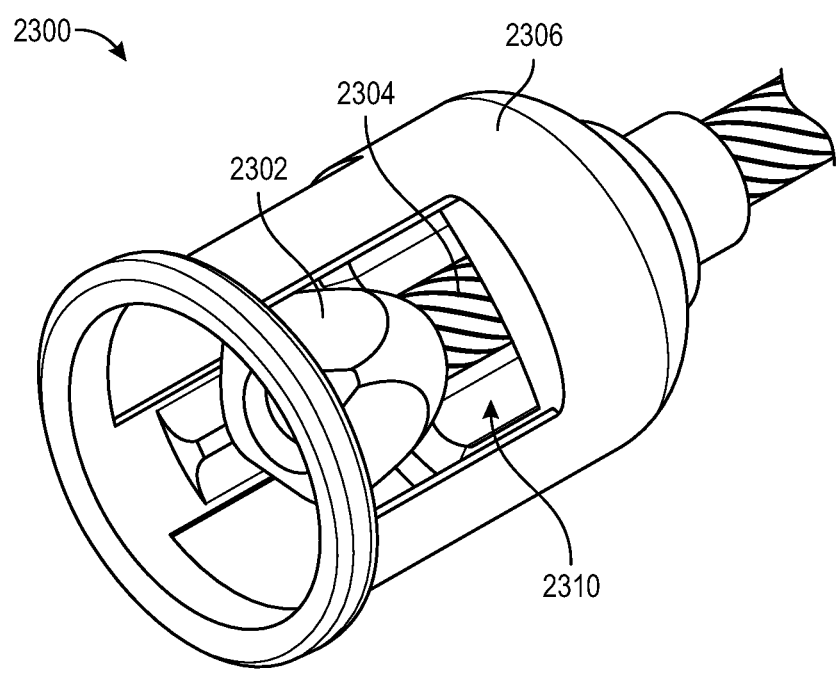
Figure 23C:
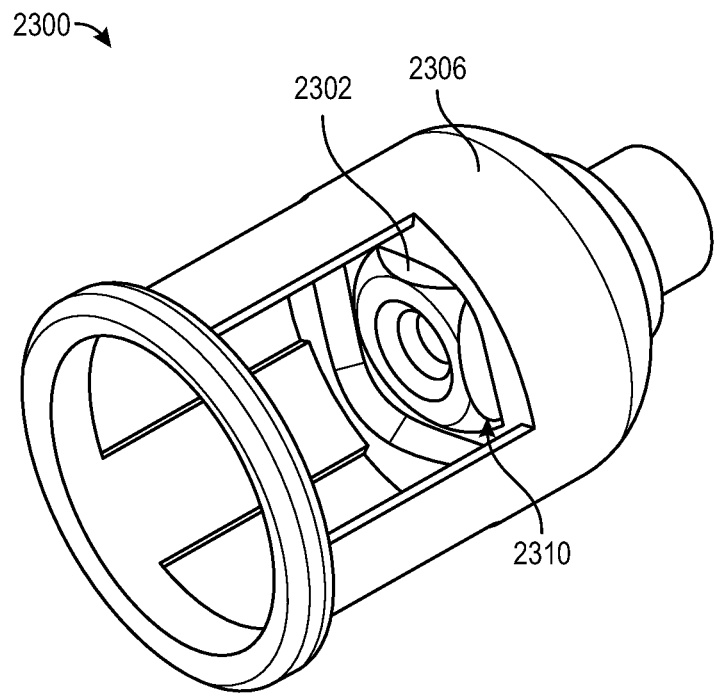

As shown in FIG. 23B, following capture of the leadless pacemaker, the torque shaft 2304 is retracted into the docking cap 2306 to dock the leadless pacemaker. FIG. 23C illustrates the torque shaft 2304 in a fully retracted position such that the drive gear 2302 is retained within a recess 2310 defined within the docking cap 2306.

Figure 23D:
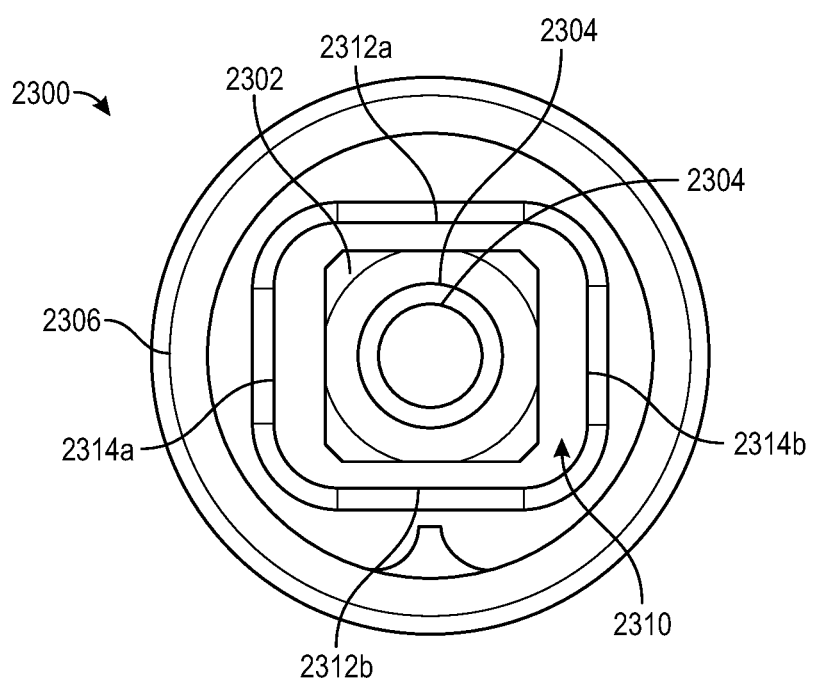
FIG. 23D-23E are end views in a proximal direction of the docking system illustrating a drive gear in a disengaged and engaged configuration with a docking cap, respectively.
Figure 23E:
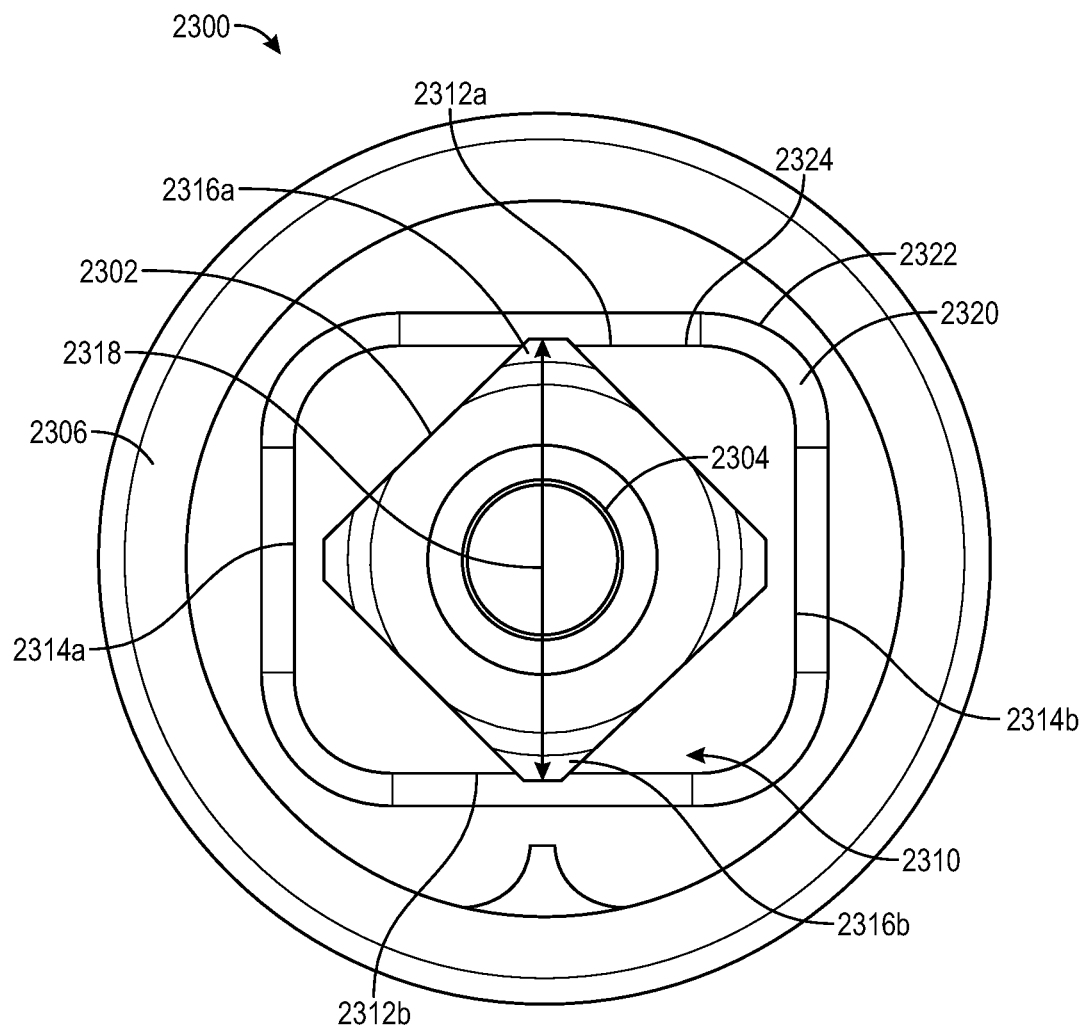

As shown in FIG. 23D, the recess 2310 may, in certain implementations, be substantially rectangular in shape such that the recess 2310 is defined by a first pair of long opposing walls 2312a, 2312b arranged perpendicular to each of a second pair of shorter opposing walls 2314a, 2314b. The dimensions and spacing of the first pair of opposing walls 2312a, 2312b and the second pair of opposing walls 2314a, 2314b is generally dependent on the size and shape of the drive gear 2302 in order to facilitate self-alignment of the drive gear 2302 and the docking cap 2306. As illustrated by the arrangement of FIG. 23D, the drive gear 2302 may be retracted into the recess 2310 in an orientation in which the drive gear 2302 does not interfere with the docking cap 2306. However, as illustrated in FIG. 23E, the drive gear 2302 may be rotated relative to the docking cap 2306 such that the drive gear 2302 interferes with the first pair of opposing walls 2312A, 2312B, thereby enabling torque transfer from the torque shaft 2304 to the docking cap 2306. As a result, the drive gear 2302 may be retracted into the recess 2310 of the docking cap 2306 in any orientation relative to the docking cap 2304 and may become properly seated for torque transfer by simply rotating the torque shaft 2304 and the drive gear 2302.

Once seated, further rotation of the drive gear 2302 by rotation of the torque shaft 2304 results in rotation of the docking cap 2306. Such further rotation may be used to unscrew a leadless pacemaker or other implantable medical device from tissue or perform other functions. In certain implementations, the drive gear 2302 may be adapted to be disengaged from the docking cap 2306 by rotating the drive gear 2302 in a direction opposite that used to engage the drive gear 2302 and the docking cap 2306. More specifically, counter-rotation of the drive gear 2302 within the docking cap 2306 may eliminate the interference between the drive gear 2302 and the docking cap 2306 such that the drive gear 2302 may be distally extended from the docking cap 2306 or otherwise moved independently from the docking cap 2306.

In the example implementation of FIGS. 23A-23E, the drive gear 2302 and recess 2310 are shaped such that interference occurs between each of the first pair of opposing walls 2312A, 2312B and opposite corners 2316A, 2316B (shown in FIG. 23E) of the drive gear 2302. Accordingly, the opposite corners 2316A, 2316B function as torque features of the drive gear 2302 adapted to engage corresponding recess torque features (here, the first pair of opposing walls 2312A, 2312B) of the docking cap 2306 to transfer torque from the torque shaft 2304 to the docking cap 2306. To achieve this result, each of the first pair of opposing walls 2312A, 2312B have a length that is greater than the maximum width of the drive gear 2302 (which, in the current example is a diagonal distance 2318 between the opposite corners 2316A, 2316B) and each of the second pair of opposing walls 2314A, 2314B has a length that is less than the maximum width of the drive gear 2302.

As shown in FIG. 23E, the recess 2310 may also have a lip 2320 that transitions from a first perimeter 2322 having short sides that exceed the maximum width of the drive gear 2302 to a second perimeter 2324 defined by the second pair of opposing walls 2314a, 2314b. As a result, the lip 2320 further guides the drive gear 2302 into the recess 2310 such that proper alignment occurs between the drive gear 2302 and the docking cap 2306. As illustrated in FIG. 23C, the drive gear 2302 may be shaped to at least partially extend beyond the lip 2320 when the drive gear 2302 is received within the recess 2306.

Figure 24:
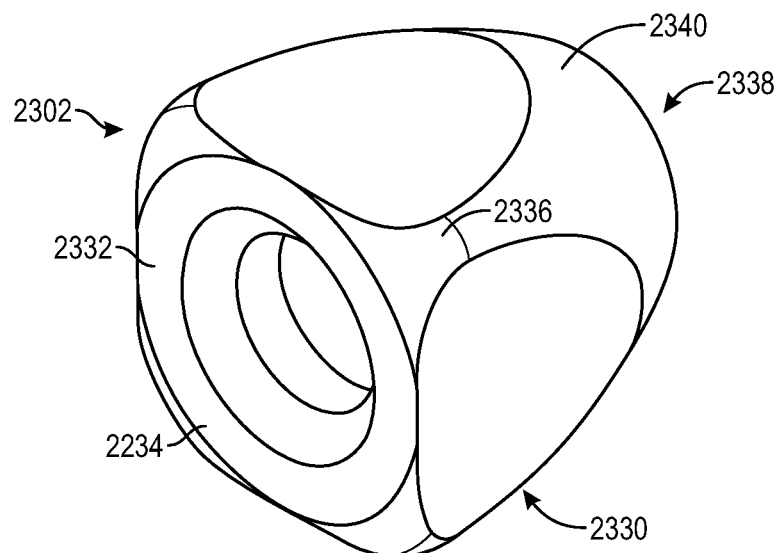
FIG. 24 is an isometric view of the drive gear of FIGS. 23A-23E.
Figure 25:
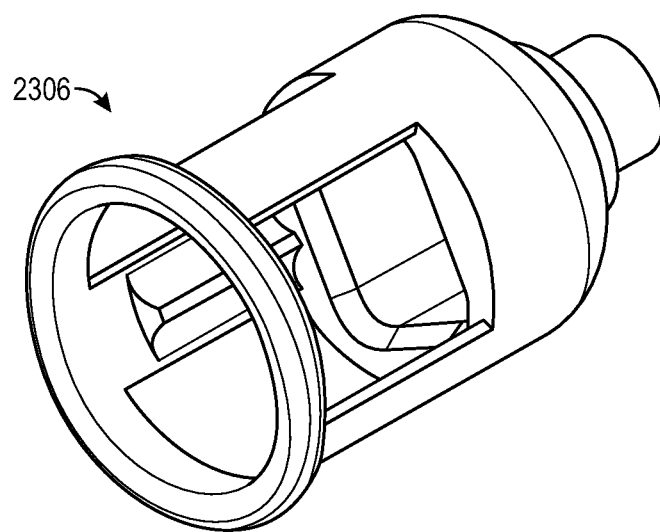
FIG. 25 is an isometric view of the docking cap of FIGS. 23A-23E.

FIG. 24 and FIG. 25 are isometric views of the drive gear 2302 and the docking cap 2306 of the docking system 2300, respectively. As illustrated in FIG. 24, the drive gear 2302 includes a distal portion 2330 including a cuboid body 2332 having a substantially square distal shape 2334. The cuboid body 2332 may include distal rounded corners 2336 shaped to engage the recess 2310 when the drive gear 2302 is retracted into the docking cap 2306. The drive gear 2302 may further include a proximal portion 2338 including a proximally tapering body 2340, which enables easier initial insertion of the drive gear 2302 into the recess 2310 and facilitates alignment of the drive gear 2302 with the docking cap 2306.

Figure 26:
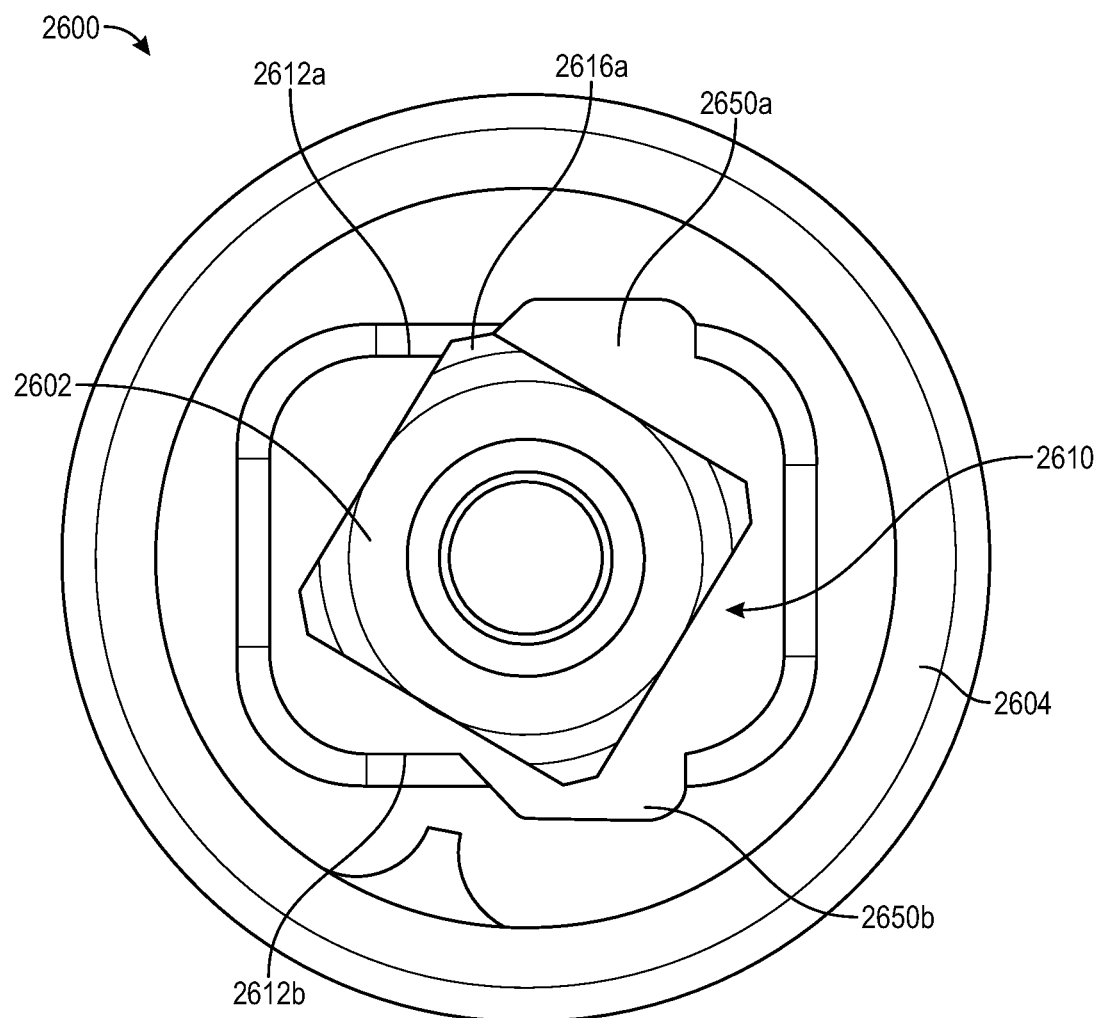
FIG. 26 is an end view in a proximal direction of an alternative docking system.

FIG. 26 illustrates an alternative implementation of a docking system 2600 including a drive gear 2602 engaged with a docking cap 2602. Similar to the drive gear 2302 and the docking cap 2306 as illustrated in FIG. 23E, the docking cap 2602 includes a recess 2610 shaped to receive the drive gear 2602. Once received, the drive gear 2602 may be rotated such that a corner 2616a of the drive gear engages a wall 2612a of the recess 2610, thereby enabling transfer of torque applied to the drive gear 2602 to the docking cap 2606. In contrast to the docking cap 2306 of FIG. 23E, the docking cap 2606 defines a pair of cutouts 2650a, 2650b extending into each of the wall 2612a and an opposite wall 2612b, respectively. The cutouts 2650a, 2650b are arranged such that interference between the drive gear 2602 and the docking cap 2606 occurs at only one point, thereby enabling self-alignment of the drive gear 2602 relative to the docking cap 2606 by application of torque to the drive gear 2602. Accordingly, in the implementation of FIG. 26, the corner 2616a functions as a torque feature of the drive gear 2602 that engages a corresponding recess torque feature in the form of the portion of the wall 2612a adjacent the cutout 2650a.

Figure 27:
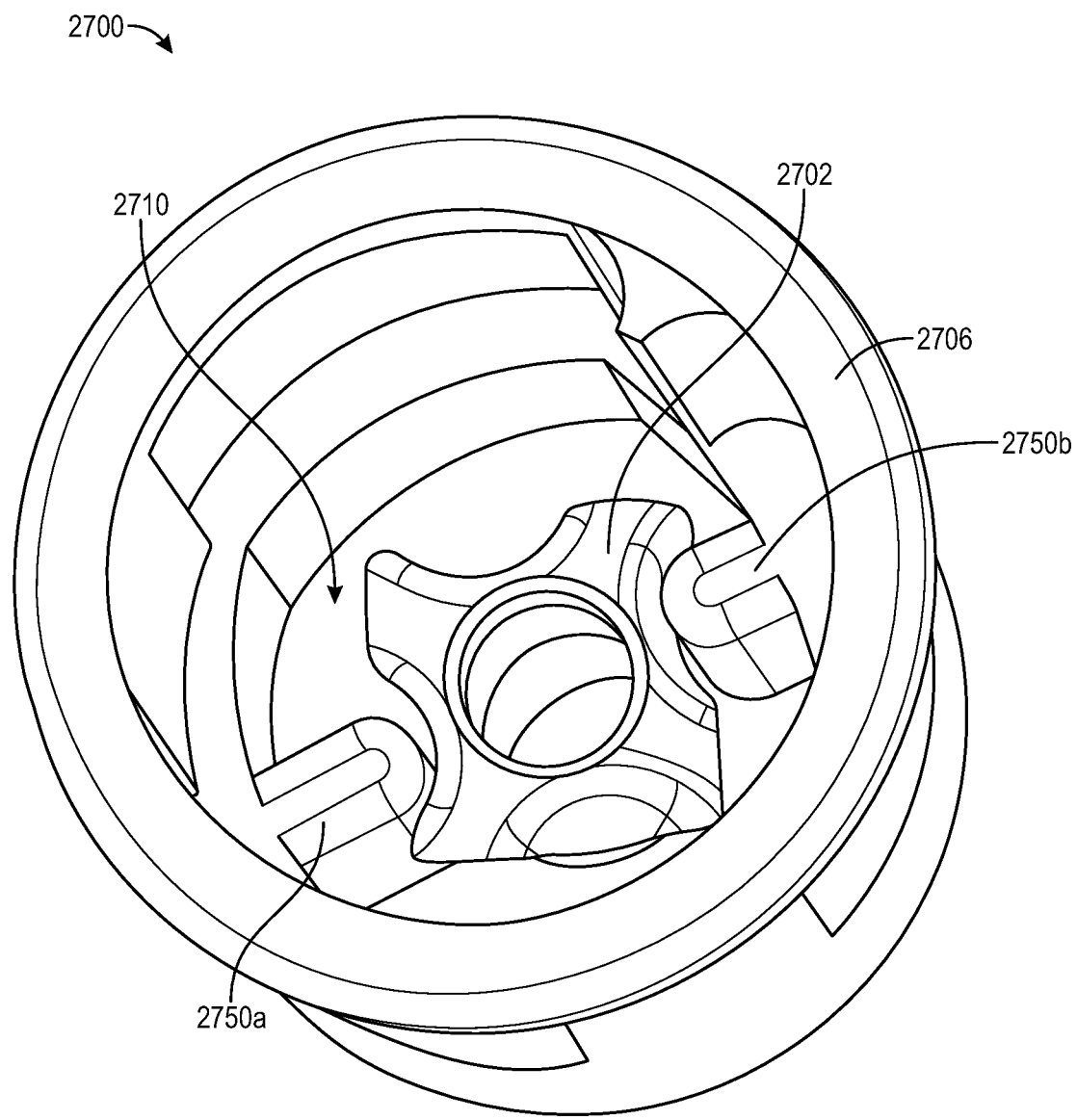
FIG. 27 is an isometric view of a second alternative docking system.
Figure 28:
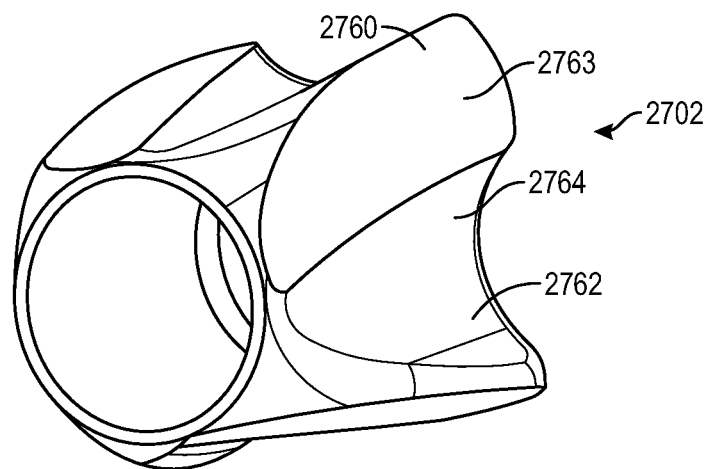
FIG. 28 is an isometric view of a drive gear of the second alternative docking system of FIG. 27.
Figure 29:
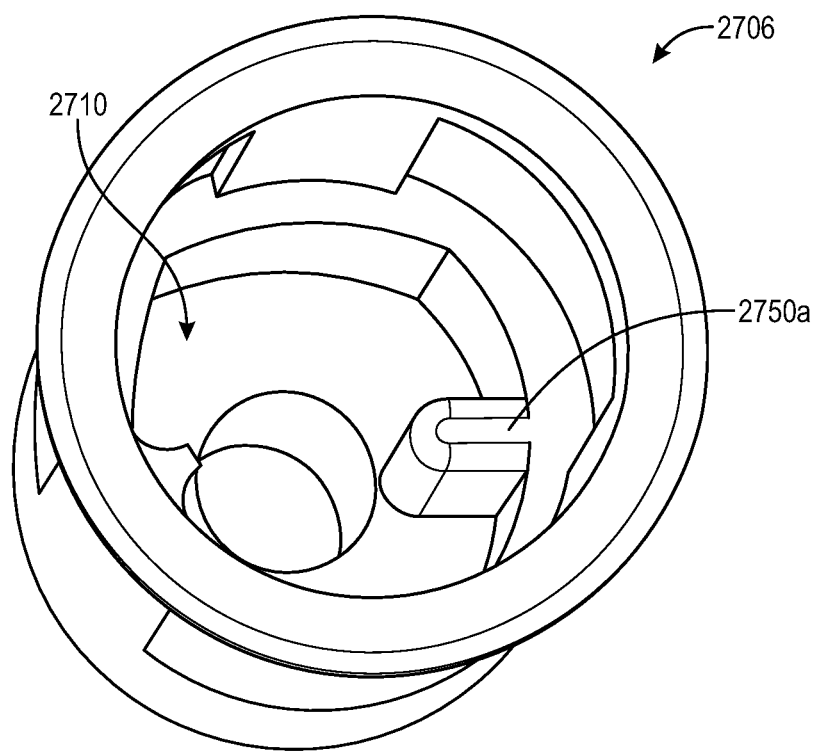
FIG. 29 is an isometric view of a docking cap of the second alternative docking system of FIG. 27.

FIGS. 27-29 illustrate another alternative implementation of a docking system 2700 including a drive gear 2702 and a docking cap 2706 in accordance with the present disclosure. As illustrated in FIGS. 27 and 29, the docking cap 2706 defines a recess 2710 and further includes protrusions 2750a, 2750b that extend laterally from the docking cap 2706 into the recess 2710.

In contrast to the square-shaped drive gears 2302. 2602 illustrated in FIGS. 23-26, the drive gear 2702 of the docking system 2700 is formed to have a star-shaped design. Referring to FIG. 28, which is an isometric view of the drive gear 2702, the drive gear 2702 includes an outer face 2760 including multiple concave sections, such as concave section 2762. The concave section 2762 is shaped to receive the protrusions 2750a, 2750b as the drive gear 2702 is rotated within the recess. The concave section 2762 is connected to a substantially flat portion 2763 of the outer face 2760 by a transition portion 2764. The flat portion 2763 and the transition portion 2764 are positioned relative to the concave section 2762 such that when one of the protrusions 2750a, 2750b is received by the concave section 2762, further rotation of the drive gear 2702 results in interference between the protrusion and the transition portion 2764. Accordingly, the transition portion 2764 functions as a torque feature that transfers torque from the drive gear 2702 to a corresponding recess torque feature in the form of one of the protrusions 2750a, 2750b of the docking cap 2706.

Figure 30A:
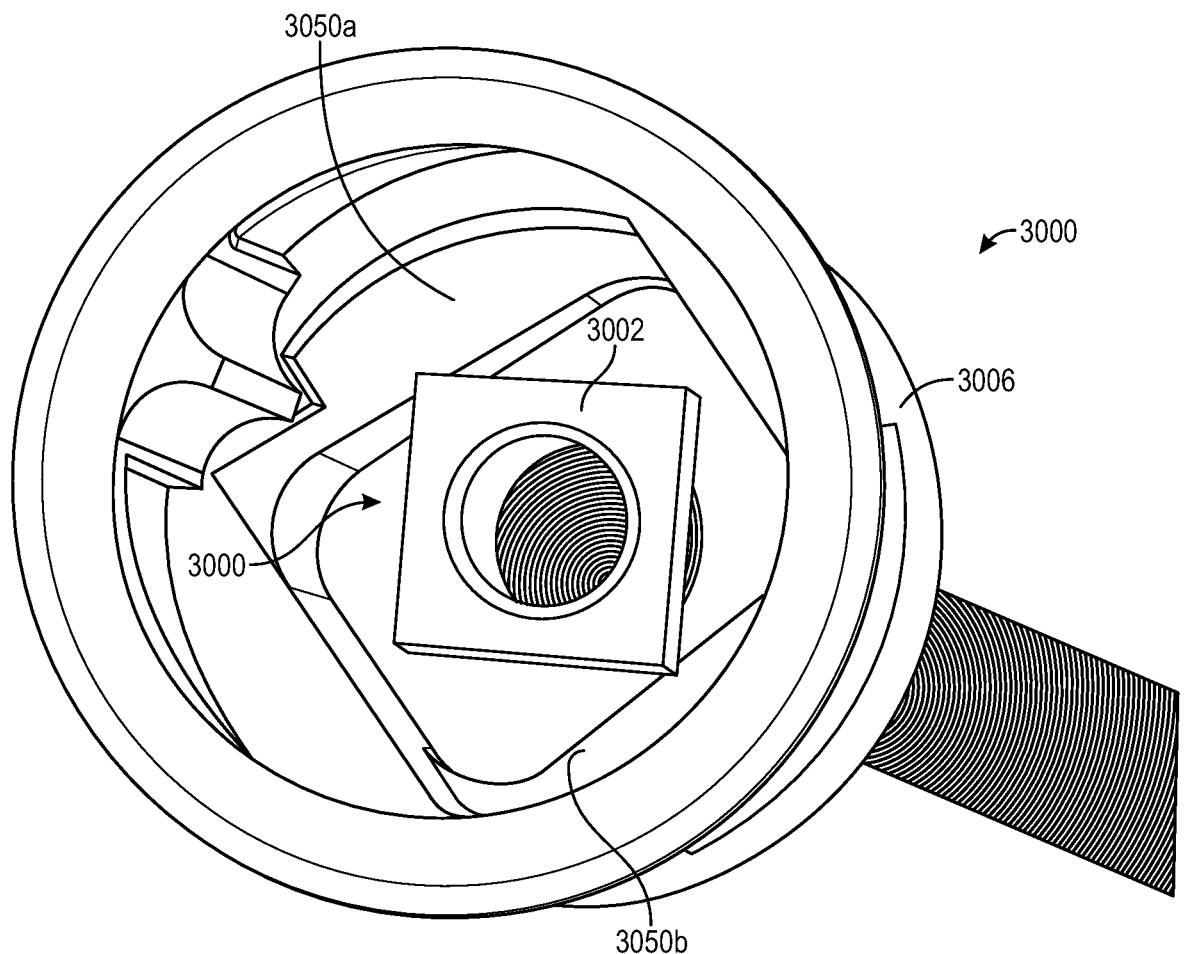
FIG. 30A is an isometric view of a third alternative docking system.
Figure 30B:
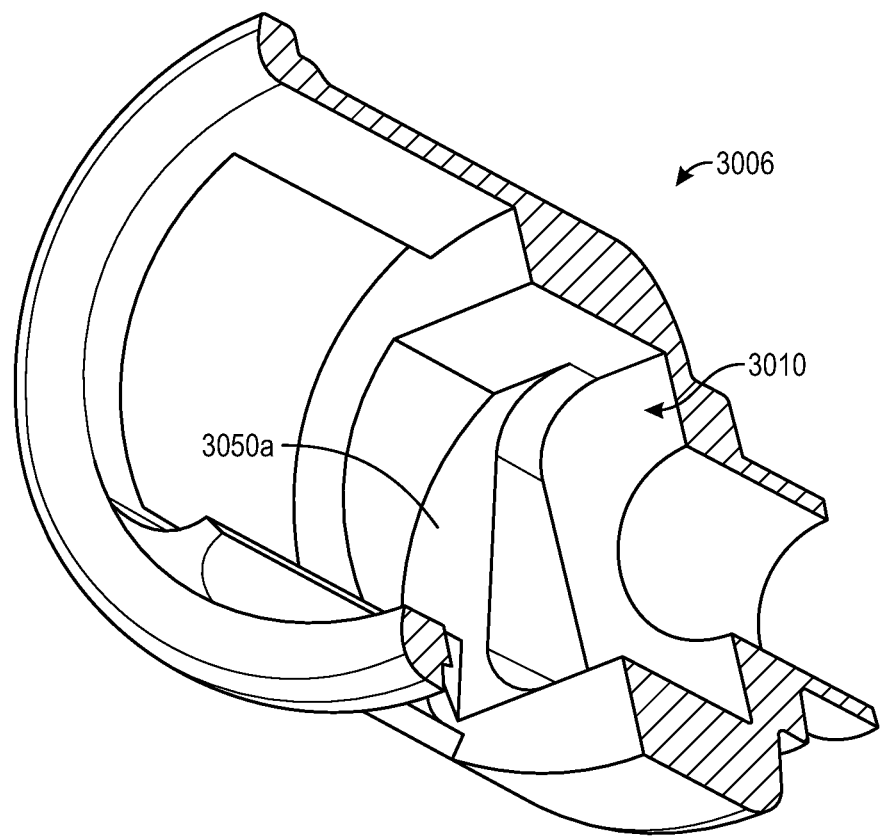
FIG. 30B is an isometric cross-sectional view of a docking cap of the third alternative docking system of FIG. 30.

FIGS. 30A and 30B illustrate yet another implementation of a docking system 3000 according to the present disclosure. As illustrated in FIG. 30A, which is an isometric view of the docking system 3000, the docking system 3000 includes a drive gear 3002 that is retractable into a recess 3010 of a docking cap 3006. The drive gear 3002 may be shaped as previously described such that when retracted within a recess 3010 of the docking cap 3006, the drive gear 3002 may be rotated to engage the docking cap 3006 such that torque applied to the drive gear 3002 by the torque shaft 3004 is transferred to the docking cap 3006.

Referring back to FIGS. 23D and 23E, the recess 2310 of the previously described docking cap 2306 was defined by a substantially flat bottom surface from which the walls defining the recess 2310 extended in a substantially perpendicular direction. In contrast, the docking cap 3006 includes proximally slanted surfaces 3050a, 3050b that extend along the depth of the recess 3010. One such slanted surface 3050a is more clearly visible in FIG. 30B, which is an isometric cross-sectional view of the docking cap 3006. During operation, the slanted surfaces 3050a, 3050b guide the drive gear 3002 to seat within the docking cap 3006 in response to both proximal puffing and rotation applied to the drive gear 3002. Once seated, the drive gear 3002 may engage the docking cap 3006 as previously described. For example, in certain implementations, a corner of the drive gear 3006 may interfere with a wall defining the recess 3010 or the drive gear 3006 may include concave surfaces adapted to receive and engage protrusions extending into the recess 3010.

H. Expandable Sleeve for Leadless Pacemaker Delivery and Retrieval

The delivery and retrieval systems in accordance with this disclosure may also include atraumatic tip configurations that can be extended over the leadless pacemaker and primary fixation mechanism when the leadless pacemaker is being delivered into, or withdrawn from, the patient. The atraumatic tip configurations can also be retracted from about the leadless pacemaker and primary fixation mechanism when the primary fixation mechanism is caused to displace relative to the heart tissue such as when the primary fixation mechanism is in the form of a helix and is screwed into or out of the heart tissue at an implantation site.

Figure 31:
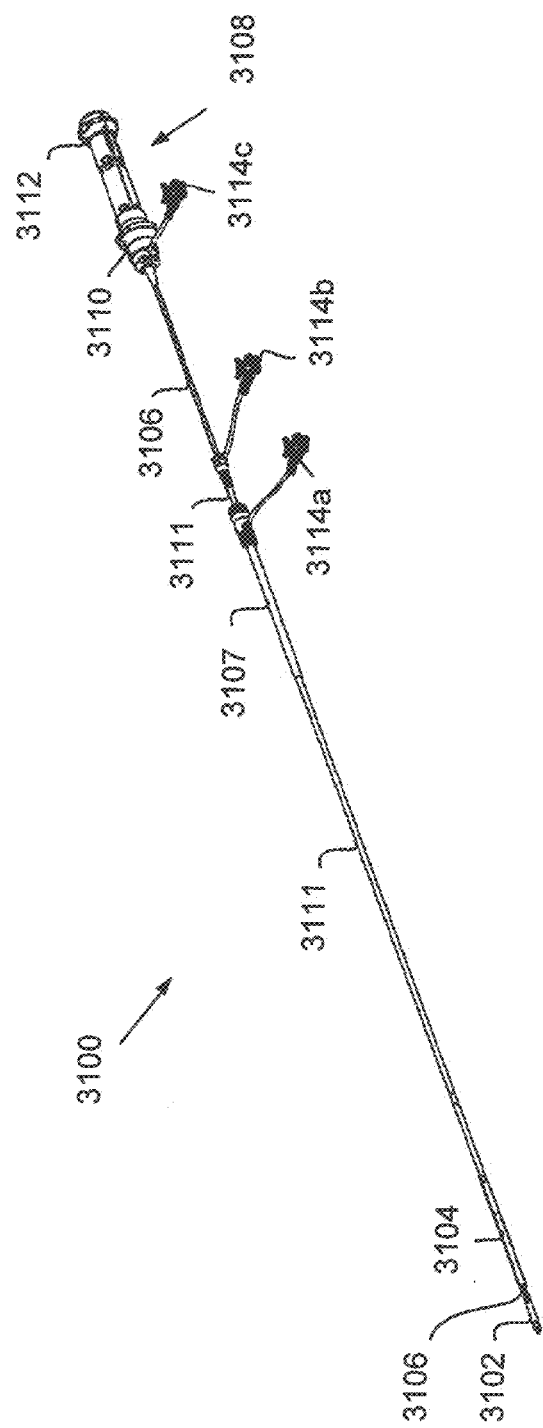
FIG. 31 is an embodiment of a delivery system for delivering a leadless pacemaker.

FIG. 31 illustrates a system 3100 configured for delivery of a leadless pacemaker 3102 into a patient and/or retrieval of the leadless pacemaker 3102 from the patient. The system 3100 can include a guide catheter sheath 3111 including an atraumatic distal end 3104 in the form of a sleeve 3104. Delivery system 3100 can also have a pacemaker introducer sheath 3107 and a catheter shaft 3106. Catheter shaft 3106 includes at its proximal end a handle 3108, deflection knob 3110, and tether shuttle 3112. Each of longitudinal bodies 3107, 3111, 3106 includes a flush port 3114a, 3114b, 3114c extending respectively therefrom. As can be understood from FIG. 31, the catheter shaft 3106 extends through the guide catheter sheath 111, which extends through the introducer sheath 107. Each of the longitudinal bodies 3106, 3107, 3111 are displaceable proximal-distal relative to each other.

As discussed in greater detail below, the atraumatic sleeve 3104 may be formed of a shape-memory material that is sufficiently flexible to allow the atraumatic sleeve 3104 to encompass the leadless pacemaker 3102 or to have a diameter that is smaller than a diameter of the leadless pacemaker 3102 when not encompassing the leadless pacemaker 3102. The deflection knob 3110 can be used to deflect the catheter shaft 3106 within the catheter sheath 3111 to steer and guide the catheter shaft 3106 during implantation and/or removal of the leadless pacemaker 3102. The flush ports 3114a, 3114b, and 3114c can be used to flush saline or other fluids through the catheter. The atraumatic sleeve 3104 forms the distal most region of the catheter sheath 3111. The catheter sheath 3111 can be advanced distally over the catheter shaft 3106 such that the atraumatic sleeve 3104 is caused to extend over the leadless pacemaker 3102. Also, distal displacement of the catheter sheath 3111 relative to the catheter shaft 3106 can be used to provide additional steering and support for the delivery catheter during implantation and to surround the pacemaker as it is introduced through a trocar or the introducer sheath 3107 into the patient. The catheter sheath 3111 can be retracted proximally over the catheter shaft 3106 such that the atraumatic sleeve 3104 is caused to retract from over the leadless pacemaker 3102, the shape-memory construction of the atraumatic sleeve 3104 being such that atraumatic sleeve 3104 self-biases into a reduced diameter. In one embodiment, the reduced diameter of the atraumatic sleeve 3104 is no greater than the diameter of the leadless pacemaker 3102.

Alternatively, the sleeve 3104 may have a neutral shape it assumes or biases into wherein its internal diameter is the same as the outer diameter of the headless pacemaker 3102 such that the sleeve 3104 can readily slip over and off of the leadless pacemaker 3102 without the sleeve 3104 changing its internal diameter. However, on account of the flexibility and shape memory nature of the sleeve 3104, the sleeve 3104 can be compressed for passage through the introducer 3107 and, once through the introducer 3107, the shape memory nature of the sleeve 3104 causes the sleeve 3104 to assume its neutral shape with its internal diameter that is the same as the outer diameter of the leadless pacemaker 3102.

Figure 32A:
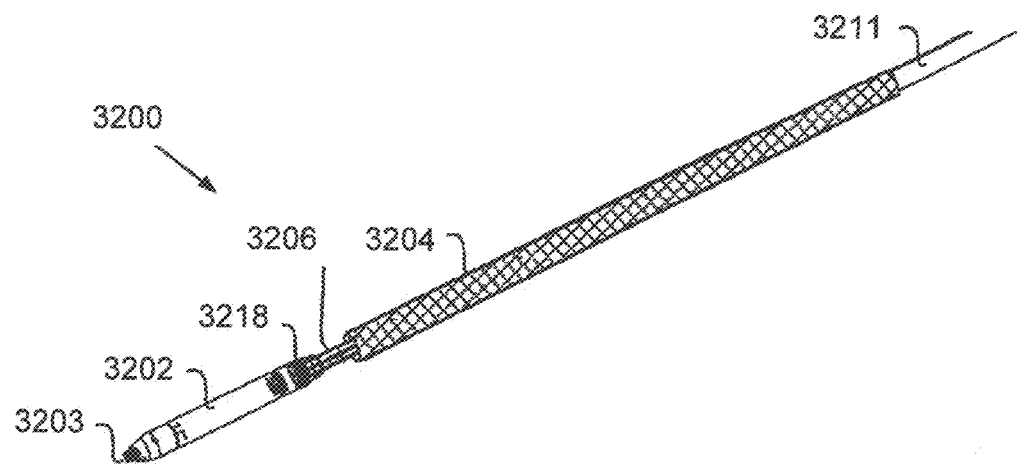
FIG. 32A is a close-up view of a distal portion of the delivery system with an atraumatic end of the delivery system proximal of the leadless pacemaker.
Figure 32B:
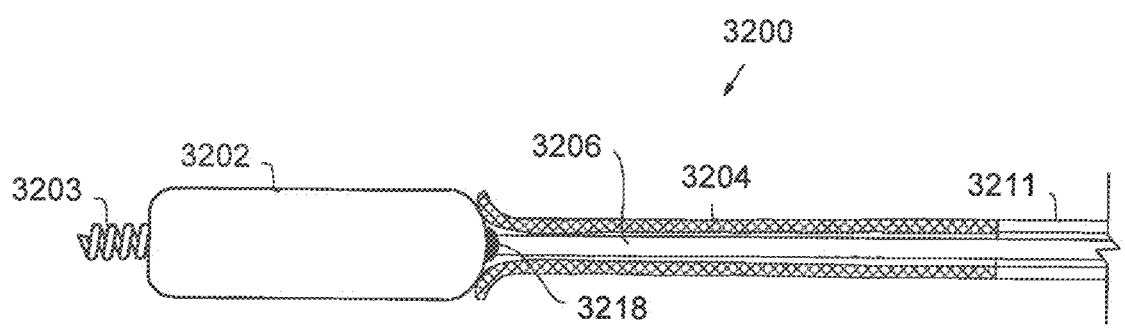
FIG. 32B is a diagrammatic longitudinal cross section of the leadless pacemaker and delivery system in the condition illustrated in FIG. 32A.

FIG. 32A is a close-up view of a distal portion of a system 3200 and pacemaker 3202, and FIG. 32B is a diagrammatic longitudinal cross section of the same components in the same condition. The pacemaker 3202 of FIGS. 32A and 32B can include a helix 3203 for attachment of the pacemaker 3202 to tissue. In FIGS. 32A and 32B, the pacemaker 3202 is attached to a docking cap 3218 of the catheter shaft 3206. The atraumatic sleeve 3204, along with the rest of the guide catheter sheath 3211, is shown pulled back proximally along the catheter shaft 3206 to expose the pacemaker 3202 and the helix 3203. Thus, when the guide catheter sheath 3211 is pulled back proximally thereby causing its atraumatic distal end region 3204 to pull back proximally, as shown in FIGS. 2A and 2B, the pacemaker 3202 is in an exposed, delivery configuration such that the helix 3203 is exposed for screwing into or out of heart tissue at a implantation target site.

Figure 32C:
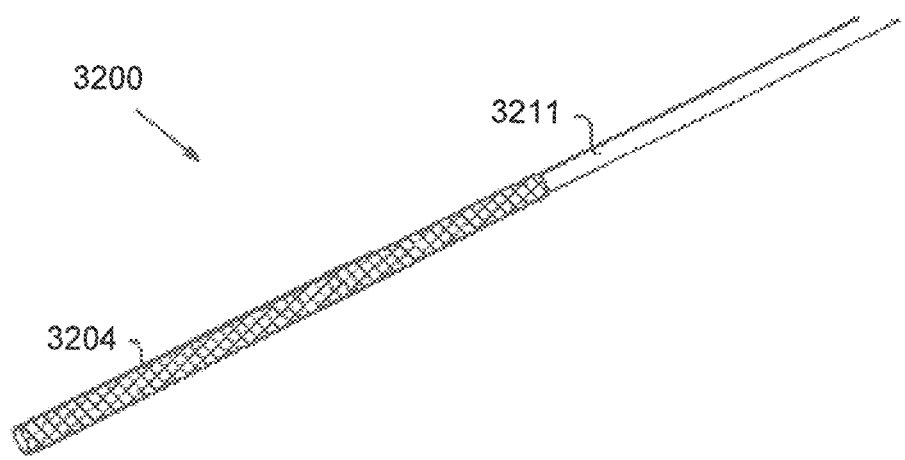
FIG. 32C is the same view as FIG. 32A, except the atraumatic end of the delivery system has been distally displaced over the leadless pacemaker.
Figure 32D:
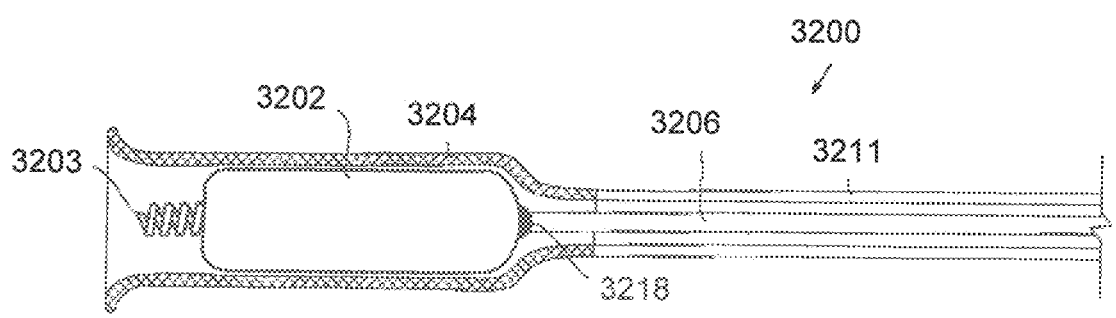
FIG. 32D is a diagrammatic longitudinal cross section of the leadless pacemaker and delivery system in the condition illustrated in FIG. 32C.
Figure 33A:
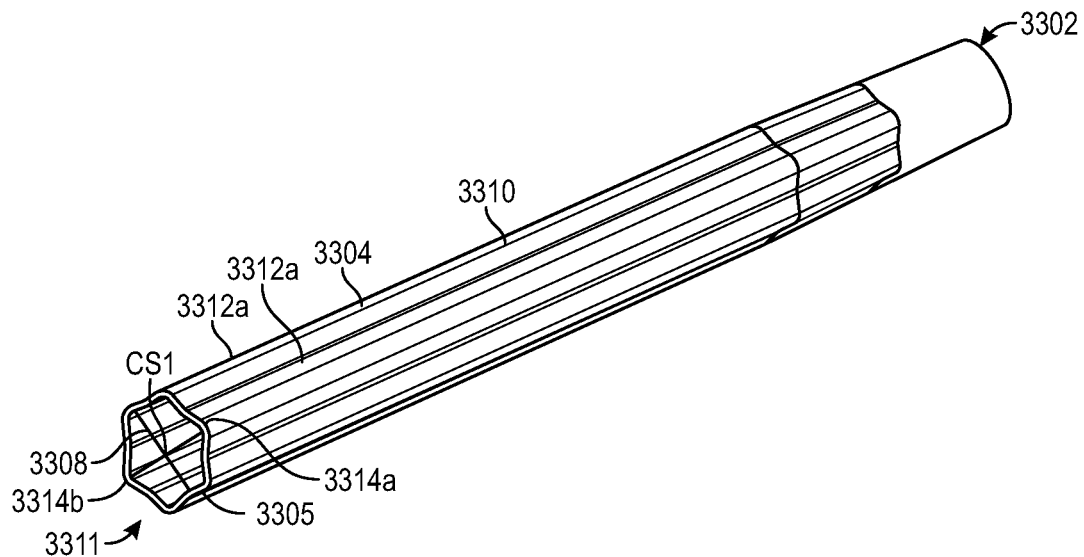
FIGS. 33A-35B are schematic side and cross-sectional views of a sleeve.

In FIGS. 32C and 32D, the guide catheter sheath 3211 is extended distally to cause the atraumatic sleeve 3204 to cover the catheter shaft 3206, the pacemaker 3202, and the helix 3203 to protect patient tissue from the sharp edges of the helix 3203 during implantation. Thus, when the catheter sheath 3211 and its atraumatic distal end region 3204 in the form of the sleeve 3204 are advanced distally to protect the pacemaker 3202 and the helix 3203, as shown in FIGS. 32C and 32D, the pacemaker 3202 and the helix 3203 are in a protected, advancement configuration, FIG. 33A is a close-up view of the atraumatic distal end region 3204 of the sleeve 3304 of the catheter sheath of the delivery system. FIG. 33A illustrates the sleeve 3304 in a contracted condition. The sleeve 3304 extends between a trailing end 3302 and a leading end 3311 and includes a body 3305 that is longitudinally pleated so as to include a plurality of generally rectangular segments 3310 extending from the trailing end 3302 to the leading end 3311, the segments 3310 being connected to one another in a circumferential manner to define a lumen 3308 through the body 3305. The body 3305 has a substantially star-shaped cross-section, with each segment 3310 being joined to adjacent segments along edges 3312a, 3312b to define outer vertices 3314a and inner vertices 3314b of the star-shaped body 3305. As shown, the body 3305 includes six outer vertices 3314a and six inner vertices 3314b, but it will be understood that the body 3305 may include multiple segments 3310 and that the term "star-shaped configuration" may refer to any configuration having three or more outer vertices 3314a and three or more inner vertices 3314b. In its expanded condition, the sleeve 3304 may have a maximum cross-section "cs1," measured from one outer vertex 3314a to a diametrically opposed outer vertex 3314a, that is from and including approximately 12 French to and including approximately 25 French.

The body 3305 may be formed of a shape-memory material that is heat-set into the star-shaped configuration of FIG. 33A. In some examples, a thermoplastic elastomer, such as polyether block amide ("PEBAX®"), with a durometer of approximately 25 to approximately 72 on scale D, may be used to form the body 3305. The segments 3310 may have a thickness of about 0.020". The edges 3312a, 3312b may also have a thickness of approximately 0.020" or less such that the vertices 3314a, 3314b are formed at predetermined positions to act as living hinges. The durometer of the polymer can be adjusted for either added flexibility or increased axial rigidity, depending on the application or desired performance.

Figure 33B:
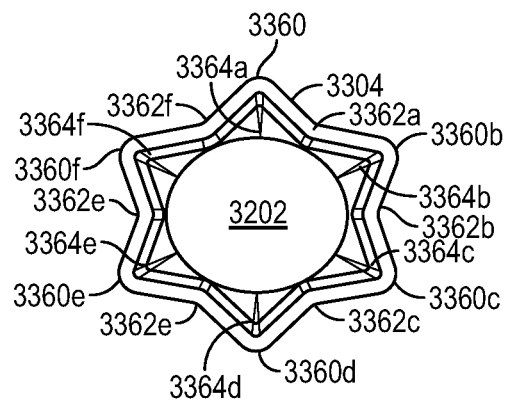
Figure 33C:
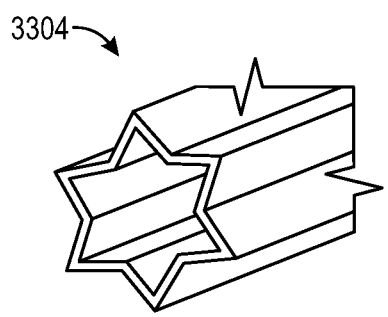

FIG. 33B is a traverse cross-section of the sleeve 3304 in an expanded position over the leadless pacemaker 3202. FIG. 33C is a side view of the sleeve 3304 in a contracted position. The body 3305 may be flexible so that when the pacemaker 3202 is passed through the lumen 3308, the segments 3310 are capable of being pushed radially outward so that the body 3305 transitions from the contracted condition of FIG. 33C to an expanded condition shown in FIG. 33B. In both the contracted condition of FIG. 33C and expanded condition shown in FIGS. 33A and 33B, the body 3305 may include a star configuration. However, in the expanded condition shown in FIGS. 33A and 33B, the body 305 assumes a slightly more tubular/rounded configuration than shown in FIG. 33C. In FIGS. 33A, 33B, and 33C, the star configuration of the body 305 includes six outer points 3360*a-f* and six inner points 3362*a-f*. At each outer point 3360*a-f*, the star configuration of the body 3305 includes a pocket recess 3364*a-f*.

The pocket recesses 3364*a-f* allow the sleeve 3304 to collapse and expand to account for different size pacemakers with varying degrees of tissue overgrowth. During retrieval, the pacemakers can have unknown amounts of tissue growth on the pacer body. To accommodate this variation, the inner diameter of the inner points 3362*a-f* can be adjusted to whatever size pacemaker is required, including any potential tissue overgrowth, to achieve the desired fit. By making the sleeve 3304 expandable to account for unknown amounts of tissue and/or different sized pacemakers, the sleeve 3304 can help align the pacemaker axially and improve torque transmission with the walls of the sleeve 3304 applying friction to deliver the pacemaker with the to pacemaker delivery system 3100 (FIG. 31). During a leadless pacemaker retrieval operation, the inner points 3362*a-f* of the star configuration of the body 3305 may also be used to score, scrape, or otherwise free the pacemaker from tissue overgrowth by rotating the sleeve 3304 around the pacemaker. Other constructions of the sleeve 3304 besides a star-shape may also be used to score tissue overgrowth from the pacemaker.

Figure 34A:
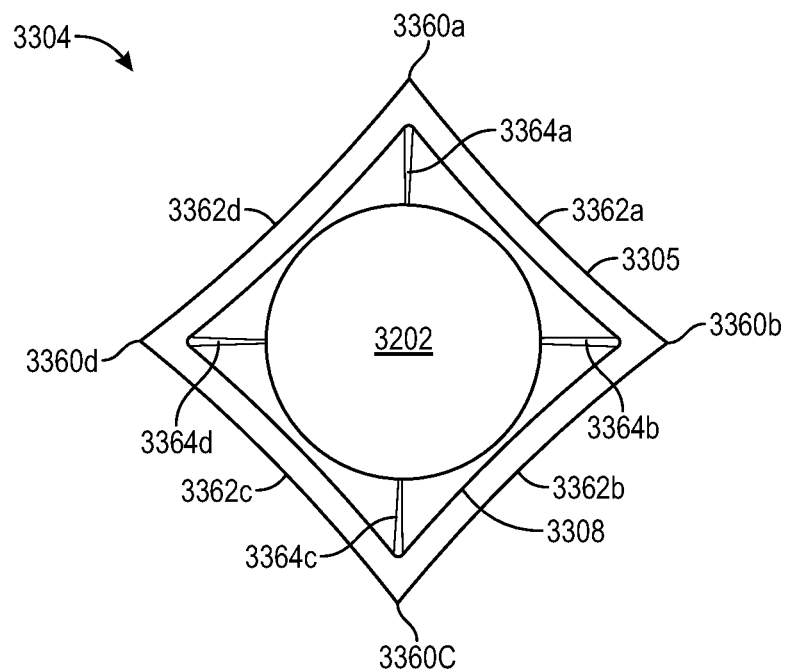
Figure 34B:
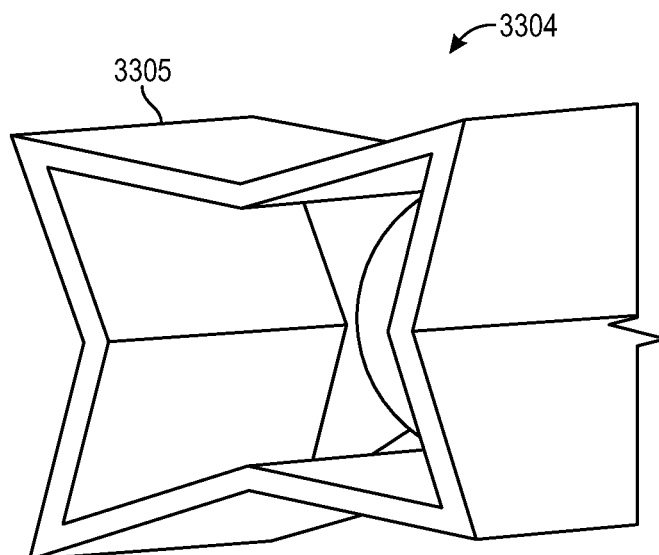

FIGS. 34A and 34B illustrate a star configuration of the body 3305 including four outer points, 3380*a-d*, four inner points, 3362*a-d*, and four pocket recess 3364*a-d*. FIG. 34A is a transverse cross section of an embodiment of the pacemaker 3202 within the lumen 3308 of the sleeve 3304. FIG. 34B is a side view of a contracted sleeve 3304.

Figure 35A:
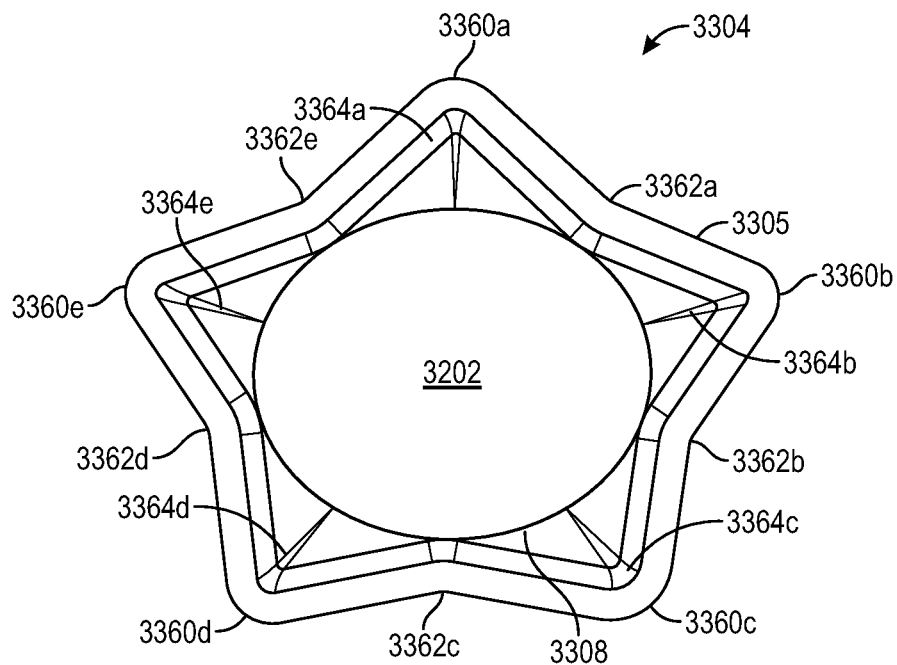
Figure 35B:
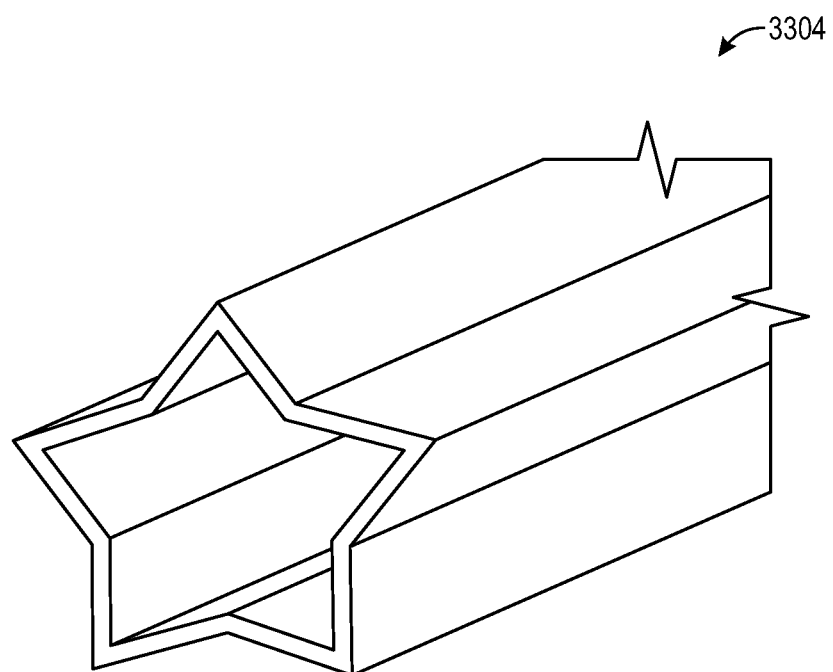

FIGS. 35A and 35B illustrate a star configuration of the body 3305 including five outer points 3360*a-e*, five inner points 3362*a-e*, and five pocket recess 3364*a-e*. FIG. 35A is a transverse cross section of an implementations of pacemaker 3202 within lumen 3308 of sleeve 3304. FIG. 35B is a side view of a contracted sleeve 3304.

In certain implementations, the body 3305 may include more or fewer inner and outer points and pocket recesses than illustrated. Moreover, the number of inner points 3362 and the outer diameter of the points 3362 may be adjusted to create adequate clearance for varying amounts of tissue growth on the pacemaker 3202 and pacemakers having different diameters. In certain implementations, the body 3305 may be segmented or discontinuous about its circumferential extent. Conversely, the body may be non-segmented or continuous about its circumferential extent.

Figure 36A:
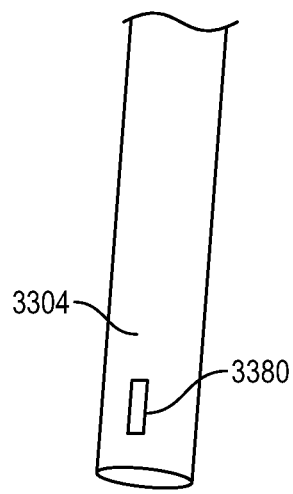
FIG. 36A-36B are radiopaque markers in accordance with certain embodiments.
Figure 36B:
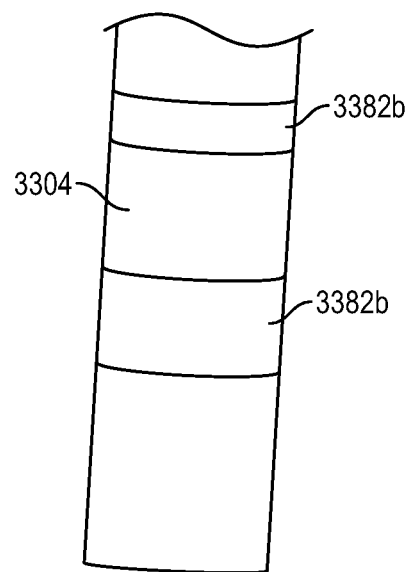

FIGS. 36A and 36B are fluoroscopic images of a distal end of an atraumatic sleeve in accordance with this disclosure. As illustrated in FIG. 3H, a rectangular radiopaque marker 3380 at the distal end of the atraumatic sleeve may be used to determine under fluoroscopy the location of the atraumatic tip and, in particular, the location of the atraumatic tip with respect to the leadless pacemaker. For example, in some implementations, fluoroscopy may be implemented to determine whether the distal tip of the atraumatic sleeve 3204 has past the helix 3203 of the leadless pacemaker 3202 (as shown in FIG. 32D), such that the sharp edges of the helix 3203 are not exposed to surrounding sensitive tissue.

Certain prior leadless retrieval and delivery catheter systems used a sleeve including ePTFE with a flat 90/10 PtIr tip marker 1.27 mm×3.175 mm placed in the wall 2 mm from the distal tip. In order to maintain a lower catheter profile (i.e., a smaller French size), which affects the safety and comfort of the procedure, a full round marker band may not be used in implementations of the current disclosure. However, a radiopaque feature around the entire distal tip of sleeve 3304 would improve visibility for a user, aiding in determining whether the distal tip of the atraumatic sleeve 3304 is past the helix 3203 of the pacemaker 3202, such that the sharp edges of helix 3203 are not exposed to surrounding sensitive tissue.

This disclosure provides for apparatuses and methods that could be employed to maintain the flexibility of sleeve 3304, such that sleeve 3304 repeatedly and reliably expands and compresses during a pacemaker retrieval or delivery procedure, while increasing the radiopacity of the atraumatic sleeve 3304, thereby improving safety of such procedures.

FIG. 36B illustrates the atraumatic sleeve 3304 in which pad printing radiopaque ink 3382*a*, 3382*b* has been applied the sleeve 3304. In alternative implementations, radiopaque ink can be placed in interrupted spots in specific locations on the sleeve 3304. In certain implementations, radiopaque medical ink, such as Class VI Medical grade ink, may be used in printing wherein tungsten or other high radiopaque metals are loaded in medical grade ink and printed onto the surface of the sleeve 3304 by a suitable printing technique, such as, for example, engraving, mono-type, offset, cliché transfer, ink jet or gliceé printing. In one embodiment, an ink composition for radiopaque marker for a PEBAX® surface includes a suitable polymeric binder that adheres well to a PEBAX® surface, a biocompatible dye or pigment, a radiopaque material and a solvent that dissolves the polymeric binder. In addition, the ink composition may contain inorganic white solid materials such as titanium dioxide (to adjust ink shade) and a viscosity modifier.

Another method of providing a radiopaque marker could be to plate the sleeve 3304 at the distal tip with a radiopaque material that would be able to expand and collapse with the sleeve, without detrimentally increasing the diameter of the sleeve 3304 and without compromising the flexibility and expandability of the system. Providing a flexible radiopaque marker around the entire distal tip of the sleeve 3304 also advantageously improves visibility of the sleeve 3304 compared to prior art marker squares. In certain implementations, the radiopaque marker may be applied from a solution of dissolved metal. The attachment mechanism can occur either using an electrical current to drive the attachment reaction, or more preferably by utilizing an autocatalytic chemical reaction requiring no electrical motive force, i.e., an electroless plating reaction. A significant advantage of the electroless plating process is the ability to produce deposits with uniform thickness on parts with complex geometries and shapes. Examples of electroless plating processes and compositions that may be used in accordance with the present invention are disclosed in U.S. Pub. No. 2016/0121007 and U.S. Pat. Nos. 3,123,484; 3,148,072, 3,338, 726, 3,719,508, 3,745,039, 3,754,939, 3,915,717, 4,152,164, 6,143,059, 6,281,157, 6,524,642, 7,846,503, and 9,462,699, each of which is incorporated herein by reference. In certain implementations, radiopaque material of radiopaque marker 370 may include tungsten, platinum, gold, or etc. that may be plated to sleeve 3304.

In certain implementations, at least the distal tip of sleeve 3304 may include a dual-wall construction including a woven wire band residing between a PEBAX® inner wall and PEBAX® outer wall, wherein the woven wire includes radiopaque wires braided with non-radiopaque wires. In one embodiment, the wires may have a diameter range of approximately 0.003 inch and approximately 0.01 inch. In accordance with this embodiment, the radiopaque braid would be able to expand and collapse with the sleeve, without detrimentally increasing the diameter of the sleeve 3304 and without compromising the flexibility and expandability of the system, while providing a flexible radiopaque marker around the entire distal tip of sleeve 3304. The mechanical properties of the radiopaque wires are selected to match the mechanical properties of the non-radiopaque wires, in order to increase the durability and consistence of the mesh, while providing for a self-expanding or self-contracting radiopaque marker band. The non-radiopaque wires can include superelastic material. In certain implementations, at least some of the radiopaque wires may include radiopaque nitinol (a ternary alloy consisting of a blend of nickel, titanium, and platinum) to provide for a more superelastic marker material. U.S. Pat. No. 9,320,590, incorporated herein by reference, discloses radiopaque wire and non-radiopaque wire components of woven wire bands that may be used in accordance with the implementations of the invention. U.S. Pub. No. 2016/0121007, incorporated herein by reference, describes a method of plating a braided wire that may be used in accordance with implementations of the invention to join the wires to each other at points of contact that torsionally stiffens the braid, while still permitting flexibility in the braid.

In certain implementations, the dual-wall construction may be included throughout the sleeve 3304, in order to provide reinforcement. The wire reinforcement may include at least one of longitudinally extending wires, radially extending wire rings, or a lattice of longitudinally extending wires and radially extending wire rings. The stiffening wires may be in the form of a plurality of longitudinally extending wires evenly radially dispersed in the space between the inner and outer walls. Alternatively, the stiffening wires may be in the form of a plurality of radial rings evenly longitudinally dispersed in the space between the inner and outer walls. In yet another alternative, the plurality of longitudinally extending wires and plurality of radial rings may be combined to form a wire mesh or lattice between the inner and outer walls. Regardless of how the stiffening wires are arranged between the inner and outer walls, the stiffening wires increase the column strength of the sleeve.

In some implementations, the length of the sleeve 3304 may have a range of approximately 2 inches to approximately 3 inch with a preferred length range of approximately 2.5 inches depending on the length of the leadless pacemaker to be received in the sleeve 3304. In one embodiment, the thermoplastic elastomer of the sleeve 3304 may include: a polyether block amide ("PEBAX®"), polyethylene terephthalate ("PET"), polyethylene ("PE"), nylon, urethane, polyester, or a blend of any of the aforementioned where appropriate.

In certain implementations, the sleeve 3304 is coated with a hydrophilic, drug, parylene or silicone base coating to inhibit or prevent thrombus during the procedure.

Figure 37:
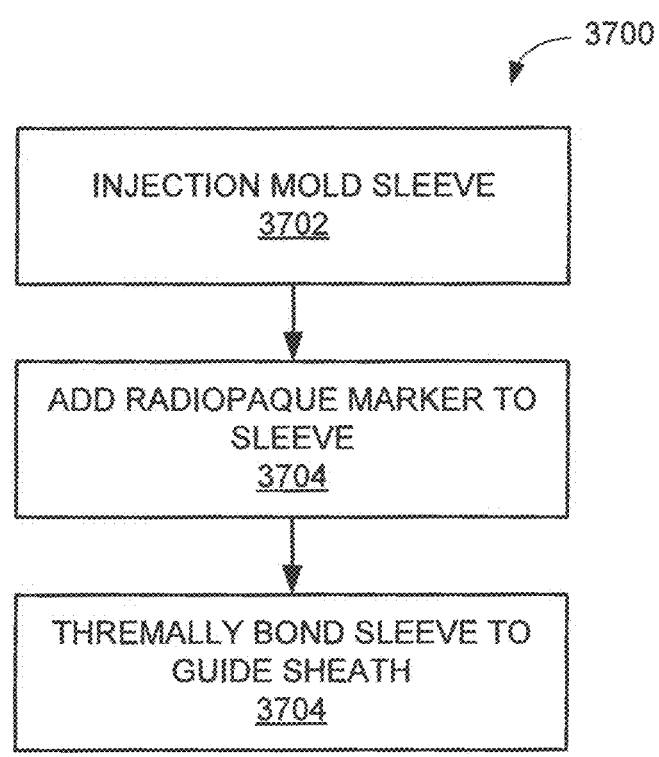
FIG. 37-40 are flow charts outlining methods of manufacturing the sleeve and its joining to a tubular body of the catheter sheath to become part of the catheter sheath.

In certain implementations, the sleeve 3304 is manufactured by a molding or extrusion process and coupled to the rest of the catheter sheath 3311 via a method 3700 outlined in flow chart of FIG. 37. In accordance with one implementation of the method 3700, a first step 3702 includes manufacturing a PEBAX® star-shaped sleeve using an injected molding process. At step 384, a radiopaque maker is added to the sleeve using a radiopaque ink. In certain implementations, the radiopaque marker is applied all the way around the sleeve (such as by applying a complete band or interrupted spots in specific locations) or by plating the sleeve at the tip with a radiopaque material that is able to expand and collapse with the sleeve, as described in more detail above. At step 3704, the sleeve is then thermally bonded to the guide sheath of the delivery system.

Figure 38:
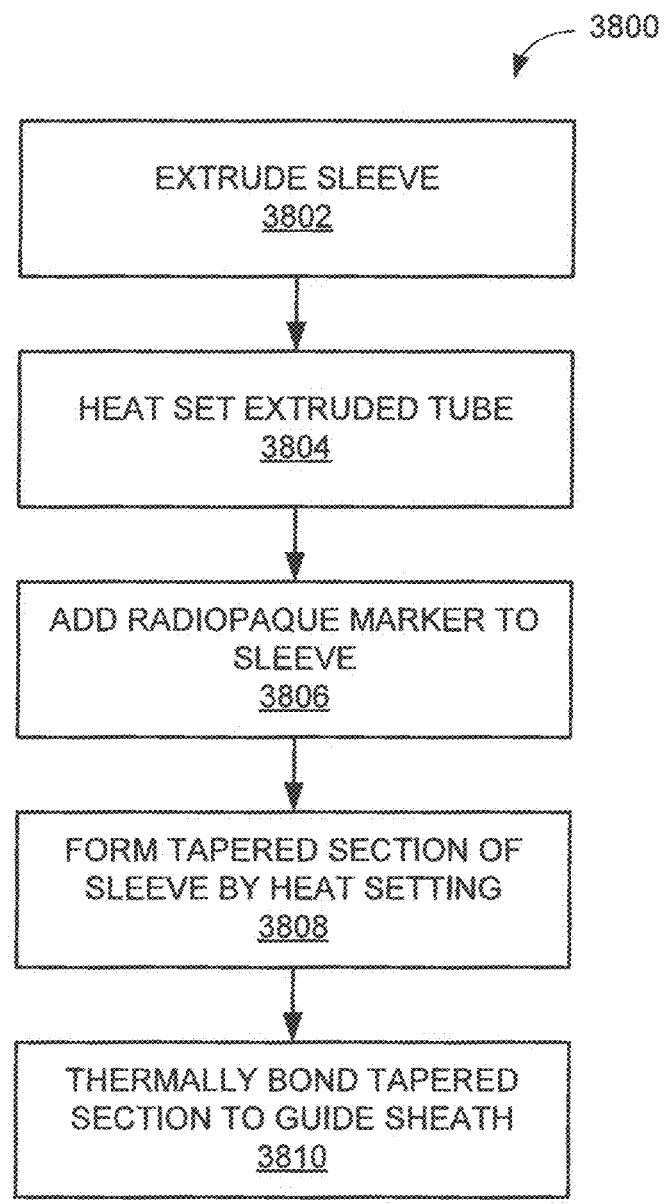

FIG. 38 is a flow chart of an alternative method 3800 of manufacturing a sleeve in accordance with this disclosure in which the sleeve is formed, in part using a heat flow extrusion process. At step 3802, a PEBAX® extruded tube is obtained with an oval cross-section of 1.27×0.69 mm O.D. At step 3804, the extruded tube are heat set or cross-linked by irradiation (e.g. gamma radiation or electron beam radiation) to sustain the star configuration. In certain implementations, the composite tube further includes a coil, braid, or stent reinforcement.

At step 3806, a radiopaque maker is added to the sleeve in certain implementations, the radiopaque marker is applied all the way around the sleeve (such as by applying a complete band or interrupted spots in specific locations) or by plating the sleeve at the tip with a radiopaque material that is able to expand and collapse with the sleeve, as described in more detail above. At step 3808 a tapered section is formed on the sleeve by again heat setting the tube. At step 3812, the taper section of the sleeve is then thermally bonded to the guide sheath of the delivery system.

Figure 39:
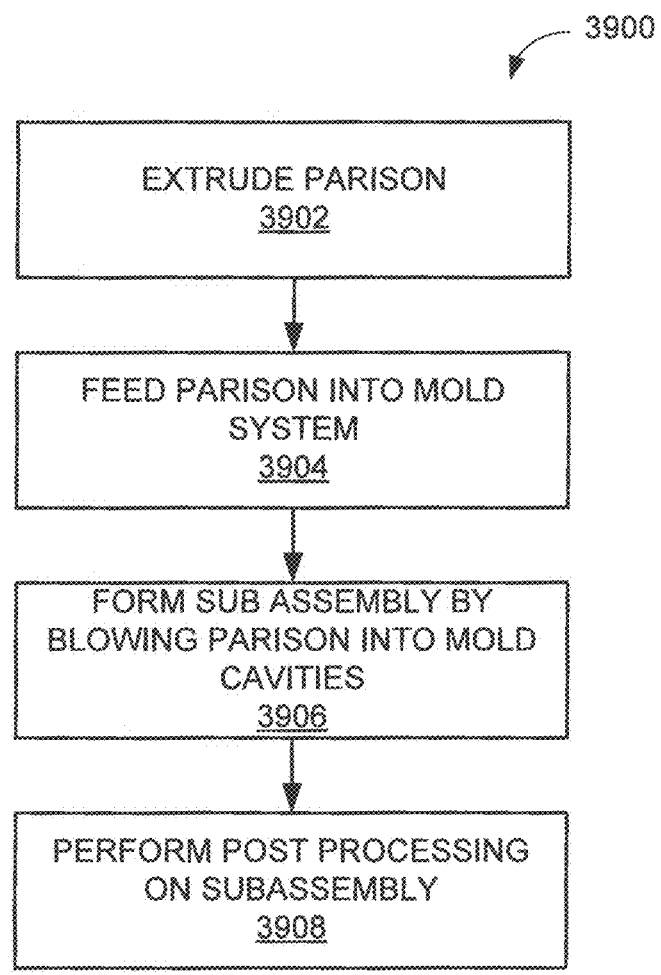

FIG. 39 is a flow chart of another method 3900 of manufacturing of manufacturing a sleeve in accordance with this disclosure and, in particular, forming a PEBAX® star-shaped sleeve is manufactured through a multistage Wow molding process. According to the method 3900, at step 3902 a piece of extrusion is used to form a parison using heat, pressure, and tension. At step 3904, the parison is fed into a multi-piece mold system. The molds of the multi-piece mold system may consist of cavities designed to the exterior dimensions of the desired part. At step 3906, using heat and pressure, the parison is blown in the mold cavities to form a subassembly. In certain implementations, pressure in the range of 300 psi to 500 psi is used. In certain implementations, a pressure of 290 psi is used. In certain implementations, the subassembly is heat-set using a temperature in the range of 85-200° C. In certain implementations, the subassembly is heat-set using a temperature of approximately 149° C. or 300° F. The blow molding may consist of multiple cycles to form specific features, i.e. atraumatic tips or cone neck geometry. In certain implementations, the subassembly is post processed at step 3908, i.e. tipping, final cut to length, etc.

Figure 40:
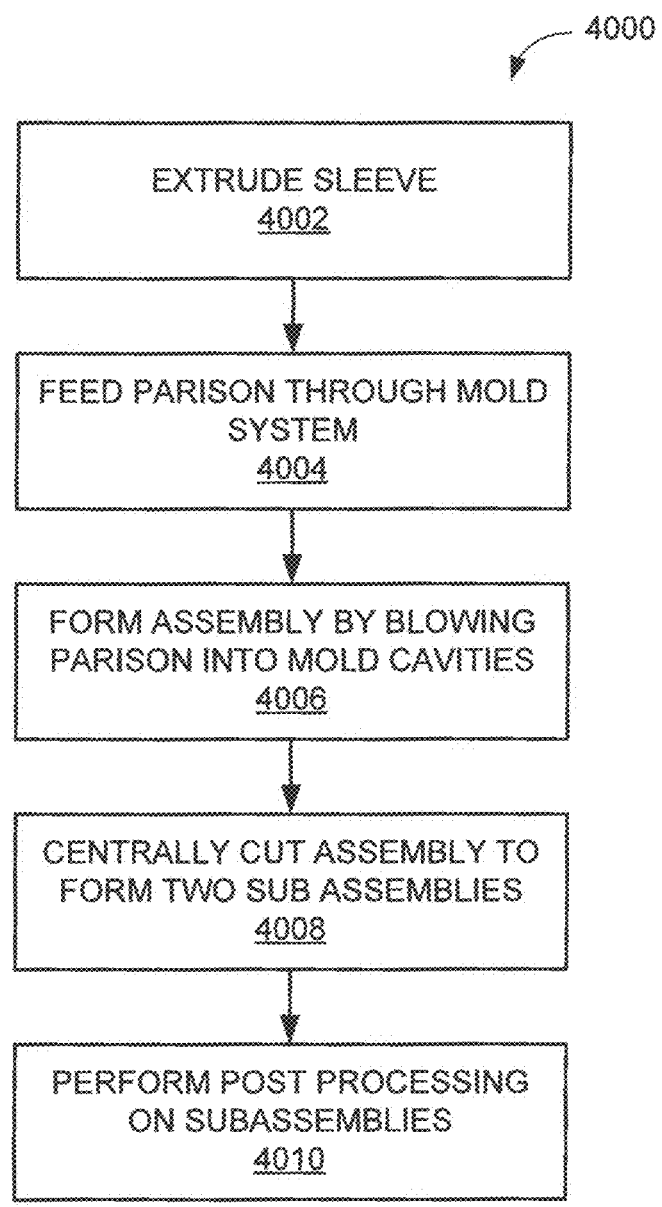

FIG. 40 is a flow chart of another method 4000 of manufacturing of manufacturing a sleeve in accordance with this disclosure and, in particular, forming a PEBAX® star-shaped sleeve through a multistage blow molding process. At step 4002, a piece of extrusion is used to form a parison using heat, pressure, and tension. At step 4004, the parison is fed into a multi piece mold system. The molds may consist of cavities designed to the exterior dimensions of the desired part. Using heat and pressure, at step 4006, the parison is blown in the mold cavities to form a subassembly. In certain implementations, the blow molding process yields a symmetrical assembly. At step 4008, the symmetrical assembly is cut centrally to form two subassemblies. At step 4010, the subassemblies are post processed to form an atraumatic tip.

After the delivery system is inserted through the introducer sheath into the patient, the sheath can be advanced distally over the leadless pacemaker. Advancing the sleeve distally over the pacemaker causes the pocket recesses of the star configuration to expand, thereby increasing the diameter of the sleeve so that it can slide over and cover the pacemaker and fixation helix.

During initial insertion of the delivery system into a patient, a physician can gain access to the patient's venous system with an introducer sheath using the Seldinger technique (not shown). The delivery system, including the leadless pacemaker, catheter sheath and catheter shaft, can then be advanced through the introducer sheath into the patient's venous system to facilitate delivery of the pacemaker into the heart. Reducing the diameter of the pacemaker, the delivery system, and thus the introducer sheath, provides for easier and less intrusive access to a patient's venous system.

Figure 41:
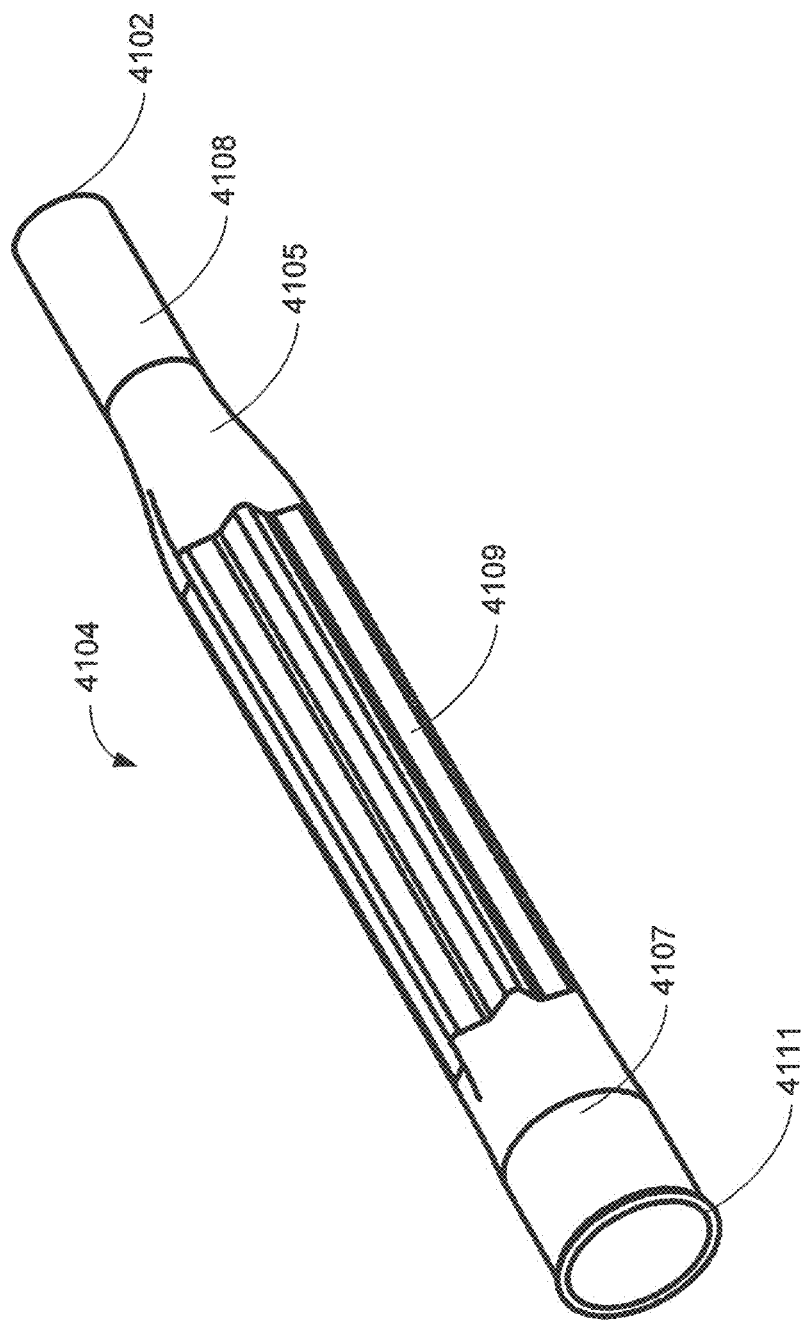
FIG. 41 is an isometric view of an alternative sleeve.

FIG. 41 is an isometric view of an alternative sleeve 4104 that may be used with the catheter sheath of the delivery system. FIG. 41 illustrates the sleeve 4104 in a contracted condition. The sleeve 4104 extends between a trailing end 4102 and a leading end 4111 and includes a body 4105.

The body 4105 includes a leading body portion 4107, a trailing body portion 4108, and an intermediate body portion 4109 extending between the leading body portion 4107 and the trailing body portion 4108. The intermediate body portion 4109 may include longitudinal pleats or folds such that the intermediate body portion 4109 includes a star-shaped or other cross-section in accordance with this disclosure. For example, the intermediate body portion 4109 may have a cross-section similar to any of the implementations illustrated FIGS. 33A-35B.

Figure 42A:
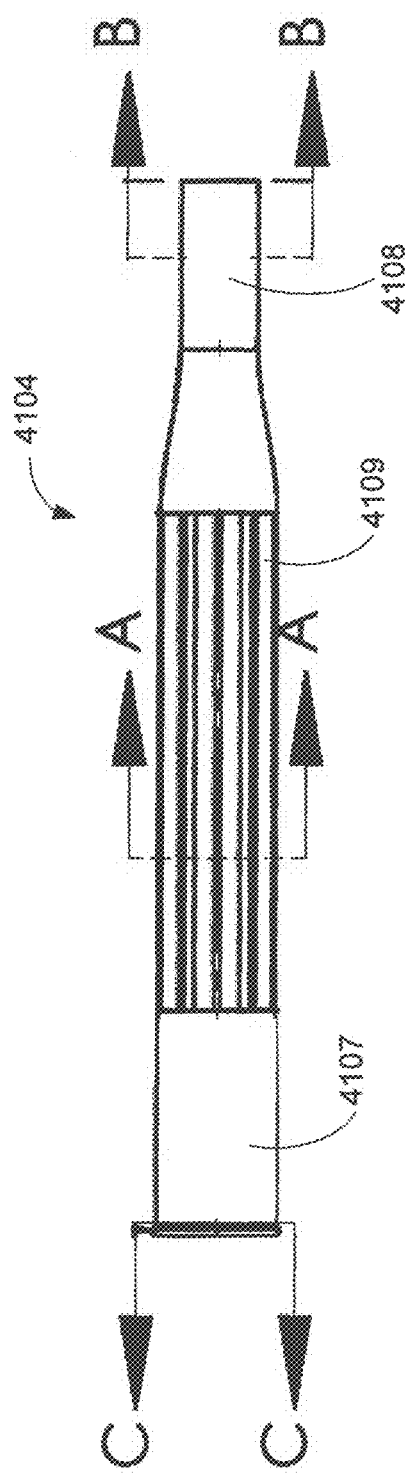
FIG. 42A is a side elevation view of the alternative sleeve of FIG. 41.
Figure 42D:
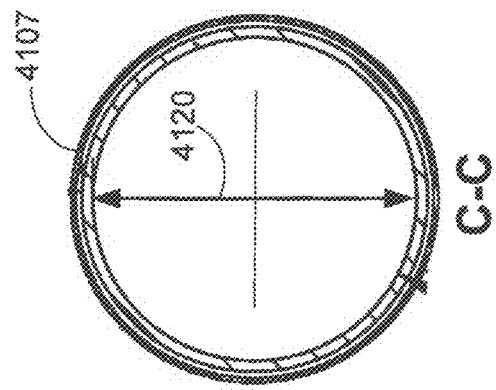
FIGS. 42B-42D are transverse cross-sectional views of the alternative sleeve of FIG. 41.
Figure 42C:
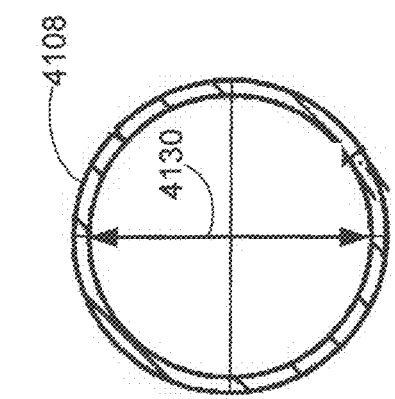
Figure 42B:
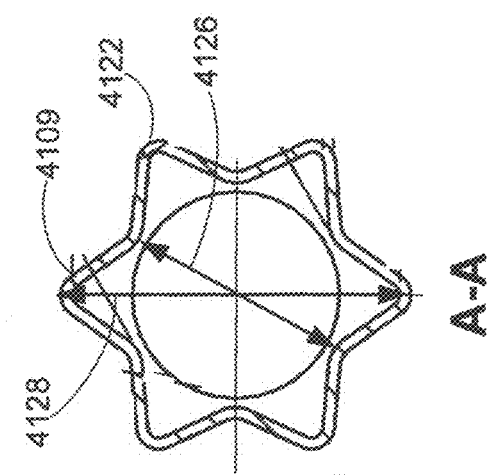

FIG. 42A is a longitudinal side-view of the alternative sleeve 4104 and FIGS. 42B-42D are cross-sections taken along A-A, B-B, and C-C, respectively. More specifically, cross-section A-A is a cross-sectional view of the intermediate body portion 4108 directed in the proximal direction, cross-sectional view B-B is a cross-sectional view of the trailing body portion 4108 directed in the proximal direction, and cross-sectional view C-C is a cross-sectional view of the leading body portion 4107 directed in the distal direction. In certain implementations, the leading body portion 4107 may extend approximately 0.600 inches, the intermediate body portion 4109 may extend approximately 1.330 inches, and the trailing body portion 4108 may extend approximately 0.450 inches with a tapered transitional portion 4110 extending between the intermediate body portion 4109 and the trailing body portion 4108.

As shown in FIGS. 42A-42D, the leading body portion 4107 may have define a first internal diameter 4120, the intermediate body portion 4108 may include points 4122 or similar features that define a minimum inner diameter 4126 and a maximum outer diameter 4128, and the trailing body portion 4108 may define a second internal diameter 4130. In certain implementations, various diameters defined by the portions of the alternative sleeve 4104 may reduce toward the trailing end portion 4106. For example, the first internal diameter 4120 may be greater than or equal to the maximum outer diameter 4128 and the minimum inner diameter 4126 may be greater than the second internal diameter 4130. For example, in certain implementations, the first internal diameter 4120 may be approximately 0.300 inches, the maximum outer diameter 4128 may be approximately 0.290 inches, the minimum inner diameter may be approximately 0.200 inches and the second internal diameter 4130 may be approximately 0.184 inches.

As can be understood from FIGS. 32A-42D, sleeves according to this disclosure may have a woven expandable configuration that self-biases to a reduced diameter that is at least as small as the diameter of a leadless pacemaker being delivered or retrieved and is sufficiently readily expandable by simply distally displacing the sleeve against the leadless pacemaker such that the sleeve expands about and envelopes leadless pacemaker. Thus, during initial implantation of the pacemaker through an introducer sheath into the patient, the sleeve can be positioned just proximal to the pacemaker, as illustrated in FIGS. 32A-32B, the diameter of the sleeve self-biasing to its minimum diameter so as to have a cross sectional diameter close to or equal to the same diameter as the pacemaker. This allows a smaller diameter introducer sheath to be used than would normally be necessary, since those delivery systems must incorporate a larger introducer sheath to allow passage of a full sized sleeve. After the delivery system is inserted through the introducer sheath into the patient, the sheath can be advanced distally over the leadless pacemaker. Advancing the sleeve distally over the pacemaker causes the braided or woven expandable configuration of the sleeve to expand sufficiently with respect to its diameter that the sleeve can slide over and cover the pacemaker and fixation helix, as illustrated in FIGS. 2C-2D, thereby preventing the helix from contacting patient tissue.

It should be noted that while the sleeve is shown in FIGS. 32B and 32D as having a neutral configuration with an internal diameter that is less than the outer diameter of the leadless pacemaker, thereby requiring the sleeve to expand as it is distally displaced over the leadless pacemaker for the leadless pacemaker to be received in the internal volume of the sleeve, in other implementations, the sleeve has a neutral configuration with an internal diameter that is the same as the outer diameter of the leadless pacemaker. More specifically, the sleeve may have a neutral shape it assumes or biases into wherein its internal diameter is the same as the outer diameter of the leadless pacemaker such that the sleeve can readily slip over and off of the leadless pacemaker without the sleeve changing its internal diameter. However, on account of the flexibility and shape memory nature of the sleeve, the sleeve can be compressed for passage through the introducer and, once through the introducer, the shape memory nature of the sleeve causes the sleeve to assume its neutral shape with its internal diameter that is the same as the outer diameter of the leadless pacemaker.

Any of the above mentioned implementations may also include, without limitation, electronic indicators on the system (e.g., LEDS or screens) or on adjunct support-screens to communicate status. Finally, the above mentioned implementations may also include shaft position indicators via, for example, detents located on the shaft of the deflectable catheter and complementary features for interacting on the detents, the complementary features being located on the guide catheter or even the locking hub. Of course the opposite arrangement is also possible. The position indicator aspects can be used to notify the user of the extent to which the protective sleeve covers the leadless pacemaker.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A system, comprising:
   a leadless pacemaker having a coupling feature at a proximal end; and
   a retrieval catheter comprising
   a catheter shaft,
   a handle coupled to a proximal end of the catheter shaft, and
   a docking cap having an internal surface defining a docking cap volume, wherein the docking cap is inflexible, the docking cap comprising
   a cap portion coupled to a distal end of the catheter shaft,
   a plurality of longitudinal members extending distally from the cap portion, wherein adjacent longitudinal members of the plurality of longitudinal members define an opening into the docking cap volume from an outer member surface of the docking cap to the internal surface, the opening sized to allow the coupling feature at the proximal end of the leadless pacemaker to extend at least partially through the opening during retrieval, and
   an annulus coupled to the plurality of longitudinal members opposite to the cap portion, wherein the annulus includes a transition surface extending from the internal surface to an outer edge of a distal face radially outward from the outer member surface to guide the leadless pacemaker into the docking cap volume.

2. The system of claim 1, further comprising a sheath disposed over at least a portion of the opening.

3. The system of claim 2, wherein the sheath comprises a fluorinated ethylene propylene (FEP) sheet.

4. The system of claim 2, wherein the sheath includes a heat-shrink sheet about the the plurality of longitudinal members.

5. The system of claim 1, wherein the internal surface extends perpendicular to the distal face, and wherein the transition surface includes a curved transition between the distal face and the internal surface.

6. The system of claim 5, wherein the curved transition has a radius of curvature from and including 0.017 inches to and including 0.150 inches and an arc length from and including 0.017 inches to and including 0.035 inches.

7. The system of claim 1, further comprising a torque feature disposed on an interior surface of at least one of the plurality of longitudinal members, the torque feature shaped to engage a portion of the leadless pacemaker during retrieval.

8. The system of claim 7, wherein the torque feature includes a protrusion extending into the docking cap volume, and wherein the torque feature includes a concave scallop extending from a proximal edge of the transition surface to a longitudinal face.

9. The system of claim 7, wherein the torque feature is offset from the annulus.

10. The system of claim 1, wherein the docking cap is formed from one or more of stainless steel, titanium, or a polymer loaded with a radiopaque additive.

11. The system of claim 1, wherein the docking cap volume has a diameter from and including 0.10 inches to and including 0.25 inches.

12. A catheter for retrieval of a leadless pacemaker, comprising:
    a catheter shaft having a distal shaft end; and
    a docking cap having an internal surface defining a docking cap volume, wherein the docking cap is inflexible, the docking cap comprising:
    a cap portion coupled to the distal shaft end,
    a plurality of longitudinal members extending distally from the cap portion, wherein adjacent longitudinal members of the plurality of longitudinal members define an opening into the docking cap volume from an outer member surface of the docking cap to the internal surface, the opening sized to allow a coupling feature at a proximal end of the leadless pacemaker to extend at least partially through the opening during retrieval, and
    an annulus coupled to the plurality of longitudinal members opposite to the cap portion, wherein the annulus includes a transition surface extending from the internal surface to an outer edge of a distal face radially outward from the outer member surface.

13. The catheter of claim 12, further comprising a sheath disposed over at least a portion of the opening.

14. The catheter of claim 13, wherein the sheath comprises a fluorinated ethylene propylene (FEP) heat-shrink sheet about the plurality of longitudinal members.

15. The catheter of claim 12, wherein the internal surface extends perpendicular to the distal face, and wherein the transition surface includes a curved transition between the distal face and the internal surface.

16. The catheter of claim 15, wherein the curved transition has a radius of curvature from and including 0.017 inches to and including 0.150 inches and an arc length from and including 0.017 inches to and including 0.035 inches.

17. The catheter of claim 12, further comprising a torque feature disposed on an interior surface of at least one of the plurality of longitudinal members.

18. The catheter of claim 17, wherein the torque feature includes a protrusion extending from the internal surface of one of the plurality of longitudinal members into the docking cap volume, and wherein the torque feature includes a concave scallop extending from a proximal edge of the transition surface to a longitudinal face.

19. The catheter of claim 17, wherein the torque feature is offset from the annulus.

20. The catheter of claim 12, wherein the docking cap volume has a diameter from and including 0.210 inches to and including 0.25 inches.

* * * * *